US011446328B2

(12) United States Patent
Wang

(10) Patent No.: US 11,446,328 B2
(45) Date of Patent: Sep. 20, 2022

(54) ANTIBODIES AGAINST N-ACETYLGLUCOSAMINE AND N-ACETYL-GALACTOSAMINE

(71) Applicant: B & H BIOTECHNOLOGIES, LLC, Willowbrook, IL (US)

(72) Inventor: Huiru Wang, Beijing (CN)

(73) Assignee: B & H BIOTECHNOLOGIES, LLC, Willowbrook, IL (US)

( * ) Notice: Subject to any disclaimer, the term of this patent is extended or adjusted under 35 U.S.C. 154(b) by 1034 days.

(21) Appl. No.: 15/999,337

(22) PCT Filed: Feb. 17, 2017

(86) PCT No.: PCT/CN2017/073890
§ 371 (c)(1),
(2) Date: Aug. 17, 2018

(87) PCT Pub. No.: WO2017/140256
PCT Pub. Date: Aug. 24, 2017

(65) Prior Publication Data
US 2019/0038669 A1 Feb. 7, 2019

(30) Foreign Application Priority Data
Feb. 19, 2016 (WO) ................. PCT/CN2016/074146

(51) Int. Cl.
*A61K 39/395* (2006.01)
*A61K 35/17* (2015.01)
*C07K 16/30* (2006.01)
*C07K 14/705* (2006.01)
*C07K 16/44* (2006.01)
*G01N 33/574* (2006.01)
*G01N 33/68* (2006.01)
*C07K 14/725* (2006.01)
*A61P 1/18* (2006.01)
*A61P 35/00* (2006.01)
*C12N 15/62* (2006.01)
*A61K 39/00* (2006.01)

(52) U.S. Cl.
CPC ............ *A61K 35/17* (2013.01); *A61K 39/395* (2013.01); *A61P 1/18* (2018.01); *A61P 35/00* (2018.01); *C07K 14/7051* (2013.01); *C07K 14/70517* (2013.01); *C07K 14/70521* (2013.01); *C07K 16/30* (2013.01); *C07K 16/44* (2013.01); *C12N 15/62* (2013.01); *G01N 33/574* (2013.01); *G01N 33/57484* (2013.01); *G01N 33/6893* (2013.01); *A61K 2039/505* (2013.01); *C07K 2317/76* (2013.01); *C07K 2319/00* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| 4,816,567 | A | 3/1989 | Cabilly et al. |
| 8,957,188 | B2 | 2/2015 | Gildersleeve et al. |
| 2006/0292643 | A1 | 12/2006 | Goletz et al. |
| 2009/0324617 | A1 | 12/2009 | Satomaa et al. |
| 2010/0254898 | A1 | 10/2010 | Gildersleeve et al. |
| 2010/0254971 | A1 | 10/2010 | Dotan et al. |
| 2012/0040375 | A1 | 2/2012 | Nishimura et al. |
| 2013/0045543 | A1 | 2/2013 | Nishimura et al. |
| 2017/0267777 | A1 | 9/2017 | Wang |

FOREIGN PATENT DOCUMENTS

| CN | 102178686 A | 9/2011 |
| CN | 102372773 A | 3/2012 |
| CN | 104198707 A | 12/2014 |
| CN | 104267185 A | 1/2015 |
| CN | 105177031 A | 12/2015 |
| CN | 105246912 A | 1/2016 |
| EP | 0390115 A1 | 10/1990 |
| EP | 0407586 A1 | 1/1991 |
| EP | 0404097 B1 | 9/1996 |
| WO | 1993/011161 A1 | 6/1993 |
| WO | 2008/055242 A2 | 5/2008 |
| WO | 2011/012309 A1 | 2/2011 |
| WO | 2011/054359 A2 | 5/2011 |
| WO | 2014/159244 A2 | 10/2014 |
| WO | 2016/026456 A1 | 2/2016 |

OTHER PUBLICATIONS

Apantaku et al. (Breast cancer diagnosis and screening, American Family Physician 2000) (Year: 2000).*
Martin et al (Journal of the National Cancer Institute, vol. 92, No. 14: pp. 1126-1135, Jul. 19, 2000) (Year: 2000).*
Padlan (Advances in Protein Chemistry, 1996, 49:57-133) (Year: 1996).*

(Continued)

*Primary Examiner* — Meera Natarajan
(74) *Attorney, Agent, or Firm* — Morrison & Foerster LLP

(57) ABSTRACT

It provides antibodies and chimeric antigen receptors (CARs) that specifically bind to an epitope containing N-acetyl-glucosamine and/or N-acetyl-galactosamine, e.g., expressed by a cancer cell or an inflammatory cell. Also provided are compositions including these antibodies and/or CARs, as well as polynucleotides, vectors, host cells, methods, and kits related thereto. Further provided are methods and kits for treating or preventing cancer in an individual by administering to the individual an antibody that specifically binds to an epitope containing N-acetylglucosamine or N-acetyl-galactosamine, or a T cell comprising a CAR that specifically binds to an epitope containing N-acetylglucosamine or N-acetyl-galactosamine, optionally in combination with another anti-cancer agent.

18 Claims, 15 Drawing Sheets

Specification includes a Sequence Listing.

(56) References Cited

OTHER PUBLICATIONS

Berglund et al, Protein Science, 2008, 17:606-613 (Year: 2008).*
Corada (Blood, 2001; 97:1679-84) (Year: 2001).*
Kulkarni-Kale et al. Nucleic Acid Research, 2005, 33:W168-W171 (Year: 2005).*
Almagro & Fransson, Frontiers in Bioscience 2008; 13:1619-33 (Year: 2008).*
De Genst et al., Developmental and Comparative Immunology, 2006, 30:187-98 (Year: 2006).*
Ward et al. (Nature, 1989, 341:544-546) (Year: 1989).*
Barthelemy et al. (Journal of Biological Chemistry, 2008, 283:3639-3654) (Year: 2008).*
Choi et al., 2011, Molecular BioSystems, 2011, 7:3327-334 (Year: 2011).*
Griffiths et al. (The EMBO Journal, 1993, 12:725-734) (Year: 1993).*
Klimka et al., British Journal of Cancer, 2000, 83:252-260 (Year: 2000).*
Beiboer et al. (Journal of Molecular Biology, 2000, 296:833-849) (Year: 2000).*
Almagro et al., "Humanization of Antibodies", Frontiers in Bio-Science, vol. 13, 2008, pp. 1619-1633.
Barczak et al., "Universal Real-Time PCR-Based Assay for Lentiviral Titration", Molecular Biotechnology, vol. 57, 2015, pp. 195-200.
Barthelemy et al., "Comprehensive Analysis of the Factors Contributing to the Stability and Solubility of Autonomous Human VH Domains", The Journal of Biological Chemistry, vol. 283, No. 6, Feb. 8, 2008, pp. 3639-3654.
Beiboer et al., "Guided Selection of a Pan Carcinoma Specific Antibody Reveals Similar Binding Characteristics yet Structural Divergence Between the Original Murine Antibody and its Human Equivalent", Journal of Molecular Biology, vol. 296, 2000, pp. 833-849.
Berglund et al., "The Epitope Space of the Human Proteome", Protein Science, vol. 17, 2008, pp. 606-613.
Boerner et al., "Production of Antigen-Specific Human Monoclonal Antibodies from in Vitro-Primed Human Splenocytes1", The Journal of Immunology, vol. 147, No. 1, Jul. 1, 1991, pp. 86-95.
Brooks et al., "Expression of Alpha-GalNAc Glycoproteins by Breast Cancers", British Journal of Cancer, vol. 71, 1995, pp. 1033-1038.
Choi et al., "Predicting Antibody Complementarity Determining Region Structures without Classification", Molecular BioSystems, vol. 7, 2011, pp. 3327-3334.
Chothia et al., "Canonical Structures for the Hypervariable Regions of Immunoglobulins", Journal of Molecular Biology, vol. 196, 1987, pp. 901-917.
Clackson et al., "Making Antibody Fragments using Phage Display Libraries", Nature, vol. 352, Aug. 15, 1991, pp. 624-628.
Comer et al., "Characterization of a Mouse Monoclonal Antibody Specific for O-Linked N-Acetylglucosamine", Analytical Biochemistry, vol. 293, 2001, pp. 169-177.
Corada et al., "Monoclonal Antibodies Directed to Different Regions of Vascular Endothelial Cadherin Extracellular Domain Affect Adhesion and Clustering of the Protein and Modulate Endothelial Permeability", Blood, vol. 97, No. 6, Mar. 15, 2001, pp. 1679-1684.
Dai et al., "Chimeric Antigen Receptors Modified T-Cells for Cancer Therapy", Journal of the National Cancer Institute, vol. 108, No. 7, 2016, pp. 1-14.
Danielczyk et al., "PankoMab: A Potent New Generation Anti-Tumour MUC1 Antibody", Cancer Immunol Immunother, vol. 55, 2006, pp. 1337-1347.
De Genst et al., "Antibody Repertoire Development in Camelids", Developmental & Comparative Immunology, vol. 30, 2006, pp. 187-198.
Extended European Search Report (includes Supplementary European Search Report and Search Opinion) received for European Patent Application No. 15833676.8, dated Dec. 22, 2017, 10 pages.
Fan et al., "A New Tumor Marker: Mu-GlcNAc", Labeled Immunoassays and Clinical Medicine, vol. 21, No. 5, Oct. 2014, pp. 514-515. (English Abstract Submitted).
Gerngross, Tillman U., "Advances in the Production of Human Therapeutic Proteins in Yeasts and Filamentous Fungi", Nature Biotechnology, vol. 22, No. 11, Nov. 2004, pp. 1409-1414.
Graham et al., "Characteristics of a Human Cell Line Transformed by DNA from Human Adenovirus Type 5", Journal of General Virology, vol. 36, 1977, pp. 59-72.
Griffiths et al., "Human Anti-Self Antibodies with High Specificity from Phage Display Libraries", The EMBO Journal vol. 12, No. 2, 1993, pp. 725-734.
Holliger et al., ""Diabodies": Small Bivalent and Bispecific Antibody Fragments", Proceedings of the National Academy of Sciences, vol. 90, Jul. 1993, pp. 6444-6448.
International Preliminary Report on Patentability received for PCT Patent Application No. PCT/CN2014/085027, dated Mar. 9, 2017, 7 pages.
International Preliminary Report on Patentability received for PCT Patent Application No. PCT/CN2015/087717, dated Mar. 9, 2017, 8 pages.
International Preliminary Report on Patentability received for PCT Patent Application No. PCT/CN2016/074146, dated Aug. 30, 2018, 7 pages.
International Preliminary Report on Patentability received for PCT Patent Application No. PCT/CN2017/073890, dated Aug. 30, 2018, 7 pages.
International Search Report and Written Opinion received for PCT Patent Application No. PCT/CN2014/085027, dated May 28, 2015, 13 pages.
International Search Report and Written Opinion received for PCT Patent Application No. PCT/CN2015/087717, dated Nov. 17, 2015, 13 pages.
International Search Report and Written Opinion received for PCT Patent Application No. PCT/CN2016/074146, dated Sep. 28, 2016, 12 pages.
International Search Report and Written Opinion received for PCT Patent Application No. PCT/CN2017/073890, dated May 9, 2017, 12 pages.
Ito et al., "Monoclonal IgM in Two Patients with Motor Neuron Disease Bind to the Carbohydrate Antigens Gal(β1-3)GalNAc and Gal(β1-3)GlcNAc", Journal of Neuroimmunology, vol. 19, 1988, pp. 245-253.
Jakobovits et al., "Analysis of Homozygous Mutant Chimeric Mice: Deletion of the Immunoglobulin Heavy-Chain Joining Region Blocks B-Cell Development and Antibody Production", Proceedings of the National Academy of Sciences, vol. 90, Mar. 1993, pp. 2551-2555.
Jansson et al., "The Human Repertoire of Antibody Specificities against Thomsen-Friedenreich and Tn-Carcinoma-Associated Antigens as defined by Human Monoclonal Antibodies", Cancer Immunology Immunotherapy, vol. 34, 1992, pp. 294-298.
Jones et al., "Replacing the Complementarity-Determining Regions in a Human Antibody with those from a Mouse", Nature, vol. 321, May 29, 1986, pp. 522-525.
Kipriyanov et al., "Generation and Production of Engineered Antibodies", Molecular Biotechnology, vol. 26, 2004, pp. 39-60.
Klimka et al., "Human Anti-CD30 Recombinant Antibodies by Guided Phage Antibody Selection using Cell Panning", British Journal of Cancer, 83, No. 2, 2000, pp. 252-260.
Köhler et al., "Continuous Cultures of Fused Cells Secreting Antibody of Predefined Specificity", Nature, vol. 256, Aug. 7, 1975, pp. 495-497.
Kulkarni-Kale et al., "CEP: A Conformational Epitope Prediction Server", Nucleic Acids Research, vol. 33, 2005, pp. W168-W171.
Lonberg et al., "Antigen-Specific Human Antibodies from Mice Comprising Four Distinct Genetic Modifications", Nature, vol. 368, Apr. 28, 1994, pp. 856-859.
Maher et al., "Human T-Lymphocyte Cytotoxicity and Proliferation Directed by a Single Chimeric TCRζ/CD28 Receptor", Nature Biotechnology, vol. 20, Jan. 2002, pp. 70-75.
Moremen et al., "Vertebrate Protein Glycosylation: Diversity, Synthesis and Function", Nature Reviews Molecular Cell Biology, vol. 13, No. 7, 2012, pp. 448-462.

(56) References Cited

OTHER PUBLICATIONS

Morrison et al., "Chimeric Human Antibody Molecules: Mouse Antigen-Binding Domains with Human Constant Region Domains", Proc. Nat'l Acad. Sci, vol. 81, Nov. 1984, pp. 6851-6855.
Non-Final Office Action received for U.S. Appl. No. 15/505,064, dated May 13, 2019, 29 pages.
Office Action received for European Patent Application No. 15833676.8, dated Jan. 14, 2019, 5 pages.
Padlan, Eduardo A., "X-Ray Crystallography of Antibodies", Advances in Protein Chemistry, vol. 49, 1996, pp. 57-133.
Plückthun, A., "Antibodies from *Escherichia coli*", Chapter 11, The Pharmacology of Monoclonal Antibodies, 1994, pp. 269-315.
Presta, Leonard G., "Antibody Engineering", Current Opinion in Structural Biology, vol. 2, 1992, pp. 593-596.
Restriction Requirement received for U.S. Appl. No. 15/505,064, dated Dec. 13, 2018, 10 pages.
Richmond et al., "Mouse Xenograft Models vs GEM Models for Human Cancer Therapeutics", Disease Models & Mechanisms, vol. 1, 2008, pp. 78-82.
Riechmann et al., "Reshaping Human Antibodies for Therapy", Nature, vol. 332, Mar. 24, 1988, pp. 323-327.
Ryuko et al., "Characterization of a New MUC1 Monoclonal Antibody (VU-2-G7) Directed to the Glycosylated PDTR Sequence of MUC1", Tumor Biology, vol. 21, 2000, pp. 197-210.
Savoldo et al., "CD28 Costimulation Improves Expansion and Persistence of Chimeric Antigen Receptor-Modified T Cells in Lymphoma Patients", The Journal of Clinical Investigation, vol. 121, No. 5, May 2011, pp. 1822-1826.
Seow et al., "Novel Anti-Glycan Antibodies Related to Inflammatory Bowel Disease Diagnosis and Phenotype", The American Journal of Gastroenterology, vol. 104, Jun. 2009, pp. 1426-1434.
Smorodin et al., "The Characterization of IgG Antibodies to GaINAc Beta-Terminated Glycans of Gastric Cancer Survivors", Experimental Oncology, vol. 36, No. 1, Mar. 2014, pp. 38-43.
Tsubokawa et al., "A Monoclonal Antibody, PGM34, against 6-Sulfated Blood-Group H Type 2 Antigen, on the Carbohydrate Moiety of Mucin", FEBS Journal, vol. 274, 2007, pp. 1833-1848.
Urlaub et al., "Isolation of Chinese Hamster Cell Mutants Deficient in Dihydrofolate Reductase Activity", Proc. Natl. Acad. Sci., vol. 77, No. 7, Jul. 1980, pp. 4216-4220.
Ward et al., "Binding Activities of a Repertoire of Single Immunoglobulin Variable Domains Secreted from *Escherichia coli*", Nature, vol. 341, Oct. 12, 1989, pp. 544-546.
Zhang et al., "Protein O-GlcNAcylation and Cancer", Tumor, vol. 33, No. 11, 2013, pp. 1027-1032. (English Abstract Submitted).

\* cited by examiner

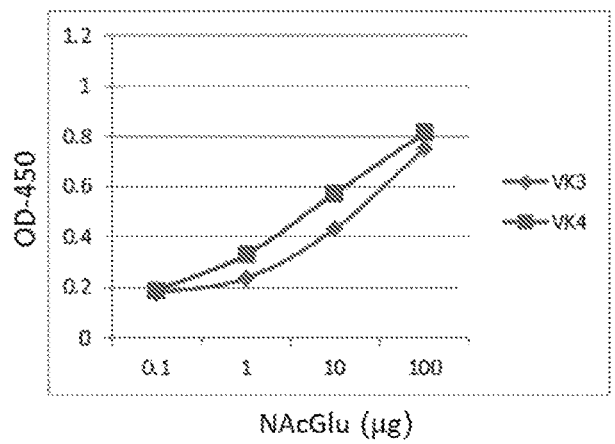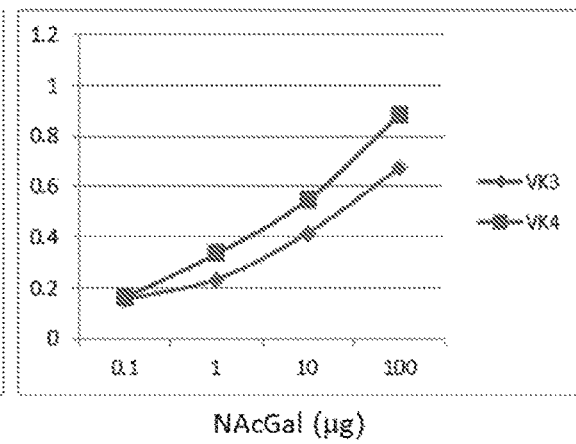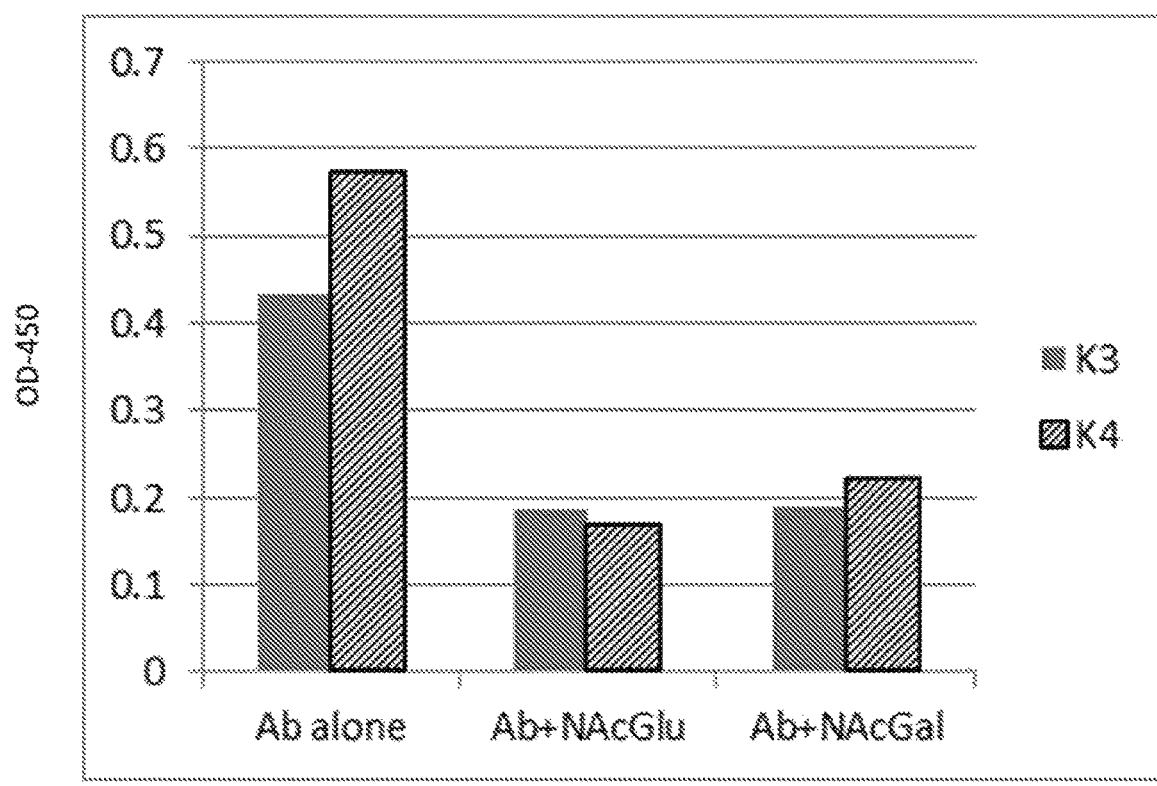
FIG. 2

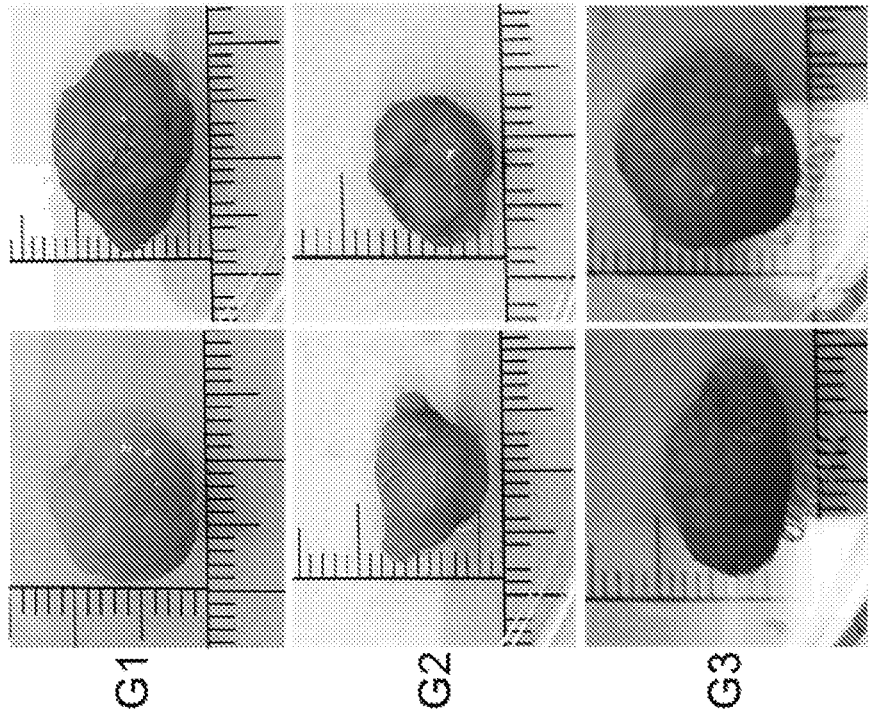
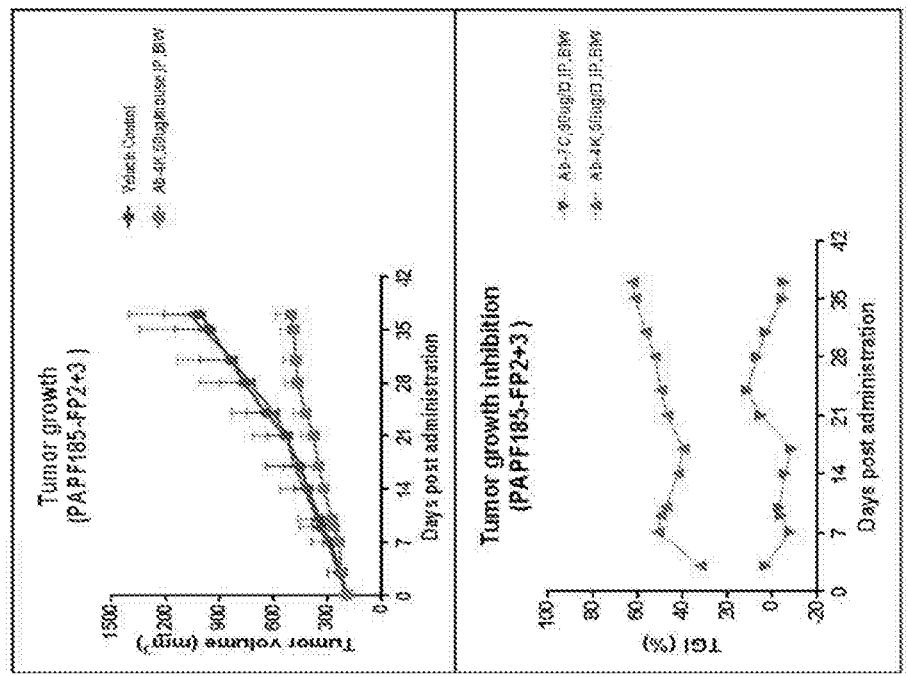
FIG. 8A
FIG. 8B
FIG. 8C

ANTIBODIES AGAINST N-ACETYLGLUCOSAMINE AND N-ACETYL-GALACTOSAMINE

CROSS-REFERENCE TO RELATED APPLICATIONS

This application is a U.S. National Phase patent application of International Patent Application Serial No. PCT/CN2017/073890, filed Feb. 17, 2017, which claims the priority benefit of International Patent Application Serial No. PCT/CN2016/074146, filed Feb. 19, 2016, each of which is incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735182000300SEQLIST.TXT, date recorded: Aug. 16, 2018, size: 31 KB).

FIELD

This invention relates to antibodies that specifically bind N-acetylglucosamine and/or N-acetyl-galactosamine, as well as compositions, polynucleotides, vectors, host cells, methods of production, methods of use, and kits related thereto.

BACKGROUND

Cancer is one of the most challenging disorders to treat in modern medicine for several reasons. Since cancer arises from the abnormal behavior of one's own cells, distinguishing cancer cells from normal cells within a patient is a difficult problem. Often the body's own immune system has difficulty identifying and eliminating cancerous cells. In addition, "cancer" refers to a constellation of individual disorders, i.e., types and subtypes of cancer. Many different cell types can become cancerous through many different mechanisms, resulting in a tremendous phenotypic variety in the types of cancer cells that may arise. This diversity is highly problematic for cancer treatment because different types of cancer cells may have different identifying properties for diagnosis, or they may possess different therapeutic weaknesses or resistant properties. This problem makes it difficult to come up with ways to diagnose, treat, and/or prevent multiple types of cancer through a single therapeutic strategy or agent. Even though oncology has advanced tremendously in the last decade, there is still a need to identify new biomarkers specific to cancer cells, particularly biomarkers that characterize multiple types of cancer but not normal tissues.

Cell surface molecules are highly important for cancer cells. These molecules are critically involved in cell-cell interactions, which are important for many cancer cell behaviors, including cell invasion, metastasis, evasion of the immune system, and responses to therapeutic agents. Cancer cells are known to express many cell surface proteins differently from normal cells. However, many cell surface proteins are modified by the addition of saccharides (e.g., N-acetylglucosamine or N-acetyl-galactosamine), a process termed protein glycosylation. How specific cell surface proteins are modified by the addition of saccharides, which saccharides may be found on which cell surface proteins, and how patterns of glycosylation change during different types or phases of carcinogenesis are all problems that are just beginning to be explored (for a review, see Moremen, K. W., et al. (2012) *Nat. Rev. Mol. Cell Biol.* 13(7):448-62). This diversity in glycosylation increases the complexity of cancer cell recognition by surface biomarkers.

Therefore, there remains a need for new biomarkers and therapeutic agents useful in the diagnosis, treatment, and prevention of cancer, particularly for biomarkers and agents that target cancer-specific patterns of glycosylation. In particular, there remains a need for improved diagnostic and/or therapeutic agents that specifically bind to one or more saccharides (e.g., N-acetylglucosamine and/or N-acetyl-galactosamine), which may be useful, inter alia, for the treatment of cancer, inflammatory, and/or autoimmune diseases.

All references cited herein, including patent applications, patent publications, and UniProtKB/Swiss-Prot Accession numbers are herein incorporated by reference in their entirety, as if each individual reference were specifically and individually indicated to be incorporated by reference

BRIEF SUMMARY

To meet the demand for new biomarkers and therapeutic agents useful in the diagnosis, treatment, and prevention of multiple types of cancer, disclosed herein are monoclonal antibodies that specifically bind N-acetylglucosamine or N-acetyl-galactosamine (e.g., expressed by a cancer cell or an inflammatory cell), as well as compositions, polynucleotides, vectors, host cells, methods of production, and kits related thereto. Further disclosed are methods of treating or preventing cancer in an individual by administering antibodies that specifically bind N-acetylglucosamine or N-acetyl-galactosamine expressed on a cell surface of a cancer cell, and methods of diagnosing cancer using antibodies that specifically bind N-acetylglucosamine or N-acetyl-galactosamine. These compositions and methods are based in part on the surprising discovery that human cancer cells representing many different types of cancer express higher levels of N-acetylglucosamine and/or N-acetyl-galactosamine than normal human tissues. Moreover, the present disclosure demonstrates the surprising result that antibodies that specifically bind N-acetylglucosamine and/or N-acetyl-galactosamine expressed on a cell surface of a cancer cell are highly potent and effective in reducing the growth rate of several diverse types of cancer cells, both in vitro and in vivo. Additionally, the present application describes the unexpected finding that antibodies that specifically bind N-acetylglucosamine or N-acetyl-galactosamine may be used as an effective preventative and treatment for gastrointestinal diseases, such as viral infection, inflammatory bowel disease, and hemorrhoids, and rheumatoid arthritis.

In one aspect, provided herein are antibodies that specifically bind to an epitope comprising N-acetylglucosamine and/or N-acetyl-galactosamine. Also provided are compositions comprising these antibodies, as well as polynucleotides, vectors, host cells, and methods useful in the production thereof. Further provided are methods and kits useful for treating or preventing cancer in an individual by administering to the individual an antibody that specifically binds to an epitope comprising N-acetylglucosamine or N-acetyl-galactosamine, optionally in combination with another anti-cancer agent. Further provided are methods and kits useful for treating or preventing gastrointestinal disease in an individual by administering to the individual an antibody that specifically binds to an epitope comprising N-acetylglucosamine or N-acetyl-galactosamine. Yet further provided are methods and kits useful for detecting the presence of cancer cells in an individual by obtaining a biological sample from an individual, contacting the biological sample with an antibody that specifically binds to an epitope comprising N-acetylglucosamine and/or N-acetyl-galactosamine, and detecting the amount of antibody binding to the biological sample, where antibody binding indicates the presence of cancer cells in the individual.

In certain aspects, the present disclosure provides an isolated monoclonal antibody that specifically binds to an epitope comprising N-acetylglucosamine or N-acetyl-galactosamine, wherein the antibody comprises a light chain variable region comprising an HVR-L1 sequence of SEQ ID NO: 5, an HVR-L2 sequence of FTSX$_1$LX$_2$S (SEQ ID NO: 25), and an HVR-L3 sequence of SEQ ID NO: 9, wherein X$_1$ is T or S and X$_2$ is Q or E. In certain embodiments, the HVR-L2 sequence comprises the amino acid sequence of SEQ ID NO: 7. In certain embodiments, the antibody comprises a light chain variable region comprising the amino acid sequence of SEQ ID NO: 13. In certain embodiments, the antibody comprises a light chain comprising the amino acid sequence of SEQ ID NO: 16. In certain embodiments, the HVR-L2 sequence comprises the amino acid sequence of SEQ ID NO: 8. In certain embodiments, the antibody comprises a light chain variable region comprising the amino acid sequence of SEQ ID NO: 14. In certain embodiments, the antibody comprises a light chain comprising the amino acid sequence of SEQ ID NO: 17. In certain embodiments, the antibody further comprises a heavy chain variable region comprising an HVR-H1 sequence of SEQ ID NO: 1, an HVR-H2 sequence of SEQ ID NO: 2, and an HVR-H3 sequence of SEQ ID NO: 3. In certain embodiments, the antibody comprises a heavy chain variable region comprising the amino acid sequence of SEQ ID NO: 10. In certain embodiments, the antibody comprises a heavy chain comprising the amino acid sequence of SEQ ID NO: 11. In some embodiments, the antibody comprises a heavy chain variable region comprising three HVRs of SEQ ID NO: 10 and/or a light chain variable region comprising three HVRs of SEQ ID NO: 12. In some embodiments, the antibody comprises a heavy chain variable region comprising three HVRs of SEQ ID NO: 10 and/or a light chain variable region comprising three HVRs of SEQ ID NO: 13. In some embodiments, the antibody comprises a heavy chain variable region comprising three HVRs of SEQ ID NO: 10 and/or a light chain variable region comprising three HVRs of SEQ ID NO: 14. In some embodiments, the antibody comprises a heavy chain variable region comprising three HVRs of SEQ ID NO: 10 and/or a light chain variable region comprising three HVRs of SEQ ID NO: 19. In some embodiments, the antibody comprises a heavy chain variable region comprising three HVRs of SEQ ID NO: 10 and/or a light chain variable region comprising three HVRs of SEQ ID NO: 23. In some embodiments, the antibody comprises a heavy chain variable region comprising the amino acid sequence of SEQ ID NO: 10 and/or a light chain variable region comprising the amino acid sequence of SEQ ID NO: 12. In some embodiments, the antibody comprises a heavy chain variable region comprising the amino acid sequence of SEQ ID NO: 10 and/or a light chain variable region comprising the amino acid sequence of SEQ ID NO: 13. In some embodiments, the antibody comprises a heavy chain variable region comprising the amino acid sequence of SEQ ID NO: 10 and/or a light chain variable region comprising the amino acid sequence of SEQ ID NO: 14. In some embodiments, the antibody comprises a heavy chain vari-able region comprising the amino acid sequence of SEQ ID NO: 10 and/or a light chain variable region comprising the amino acid sequence of SEQ ID NO: 19. In some embodiments, the antibody comprises a heavy chain variable region comprising the amino acid sequence of SEQ ID NO: 10 and/or a light chain variable region comprising the amino acid sequence of SEQ ID NO: 23. In certain embodiments that may be combined with any of the preceding embodiments, the antibody is an antibody fragment. In certain embodiments, the antibody is a Fab fragment, scFv, minibody, diabody, scFv multimer, or bispecific antibody fragment. In certain embodiments, the antibody is a humanized antibody. In certain embodiments, the antibody is a human antibody. In certain embodiments, the antibody is a chimeric antibody. In certain embodiments, the antibody specifically binds to an epitope comprising N-acetylglucosamine and an epitope comprising N-acetyl-galactosamine. In certain embodiments that may be combined with any of the preceding embodiments, the epitope is expressed by a cancer cell or an inflammatory cell the epitope is expressed on a cell surface of the cancer cell. In certain embodiments, the epitope is expressed in the cancer cell. In certain embodiments that may be combined with any of the preceding embodiments, the cancer cell is selected from a pancreatic adenocarcinoma cell, a colon adenocarcinoma cell, a rectal adenocarcinoma cell, an esophageal adenocarcinoma cell, a leukemia cell, an adenoid carcinoma cell, a fibrosarcoma cell, a duodenal adenocarcinoma cell, a glioma cell, a hepatocarcinoma cell, a lung cancer cell, a breast cancer cell, a glioblastoma cell, an ovarian carcinoma cell, and a cervical adenocarcinoma cell. In certain embodiments, the pancreatic adenocarcinoma cell is a pancreatic ductal adenocarcinoma cell. In certain embodiments, the binding of the antibody to the epitope inhibits growth of the cancer cell. In certain embodiments, the lung cancer cell is a small cell lung cancer cell, a lung squamous cell carcinoma cell, or a lung adenocarcinoma cell. In certain embodiments, the inflammatory cell is an intestinal inflammatory cell of colitis, inflammatory bowel disease, or gastroenteritis, and the epitope is expressed on a cell surface of the inflammatory cell. In certain embodiments, the inflammatory cell is an inflammatory cell of rheumatoid arthritis, and the epitope is expressed on a cell surface of the inflammatory cell. In certain embodiments, the rheumatoid arthritis is induced by collagen.

In further aspects, the present disclosure provides an isolated polynucleotide comprising a nucleic acid sequence encoding an antibody according to any of the above embodiments. In still further aspects, the present disclosure provides a vector comprising a nucleic acid sequence encoding an antibody according to any of the above embodiments. In yet still further aspects, the present disclosure provides an isolated host cell comprising an isolated polynucleotide comprising a nucleic acid sequence encoding an antibody according to any of the above embodiments or a vector comprising a nucleic acid sequence encoding an antibody according to any of the above embodiments. In yet still further aspects, the present disclosure provides an isolated host cell comprising an isolated polynucleotide comprising a nucleic acid sequence encoding an antibody according to any of the above embodiments or a vector comprising a nucleic acid sequence encoding an antibody according to any of the above embodiments. In yet still further aspects, the present disclosure provides methods of producing an antibody, comprising culturing a host cell according to any of the above embodiments, that produces the antibody according to any of the above embodiments, and recovering the antibody from the cell culture. In yet still further aspects, the present disclosure provides an antibody produced by the methods of producing an antibody according to any of the above embodiments. In other aspects, the present disclosure provides a composition comprising an antibody according to any of the above embodiments, and a pharmaceutically acceptable carrier.

In other aspects, the present disclosure provides a method for treating or preventing cancer in an individual, comprising administering to the individual an effective amount of a composition comprising an antibody according to any of the above embodiments. In other aspects, the present disclosure provides a method for treating or preventing cancer in an individual, comprising administering to the individual an amount of an antibody according to any of the above embodiments, and an amount of another anti-cancer agent, where the antibody and the anti-cancer agent in conjunction provide effective treatment or prevention of cancer in the individual. In some embodiments, the individual has, or has been diagnosed with, cancer. In certain embodiments, the cancer is selected from pancreatic cancer, colon cancer, rectal cancer, esophageal cancer, leukemia, adenocarcinoma, fibrosarcoma, duodenal adenocarcinoma, brain cancer, liver cancer, lung cancer, breast cancer, ovarian cancer, and cervical cancer. In certain embodiments, the individual is a human. In certain embodiments, the individual is a non-human animal. In certain embodiments, the anti-cancer agent is a chemotherapeutic agent.

In other aspects, the present disclosure provides a method for detecting cancer cells in an individual, comprising contacting a biological sample from the individual with an antibody according to any of the above embodiments and detecting binding of the antibody to the biological sample, where binding of the antibody to the sample may indicate the presence of cancer cells in the individual. In certain embodiments, the method further comprises comparing the amount of antibody binding detected with an amount of antibody binding to a control sample. In certain embodiments that may be combined with any of the preceding embodiments, the binding of the antibody to the biological sample is detected by an assay selected from an ELISA assay, a flow cytometry assay, an immunohistochemistry assay, an immunofluorescence assay, a circulating tumor cells assay, and an immune-colloidal gold assay. In certain embodiments that may be combined with any of the preceding embodiments, the biological sample is selected from blood, serum, urine, feces, milk, semen, saliva, chest fluid, abdominal fluid, cerebrospinal fluid, sputum, and any other body fluid or secretion. In certain embodiments, the individual is a human. In certain embodiments, the individual is a non-human animal. In certain embodiments that may be combined with any of the preceding embodiments, the cancer cells are selected from pancreatic cancer cells, leukemia cells, adenocarcinoma cells, fibrosarcoma cells, lung cancer cells, liver cancer cells, breast cancer cells, colon or colorectal cancer cells, esophageal cancer cells, stomach cancer cells, endometrial cancer cells, cervical cancer cells, thyroid cancer cells, brain cancer cells, and lymphoma cells.

In other aspects, the present disclosure provides a method for treating or preventing gastrointestinal disease in an individual comprising administering to the individual an effective amount of an antibody according to any of the above embodiments. In some embodiments, the individual has, or has been diagnosed with, a gastrointestinal disease of the present disclosure. In certain embodiments, the individual has inflammatory bowel disease. In certain embodiments, the individual has Crohn's disease. In certain embodiments, the individual has ulcerative colitis. In certain embodiments, the individual has acute infectious gastroenteritis. In certain embodiments, the individual has a hemorrhoid. In certain embodiments, the individual has a gastrointestinal disease caused by a viral infection. In certain embodiments, the viral infection is a rotaviral infection or a porcine epidemic diarrhea viral infection. In certain embodiments that may be combined with any of the preceding embodiments, the individual is a human. In certain embodiments that may be combined with any of the preceding embodiments, the individual is a non-human animal. In certain embodiments that may be combined with any of the preceding embodiments, the antibody is administered intravenously, intramuscularly, subcutaneously, topically, orally, transdermally, intraperitoneally, intraorbitally, by implantation, by inhalation, intrathecally, intraventricularly, or intranasally.

In other aspects, the present disclosure provides a method for treating or preventing rheumatoid arthritis in an individual comprising administering to the individual an effective amount of an antibody that specifically binds to an epitope comprising N-acetylglucosamine or N-acetyl-galactosamine. In some embodiments, the individual has, or has been diagnosed with, rheumatoid arthritis. In some embodiments, the epitope is expressed by an inflammatory cell. In certain embodiments, the antibody specifically binds to an epitope comprising N-acetylglucosamine and an epitope comprising N-acetyl-galactosamine. In certain embodiments, the antibody is an antibody fragment. In certain embodiments, the antibody is a Fab fragment, scFv, minibody, diabody, scFv multimer, or bispecific antibody fragment. In certain embodiments, the antibody is a humanized antibody. In certain embodiments, the antibody is a human antibody. In certain embodiments, the antibody is a chimeric antibody. In certain embodiments, the antibody comprises a heavy chain variable region comprising three HVRs from the amino acid sequence of SEQ ID NO:10, and a light chain variable region comprising three HVRs from an amino acid sequence selected from the group consisting of SEQ ID NOs: 12, 13, 14, 19, and 23. In some embodiments, the antibody comprises a heavy chain variable region comprising the amino acid sequence of SEQ ID NO: 10 and/or a light chain variable region comprising the amino acid sequence of SEQ ID NO: 12. In some embodiments, the antibody comprises a heavy chain variable region comprising the amino acid sequence of SEQ ID NO: 10 and/or a light chain variable region comprising the amino acid sequence of SEQ ID NO: 13. In some embodiments, the antibody comprises a heavy chain variable region comprising the amino acid sequence of SEQ ID NO: 10 and/or a light chain variable region comprising the amino acid sequence of SEQ ID NO: 14. In some embodiments, the antibody comprises a heavy chain variable region comprising the amino acid sequence of SEQ ID NO: 10 and/or a light chain variable region comprising the amino acid sequence of SEQ ID NO: 19. In some embodiments, the antibody comprises a heavy chain variable region comprising the amino acid sequence of SEQ ID NO: 10 and/or a light chain variable region comprising the amino acid sequence of SEQ ID NO: 23 In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 4, an HVR-L2 sequence of SEQ ID NO: 6, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:12. In certain embodiments, the antibody comprises a heavy chain comprising the amino acid sequence of SEQ ID NO:11, and a light chain comprising the amino acid sequence of SEQ ID NO:15. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 21, an HVR-L2 sequence of SEQ ID NO: 22, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:23. In certain embodiments, the antibody comprises a heavy chain comprising the amino acid sequence of SEQ ID NO:11, and a light chain comprising the amino acid sequence of SEQ ID NO:24. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 4, an HVR-L2 sequence of SEQ ID NO: 18, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:19. In certain embodiments, the antibody comprises a heavy chain comprising the amino acid sequence of SEQ ID NO:11, and a light chain comprising the amino acid sequence of SEQ ID NO:20. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 5, an HVR-L2 sequence of SEQ ID NO: 7, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:13. In certain embodiments, the antibody comprises a heavy chain comprising the amino acid sequence of SEQ ID NO:11, and a light chain comprising the amino acid sequence of SEQ ID NO:16. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 5, an HVR-L2 sequence of SEQ ID NO: 8, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:14. In certain embodiments, the antibody comprises a heavy chain comprising the amino acid sequence of SEQ ID NO:11, and a light chain comprising the amino acid sequence of SEQ ID NO:17. In certain embodiments that may be combined with any of the preceding embodiments, the individual is a human. In certain embodiments that may be combined with any of the preceding embodiments, the individual is a non-human animal. In certain embodiments that may be combined with any of the preceding embodiments, the antibody is administered intravenously, intramuscularly, subcutaneously, topically, orally, transdermally, intraperitoneally, intraorbitally, by implantation, by inhalation, intrathecally, intraventricularly, or intranasally.

In other aspects, the present disclosure provides a kit comprising a pharmaceutical composition comprising an antibody according to any of the above embodiments. In certain aspects, the kit further comprises instructions for administering an effective amount of the pharmaceutical composition to an individual for treating or preventing cancer. In some embodiments, the individual has, or has been diagnosed with, cancer. In certain aspects, the kit further comprises instructions for administering an effective amount of the pharmaceutical composition to an individual for treating or preventing gastrointestinal disease. In some embodiments, the individual has, or has been diagnosed with, gastrointestinal disease. In certain aspects, the kit further comprises instructions for administering an effective amount of the pharmaceutical composition to an individual for treating or preventing an autoimmune disease. In certain aspects, the kit further comprises instructions for detecting the presence of cancer cells in an individual. In certain aspects, the kit further comprises instructions for determining a level of N-acetylglucosamine or N-acetyl-galactosamine in a biological sample from an individual with cancer.

In other aspects, the present disclosure provides a kit comprising a pharmaceutical composition comprising an antibody that specifically binds to an epitope comprising N-acetylglucosamine or N-acetyl-galactosamine, wherein the epitope is expressed by an inflammatory cell; and instructions for administering an effective amount of the composition to an individual for treating or preventing rheumatoid arthritis. In some embodiments, the individual has, or has been diagnosed with, rheumatoid arthritis. In certain embodiments, the antibody specifically binds to an epitope comprising N-acetylglucosamine and an epitope comprising N-acetyl-galactosamine. In certain embodiments, the antibody is an antibody fragment. In certain embodiments, the antibody is a Fab fragment, scFv, minibody, diabody, scFv multimer, or bispecific antibody fragment. In certain embodiments, the antibody is a humanized antibody. In certain embodiments, the antibody is a human antibody. In certain embodiments, the antibody is a chimeric antibody. In certain embodiments, the antibody comprises a heavy chain variable region comprising three HVRs from the amino acid sequence of SEQ ID NO:10, and a light chain variable region comprising three HVRs from an amino acid sequence selected from the group consisting of SEQ ID NOs: 12, 13, 14, 19, and 23. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 4, an HVR-L2 sequence of SEQ ID NO: 6, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:12. In certain embodiments, the antibody comprises a heavy chain comprising the amino acid sequence of SEQ ID NO:11, and a light chain comprising the amino acid sequence of SEQ ID NO:15. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 21, an HVR-L2 sequence of SEQ ID NO: 22, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:23. In certain embodiments, the antibody comprises a heavy chain comprising the amino acid sequence of SEQ ID NO:11, and a light chain comprising the amino acid sequence of SEQ ID NO:24. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 4, an HVR-L2 sequence of SEQ ID NO: 18, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:19. In certain embodiments, the antibody comprises a heavy chain comprising the amino acid sequence of SEQ ID NO:11, and a light chain comprising the amino acid sequence of SEQ ID NO:20. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 5, an HVR-L2 sequence of SEQ ID NO: 7, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:13. In certain embodiments, the antibody comprises a heavy chain comprising the amino acid sequence of SEQ ID NO:11, and a light chain comprising the amino acid sequence of SEQ ID NO:16. In certain embodiments, the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3; and a light chain variable region comprising an HVR-L1 sequence of SEQ ID NO: 5, an HVR-L2 sequence of SEQ ID NO: 8, and an HVR-L3 sequence of SEQ ID NO: 9. In certain embodiments, the antibody comprises a heavy chain variable region comprising the amino acid sequence of SEQ ID NO:10, and a light chain variable region comprising the amino acid sequence of SEQ ID NO:14. In certain embodiments, the antibody comprises a heavy chain comprising the amino acid sequence of SEQ ID NO:11, and a light chain comprising the amino acid sequence of SEQ ID NO:17. In certain embodiments that may be combined with any of the preceding embodiments, the individual is a human. In certain embodiments that may be combined with any of the preceding embodiments, the individual is a non-human animal. In certain embodiments that may be combined with any of the preceding embodiments, the antibody is administered intravenously, intramuscularly, subcutaneously, topically, orally, transdermally, intraperitoneally, intraorbitally, by implantation, by inhalation, intrathecally, intraventricularly, or intranasally.

In other aspects, the present disclosure provides a chimeric antigen receptor (CAR) that comprises an antibody fragment comprising a light chain variable region comprising an HVR-L1 sequence of SEQ ID NO: 5, an HVR-L2 sequence of SEQ ID NO: 7, and an HVR-L3 sequence of SEQ ID NO: 9 and/or a heavy chain variable region comprising an HVR-H1 sequence of SEQ ID NO: 1, an HVR-H2 sequence of SEQ ID NO: 2, and an HVR-H3 sequence of SEQ ID NO: 3. In other aspects, the present disclosure provides a chimeric antigen receptor (CAR) that comprises an antibody fragment comprising a light chain variable region comprising an HVR-L1 sequence of SEQ ID NO: 5, an HVR-L2 sequence of SEQ ID NO: 8, and an HVR-L3 sequence of SEQ ID NO: 9 and/or a heavy chain variable region comprising an HVR-H1 sequence of SEQ ID NO: 1, an HVR-H2 sequence of SEQ ID NO: 2, and an HVR-H3 sequence of SEQ ID NO: 3. In other aspects, the present disclosure provides a chimeric antigen receptor (CAR) that specifically binds to an epitope comprising N-acetylglucosamine or N-acetyl-galactosamine, wherein the CAR comprises a light chain variable region comprising (a) an HVR-L1 sequence of SEQ ID NO: 4, an HVR-L2 sequence of SEQ ID NO: 6, and an HVR-L3 sequence of SEQ ID NO: 9, (b) an HVR-L1 sequence of SEQ ID NO: 21, an HVR-L2 sequence of SEQ ID NO: 22, and an HVR-L3 sequence of SEQ ID NO: 9, (c) an HVR-L1 sequence of SEQ ID NO: 4, an HVR-L2 sequence of SEQ ID NO: 18, and an HVR-L3 sequence of SEQ ID NO: 9, (d) an HVR-L1 sequence of SEQ ID NO: 5, an HVR-L2 sequence of SEQ ID NO: 7, and an HVR-L3 sequence of SEQ ID NO: 9, or (e) an HVR-L1 sequence of SEQ ID NO: 5, an HVR-L2 sequence of SEQ ID NO: 8, and an HVR-L3 sequence of SEQ ID NO: 9; and a heavy chain variable region comprising an HVR-H1 sequence of SEQ ID NO: 1, an HVR-H2 sequence of SEQ ID NO: 2, and an HVR-H3 sequence of SEQ ID NO: 3. In other aspects, the present disclosure provides a chimeric antigen receptor (CAR) that specifically binds to an epitope comprising N-acetylglucosamine or N-acetyl-galactosamine, wherein the CAR comprises a light chain variable region comprising an HVR-L1 sequence of SEQ ID NO: 5, an HVR-L2 sequence of $FTSX_1LX_2S$ (SEQ ID NO: 25), and an HVR-L3 sequence of SEQ ID NO: 9, wherein $X_1$ is T or S and $X_2$ is Q or E and a heavy chain variable region comprising an HVR-H1 sequence of SEQ ID NO: 1, an HVR-H2 sequence of SEQ ID NO: 2, and an HVR-H3 sequence of SEQ ID NO: 3. In some embodiments, the HVR-L2 sequence comprises the amino acid sequence of SEQ ID NO: 8. In some embodiments, the CAR comprises a light chain variable region comprising the amino acid sequence of SEQ ID NO: 14 or SEQ ID NO:26. In some embodiments, the HVR-L2 sequence comprises the amino acid sequence of SEQ ID NO: 7. In some embodiments, the CAR comprises a light chain variable region comprising the amino acid sequence of SEQ ID NO: 12, 13, 19, or 23. In some embodiments, the CAR comprises a light chain variable region comprising the amino acid sequence of SEQ ID NO: 13. In some embodiments of any of the above embodiments, the CAR comprises a heavy chain variable region comprising the amino acid sequence of SEQ ID NO: 10 or SEQ ID NO: 33. In some embodiments, the CAR comprises a light chain variable region comprising the amino acid sequence of SEQ ID NO: 14 or SEQ ID NO:26 and a heavy chain variable region comprising the amino acid sequence of SEQ ID NO: 10 or SEQ ID NO: 33. In some embodiments, the CAR comprises a light chain variable region comprising the amino acid sequence of SEQ ID NO: 12 and a heavy chain variable region comprising the amino acid sequence of SEQ ID NO: 10 or SEQ ID NO: 33. In some embodiments, the CAR comprises a light chain variable region comprising the amino acid sequence of SEQ ID NO: 23 and a heavy chain variable region comprising the amino acid sequence of SEQ ID NO: 10 or SEQ ID NO: 33. In some embodiments, the CAR comprises a light chain variable region comprising the amino acid sequence of SEQ ID NO: 19 and a heavy chain variable region comprising the amino acid sequence of SEQ ID NO: 10 or SEQ ID NO: 33. In some embodiments, the CAR comprises a light chain variable region comprising the amino acid sequence of SEQ ID NO: 13 and a heavy chain variable region comprising the amino acid sequence of SEQ ID NO: 10 or SEQ ID NO: 33. In some embodiments, the light chain variable region and the heavy chain variable region are humanized or human. In some embodiments, the CAR comprises a human CD3 zeta endodomain sequence. In some embodiments, the CAR further comprises a human CD28 endodomain sequence. In some embodiments, the CAR comprises, from N-terminus to C-terminus, the heavy chain variable region, a linker, the light chain variable region, a CD8 hinge region, a human CD28 endodomain, and a human CD3 zeta endodomain. In some embodiments, the CAR comprises the amino acid sequence of SEQ ID NO: 34. In some embodiments, the CAR specifically binds to an epitope comprising N-acetylglucosamine and an epitope comprising N-acetyl-galactosamine. In some embodiments, the epitope is expressed on a cell surface of a cancer cell. In some embodiments, the cancer cell is selected from the group consisting of a pancreatic adenocarcinoma cell, a colon adenocarcinoma cell, a rectal adenocarcinoma cell, an esophageal adenocarcinoma cell, a leukemia cell, an adenoid carcinoma cell, a fibrosarcoma cell, a duodenal adenocarcinoma cell, a glioma cell, a hepatocarcinoma cell, a lung cancer cell, a breast cancer cell, a glioblastoma cell, an ovarian carcinoma cell, and a cervical adenocarcinoma cell. In some embodiments, the pancreatic adenocarcinoma cell is a pancreatic ductal adenocarcinoma cell. In some embodiments, the CAR is expressed on a cell surface of a T cell, and wherein binding of the CAR to the epitope expressed on the cell surface of the cancer cell leads to killing of the cancer cell by the T cell.

In other aspects, the present disclosure provides an isolated polynucleotide comprising a nucleic acid sequence encoding the CAR according to any one of the above embodiments. In other aspects, the present disclosure provides a vector comprising a nucleic acid sequence encoding the CAR according to any one of the above embodiments. In some embodiments, the vector is a viral vector. In some embodiments, the vector is a lentiviral vector. In other aspects, the present disclosure provides an isolated T cell comprising the polynucleotide according to any one of the above embodiments or the vector according to any one of the above embodiments. In other aspects, the present disclosure provides an isolated T cell comprising the CAR according to any one of the above embodiments, wherein the CAR is expressed on a cell surface of the T cell. In some embodiments, the T cell is a human T cell.

In other aspects, the present disclosure provides a method for treating or preventing cancer in an individual, comprising administering to the individual an effective amount of a composition comprising the T cell according to any of the above embodiments. In some embodiments, the cancer is selected from the group consisting of pancreatic cancer, colorectal cancer, esophageal cancer, leukemia, adenocarcinoma, fibrosarcoma, duodenal adenocarcinoma, brain cancer, liver cancer, lung cancer, breast cancer, ovarian cancer, and cervical cancer. In some embodiments, the cancer is selected from the group consisting of pancreatic cancer, colorectal cancer, lung cancer, and brain cancer. In some embodiments, the individual is a human. In some embodiments, the method further comprises administering to the individual an amount of another anti-cancer agent, whereby the T cell and the anti-cancer agent in conjunction provide effective treatment or prevention of cancer in the individual. In some embodiments, the anti-cancer agent is a chemotherapeutic agent.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIGS. 1A & 1B show in vitro binding of humanized antibodies VK3 and VK4 to N-acetylglucosamine (NAcGlu; FIG. 1A) and N-acetyl-galactosamine (NAcGal; FIG. 1B).

FIG. 2 shows inhibition of antibody VK3 ("K3") and VK4 ("K4") binding to N-acetylglucosamine (10 µg) by pre-treatment with N-acetylglucosamine (NAcGlu) or N-acetyl-galactosamine (NAcGal), as compared to no pre-treatment (Ab alone).

FIG. 6A) or day 28 post-dosing (i.e., after 14 doses; FIG. 6B) of the rat collagen-induced arthritis model. Treatment groups are as described above for FIGS. 5A & 5B.

FIGS. 8A-8C show the effects of treatment with antibody VK4 ("K4") on tumor volume (FIG. 8A), tumor growth inhibition (TGI; FIG. 8B), and tumor size (images in FIG. 8C) in the PDX-P3 pancreatic cancer model, as compared to untreated controls or another antibody (7C).

FIG. 10B) in the PDX-P3 rectal cancer model, as compared to untreated controls.

DETAILED DESCRIPTION

Figure 3:
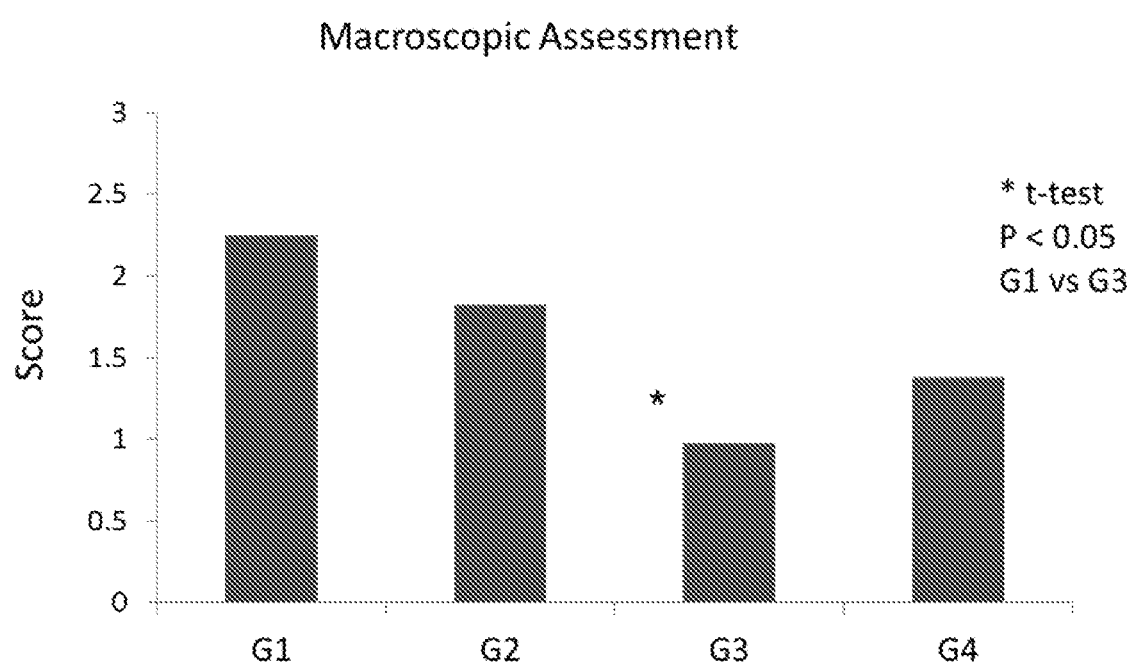
FIG. 3 shows the effect of humanized K3 (VK3) and K4 (VK4) antibody on intestinal morphology in a mouse IBD model induced by trinitrobenzenesulphonic acid (TNBS), as judged by macroscopic assessment conducted on day 7. Treatment groups include G1: untreated (n=5); G2: 200 µg Adalimumab/animal, intraperitoneal (IP) (n=5); G3: 5 µg VK3/animal, intraperitoneal (IP) (n=5); and G4: 5 µg VK4/animal, intraperitoneal (IP) (n=5). *indicates $p<0.05$ by t-test (comparisons were between the treatment group G3 and the untreated control group G1).

The present disclosure provides, inter alia, new antibodies that specifically bind N-acetylglucosamine and N-acetyl galactosamine. Multiple such antibodies are demonstrated herein to treat one or more symptoms of inflammation, cancer, and/or autoimmune disease in a variety of in vivo models. In particular, these antibodies were found to have increased efficacy as compared to existing antibodies, e.g., in mitigation of inflammation and ulceration in an inflammatory bowel disease (IBD) model, reduction of inflammation in a collagen-induced arthritis model, and inhibition of tumor growth in a pancreatic or rectal cancer model. In addition, these antibodies were demonstrated to bind to a number of human tumor cell lines representing a range of different cancer types. Variable domains of an antibody binding N-acetylglucosamine and N-acetyl galactosamine were also found to mediate cell killing of a wide range of tumor cell lines in the context of a chimeric antigen receptor expressed by human T cells.

I. General Techniques

The techniques described or referenced herein are well understood and employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); Harlow and Lane, eds. (1988) *Antibodies, A Laboratory Manual*, and *Animal Cell Culture* (R. I. Freshney, ed. (1987)); *Methods in Molecular Biology*, Humana Press; *Monoclonal Antibodies: A Practical Approach* (P. Shepherd and C. Dean, eds., Oxford University Press, 2000); and *Cancer: Principles and Practice of Oncology* (V. T. DeVita et al., eds., J.B. Lippincott Company, 1993).

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "inflammation" refers to the complex biological response of body tissues to harmful stimuli, such as pathogens, damaged cells, or irritants. The classical signs of acute inflammation include without limitation pain, heat, redness, swelling, and loss of function. Inflammation is a generic response, and therefore it is considered a mechanism of innate immunity. Inflammation can be classified as acute or chronic. Acute inflammation refers to the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

The term "inflammatory cells" refers to leukocytes (e.g., neutrophils, macrophages, monocytes, eosinophils, basophils, and lymphocytes) that normally reside in the blood and move into the inflamed tissue via extravasation to aid in inflammation. Some act as phagocytes, ingesting bacteria, viruses, and cellular debris. Others release enzymatic granules that damage pathogenic invaders. Leukocytes also release inflammatory mediators that develop and maintain the inflammatory response. In general, acute inflammation is mediated by granulocytes, whereas chronic inflammation is mediated by mononuclear cells such as monocytes and lymphocytes. In some embodiments, inflammatory cells may include lymphocytes, such as T- or B-cells.

The term "inflammatory bowel disease (IBD)" refers to the pathological state characterized by chronic inflammation of all or part of digestive tract. IBD primarily includes ulcerative colitis and Crohn's disease. Both usually involve severe diarrhea, pain, fatigue, and weight loss. Ulcerative colitis is a form of IBD that causes long-lasting inflammation and sores (ulcers) in large intestine (colon) and rectum. Crohn's disease is a form of IBD that causes inflammation of the digestive tract. In Crohn's disease, inflammation often spreads deep into affected tissues. The inflammation can involve different areas of the digestive tract such as the large intestine, small intestine or both. Collagenous colitis and lymphocytic colitis also are considered inflammatory bowel diseases but are usually regarded separately from classic inflammatory bowel disease.

The terms "cancer" and "cancer cells" refer to or describe the physiological condition in animals that is typically characterized by unregulated cell growth. Examples of cancers include, but are not limited to, lung cancer including small cell lung cancer, adenocarcinoma of the lung and squamous carcinoma of the lung, hepatocellular cancer, brain cancer including malignant oligodendroglioma, glioblastoma or glioma, gastrointestinal cancer including but not limited to esophageal cancer, gastric cancer, intestinal cancer, colon cancer and colorectal cancer, kidney clear cell carcinoma, skin basal cell carcinoma, skin squamous cell carcinoma, throat carcinoma, Hodgkin's lymphoma, thyroid medullary carcinoma, pancreatic cancer, adenocarcinoma, fibrosarcoma, cervical cancer, ovarian cancer, bladder cancer, cancer of the urinary tract, breast cancer, endometrial or uterine carcinoma, salivary gland carcinoma, prostate cancer, melanoma, multiple myeloma and B-cell lymphoma, leukemias, duodenal cancer (e.g, adenocarcinoma), and associated metastases. In some embodiments, the type of cancer is selected from: brain cancer, liver cancer, lung cancer, breast cancer, ovarian cancer, and cervical cancer. In some embodiments, the cancer cell is selected from: a glioma cell, a hepatocarcinoma cell, a lung cancer cell, a breast cancer cell, an ovarian carcinoma cell, and a cervical adenocarcinoma cell. In some embodiments, the type of cancer is selected from: pancreatic cancer, colon cancer, rectal cancer, esophageal cancer, leukemia, adenocarcinoma, fibrosarcoma, duodenal adenocarcinoma, brain cancer, liver cancer, lung cancer, breast cancer, ovarian cancer, and cervical cancer.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, and antibody fragments (e.g., a Fab fragment, scFv, minibody, diabody, scFv multimer, or bispecific antibody fragment) so long as they exhibit the desired biological activity.

As used herein, the term "specifically binds to" or is "specific for" refers to measurable and reproducible interactions such as binding between a target and an antibody, that is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In certain embodiments, an antibody that specifically binds to a target has a dissociation constant (Kd) of ≤1 µM, ≤100 nM, ≤10 nM, ≤1 nM, or ≤0.1 nM. In another embodiment, specific binding can include, but does not require exclusive binding.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called "hypervariable regions (HVRs)" both in the light-chain and the heavy chain variable domains (for a total of 6 HVRs per antibody or antigen-binding fragment thereof). As used herein, a "hypervariable region (HVR)" contains highly variable sequence that confers specific antigen-binding to an antibody. The more highly conserved portions of variable domains are called the framework regions (FR). The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., Nature, 256:495-97 (1975); recombinant DNA methods (see, e.g., U.S. Pat. No. 4,816,567); phage-display technologies (see, e.g., Clackson et al., *Nature,* 352:624-628 (1991)); and technologies for producing human or human-like antibodies in animals that have parts or all of the human immunoglobulin loci or genes encoding human immunoglobulin sequences (see, e.g., Jakobovits et al., *Proc. Nat'l Acad. Sci. USA* 90:2551 (1993); Lonberg et al., *Nature* 368:856-859 (1994)).

An "antibody fragment" comprises a portion of an intact antibody, preferably the antigen binding and/or the variable region of the intact antibody. Examples of antibody fragments include Fab, Fab', $F(ab')_2$ and Fv fragments; minibodies; diabodies; scFvs; scFv multimers; linear antibodies; single-chain antibody molecules; and bispecific or multispecific antibodies formed from antibody fragments.

"Single-chain Fv" also abbreviated as "sFv" or "scFv" are antibody fragments that comprise the VH and VL antibody domains connected into a single polypeptide chain. Preferably, the scFv polypeptide further comprises a polypeptide linker between the $V_H$ and $V_L$ domains which enables the scFv to form the desired structure for antigen binding. For a review of the scFv, see Pluckthun in *The Pharmacology of Monoclonal Antibodies,* vol. 113, Rosenburg and Moore eds., Springer-Verlag, New York, pp. 269-315 (1994).

The term "diabodies" refers to small antibody fragments prepared by constructing scFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Diabodies are described in greater detail in, for example, EP 404,097; WO 93/11161; Hollinger et al., *Proc. Nat'l Acad. Sci. USA* 90:6444-48 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA,* 81:6851-55 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. For further details, see, e.g., Jones et al., *Nature* 321:522-525 (1986).

A "human antibody" is one that possesses an amino-acid sequence corresponding to that of an antibody produced by a human and/or has been made using any of the techniques for making human antibodies as disclosed herein. Human antibodies can be produced using various techniques known in the art, such as the methods described in Cole et al., *Monoclonal Antibodies and Cancer Therapy,* Alan R. Liss, p. 77 (1985); Boerner et al., *J. Immunol.,* 147(1):86-95 (1991).

An "isolated" antibody is one that has been identified, separated and/or recovered from a component of its production environment (e.g., naturally or recombinantly). Preferably, the isolated polypeptide is free of contaminant components that would typically interfere with uses for the antibody, e.g., enzymes, hormones, and other proteinaceous or non-proteinaceous solutes.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with cancer are mitigated or eliminated.

As used herein, the term "prevention" includes providing prophylaxis with respect to occurrence or recurrence of a disease in an individual. An individual may be predisposed to, susceptible to a type of cancer, or at risk of developing a type of cancer, but has not yet been diagnosed with the disease.

An "effective amount" refers to at least an amount effective, at dosages and for periods of time necessary, to achieve the desired therapeutic or prophylactic result. An effective amount can be provided in one or more administrations.

A "therapeutically effective amount" is at least the minimum concentration required to effect a measurable improvement of a particular disorder (e.g., cancer). A therapeutically effective amount herein may vary according to factors such as the disease state, age, sex, and weight of the patient, and the ability of the monoclonal antibody to elicit a desired response in the individual. A therapeutically effective amount is also one in which any toxic or detrimental effects of the monoclonal antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in subjects prior to or at an earlier stage of disease, a prophylactically effective amount may be less than a therapeutically effective amount.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment or prevention refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human. In some embodiments, the individual is a non-human animal.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; low molecular weight (less than about 10 residues) polypeptide; proteins, such as serum albumin, gelatin, or immunoglobulins; amino acids such as glycine, glutamine, asparagine, arginine or lysine; carbohydrates including glucose, mannose, or dextrins; and/or nonionic surfactants such as TWEEN™, polyethylene glycol (PEG), and PLURONICS™.

"Pharmaceutically acceptable" buffers and salts include those derived from both acid and base addition salts of the above indicated acids and bases. Specific buffers and/or salts include histidine, succinate and acetate.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

An "isolated" polynucleotide encoding the antibodies herein is a nucleic acid molecule that is identified and separated from at least one contaminant nucleic acid molecule with which it is ordinarily associated in the environment in which it was produced. The isolated nucleic acid molecules encoding the polypeptides and antibodies herein are in a form other than in the form or setting in which it is found in nature. Preferably, the isolated nucleic acid is free of association with all components associated with the production environment.

The term "vector," as used herein, is intended to refer to a nucleic acid molecule capable of transporting another nucleic acid to which it has been linked. Types of vectors include plasmids (i.e., circular double stranded DNA into which additional DNA segments may be ligated) and viral vectors. Certain vectors are capable of autonomous replication in a host cell into which they are introduced (e.g., bacterial vectors having a bacterial origin of replication and episomal mammalian vectors). Other vectors can be integrated into the genome of a host cell and replicated along with the host genome. Moreover, certain vectors are capable of directing the expression of genes to which they are operatively linked. Such vectors are referred to herein as "recombinant expression vectors," or simply, "expression vectors." In the present specification, "plasmid" and "vector" may be used interchangeably as the plasmid is the most commonly used form of vector.

III. Saccharides

Certain aspects of the present disclosure are related to epitopes containing saccharides. As used herein, a "saccharide" may refer to a monosaccharide, an oligosaccharide or a polysaccharide. Monosaccharides include but not limited to fructose, glucose, mannose, fucose, xylose, galactose, lactose, N-acetylneuraminic acid, N-acetyl-galactosamine, N-acetylglucosamine, and sialic acids. An oligosaccharide is a saccharide polymer containing multiple sugar monomers linked by glycosidic linkages of component sugars.

Glycoproteins or proteosaccharides refer to proteins linked with saccharides and may typically contain, for example, O- or N-glycosidic linkages of monosaccharides to compatible amino acid side chains in proteins or to lipid moieties. As used herein, the terms "glycan" and "glycosyl moiety" may be used interchangeably to refer to a saccharide alone or a sugar as the saccharide component of a glycoprotein. Two types of glycosylation are known in the art: N-linked glycosylation to the amide nitrogen of asparagine side chains and O-linked glycosylation to the hydroxy oxygen of serine and threonine side chains. Other saccharides include but not limited to O-GlcNAc, GAG Chain, glycosaminosaccharides, and glycosphinglipid. O- and N-linked saccharides are very common in eukaryotes but may also be found, although less commonly, in prokaryotes.

Certain aspects of the present disclosure relate to N-acetylglucosamine and N-acetyl-galactosamine. N-acetylglucosamine may refer to any amino sugar compound that includes an N-linked glucosamine moiety. As used herein, N-acetylglucosamine may refer to the monosaccharide on its own, or the monosaccharide as a component of a larger polysaccharide. As used herein, N-acetylglucosamine may refer to a saccharide entity on its own, or the saccharide as the glycan component of a glycoprotein or protein glycosylated with one or more N-acetylglucosamine-based components (e.g., mono- or poly-saccharides that contain N-acetylglucosamine).

N-acetyl-galactosamine may refer to any compound that includes glucosamine N-linked to an acetic acid moiety. N-acetyl-galactosamine may refer to any amino sugar compound that includes an N-linked galactosamine moiety. As used herein, N-acetyl-galactosamine may refer to the monosaccharide on its own, or the monosaccharide as a component of a larger polysaccharide. As used herein, N-acetyl-galactosamine may refer to a saccharide entity on its own, or the saccharide as the glycan component of a glycoprotein or protein glycosylated with one or more N-acetyl-galactosamine moieties (e.g., mono- or poly-saccharides that contain N-acetyl-galactosamine).

While many proteins are known to be glycosylated, glycoproteins are often found on the exterior surface of cells (i.e., extracellular) or secreted. Because of this, glycoproteins are highly accessible to external agents (e.g., exogenous compounds administered to a patient). For example, components that specifically recognize certain glycoproteins (e.g., antibodies or lectins) are able to bind, in an intact organism, to cells that express these glycoproteins on their cell surface. Components that specifically recognize certain glycoproteins are also able to bind secreted saccharides or glycoproteins, for example those that may be found freely in certain tissue samples (including, without limitation, in blood or serum).

Lectins are known in the art as sugar-binding proteins which are able to recognize cognate sugar moieties with high specificity. These highly specific binding interactions may be exploited, for example, for the detection of specific saccharides in tissues (e.g., for the detection of cell surface proteins modified by glycosylation with specific sugar moieties). Lectins may include, for example, animal lectins, plant lectins, and pathogen lectins. In mammals, lectins are known to play important roles in the immune system by, e.g., recognizing carbohydrates that are found exclusively on pathogens, or that are inaccessible on host cells.

Certain aspects of the present disclosure use plant lectins to detect the presence or expression of specific sugar moieties. For example, plant lectins may include but not limited to lectins specific to fructose, mannose, glucose, fucose, galactose, N-acetyl-galactosamine, and N-acetyl-glucosamine.

IV. Antibodies

Epitope Binding

Certain aspects of the present disclosure relate to antibodies that specifically bind to an epitope containing N-acetylglucosamine or N-acetyl-galactosamine. As described above, such antibodies will display measurable and reproducible interactions such as binding to an epitope containing N-acetylglucosamine or N-acetyl-galactosamine. For example, an antibody that specifically binds to an epitope is an antibody that binds this epitope with greater affinity, avidity, more readily, and/or with greater duration than it binds to other targets. Examples of epitopes containing N-acetylglucosamine or N-acetyl-galactosamine include glycoproteins containing N-acetylglucosamine or N-acetyl-galactosamine glycans, for example and without limitation cell surface glycoproteins bearing an N-acetylglucosamine or N-acetyl-galactosamine moiety expressed on the surface of a cancer cell.

Specific binding can include, but does not require exclusive binding. While antibodies that specifically bind to an epitope containing N-acetylglucosamine or N-acetyl-galactosamine, they may also be found to bind to other epitopes not containing these moieties, e.g., with a lesser binding affinity than epitopes containing N-acetylglucosamine or N-acetyl-galactosamine.

In some embodiments, antibodies specifically bind to epitopes containing N-acetylglucosamine and N-acetyl-galactosamine. For example, an antibody may be capable of specific binding to an epitope containing N-acetylglucosamine and to an epitope containing N-acetyl-galactosamine. In some embodiments, an antibody may be capable of specific binding to an epitope containing both N-acetylglucosamine and N-acetyl-galactosamine.

In some embodiments, the binding of the antibody to the epitope containing N-acetylglucosamine and/or N-acetyl-galactosamine expressed on the cell surface of the cancer cell inhibits growth of the cancer cell. As used herein, inhibiting the growth of a cell may refer to inhibition its rate of proliferation. Without wishing to be bound to theory, through binding to the cell surface, antibodies may inhibit the growth of cells by a variety of mechanisms. For example, antibody binding to the cell surface may be toxic to the cell or otherwise cause cell death, for example and without limitation, apoptosis or necrosis. Antibody binding to the cell surface may slow or stop cell proliferation. Antibody binding to the cell surface glycoprotein on the cell surface may inhibit or enhance a function of the glycoprotein, for example a cell signaling function, and in so doing the antibody binding may inhibit the growth of the cell. Antibody binding to the cell surface may compete with an extrinsic ligand that accelerates the growth of the cell through binding to the cell surface, for example a growth factor. This competition may be indirect, i.e., the antibody need not competitively bind an epitope on the same glycoprotein as the extrinsic ligand. Antibody binding to the cell surface may also attract one or more components of the immune system, such as natural killer or NK cells, that inhibit the growth of antibody-bound cells. The mechanism(s) by which different antibodies inhibit the growth of cells through binding epitopes on the cell surface may be different depending on the cellular context or the specific antibody or epitope.

Antibody Features

Certain antibodies that specifically bind to an epitope containing N-acetylglucosamine or N-acetyl-galactosamine are described and characterized in the present disclosure. In some embodiments, the antibody is 1C5C9, e.g., as described in PCT/CN2015/087717. In some embodiments, the antibody is a humanized form of antibody 1C5C9, e.g., as described in PCT/CN2015/087717. For example, in some embodiments, the antibody is derived from a humanized parental 1C5C9 antibody. In some embodiments, the humanized parental 105C9 antibody comprises a heavy chain variable region comprising an HVR-H1 sequence of YTFPDYNIH (SEQ ID NO: 1), an HVR-H2 sequence of CIYPYNGNTA (SEQ ID NO: 2), and an HVR-H3 sequence of SDLYYFGSRGFD (SEQ ID NO: 3). In some embodiments, the humanized parental 1C5C9 antibody comprises a light chain variable region comprising an HVR-L1 sequence of RASQDISTYLN (SEQ ID NO: 4), an HVR-L2 sequence of FTSRLHS (SEQ ID NO: 6), and an HVR-L3 sequence of QQGNTLPW (SEQ ID NO: 9). In some embodiments, the humanized parental 1C5C9 antibody comprises a heavy chain variable region comprising the amino acid sequence of QVQLVQSGAEVKKPGASVKVSCKASGYTFPDYNIH-WVRQAPGQGLEWMGCIYPYN GNTAYAQKFQG-RVTMTRDTSISTAYMELSRLRSDDTAVYYCARSD-LYYFGSRGFDY WGQGTLVTVSSA (SEQ ID NO: 10), and/or a light chain variable region comprising the amino acid sequence of DIQMTQSPSSLSASVGDRVTIT-CRASQDISTYLNWYQQKPGKAPKWYFTSRLHSGVP SRFSGSGSGTDFTLTISSLQPEDIATYYCQQGN-TLPWTFGGGTKLEIK (SEQ ID NO: 12).

In some embodiments, the humanized parental 1C5C9 antibody comprises a heavy chain comprising the amino acid sequence of QVQLVQSGAEVKKPGASVKVSCK-ASGYTFPDYNIHWVRQAPGQGLEWMGCIYPYN GNTAYAQKFQGRVTMTRDTSISTAYMELSRLRSDD-TAVYYCARSDLYYFGSRGFDY WGQGTLVTVSSAS-TKGPSVFPLAPSSKSTSGGTAALGCLVKDYFPEPVT-VSWNSGAL TSGVHTFPAVLQSSGLYSLSSVVTVPS-SSLGTQTYICNVNHKPSNTKVDKRVEPKSCD KTH-TCPPCPAPELLGGPSVFLFPPKPKDTLMISRTPEVTCV-VVDVSHEDPEVKFNWYV DGVEVHNAKTKPRE-EQYNSTYRVVSVLTVLHQDWLNGKEYKCKVSNKA-LPAPIEKT ISKAKGQPREPQVYTLPPSRDELT-KNQVSLTCLVKGFYPSDIAVEWESNGQPENNYKT TPPVLDSDGSFFLYSKLTVDKSRWQQGNVFSCSV-MHEALHNHYTQKSLSLSPGK (SEQ ID NO: 11); and/or a light chain comprising the amino acid sequence of DIQMTQSPSSLSASVGDRVTITCRASQDISTYLNW-YQQKPGKAPKWYFTSRLHSGVP SRFSGSGSGTD-FTLTISSLQPEDIATYYCQQGNTLPWTFGGGTK-LEIKRTVAAPSVFIFP PSDEQLKSGTASVVCLLNNFY-PREAKVQWKVDNALQSGNSQESVTEQDSKDS-TYSLS STLTLSKADYEKHKVYACEVTHQGLSSPVT-KSFNRGEC (SEQ ID NO: 15).

In some embodiments, the antibody is a humanized form of antibody 1C5C9. In some embodiments, the antibody comprises a light chain variable region comprising an HVR-L1 sequence of SEQ ID NO: 5, an HVR-L2 sequence of FTSX$_1$LX$_2$S (SEQ ID NO: 25), and an HVR-L3 sequence of SEQ ID NO: 9, where X$_1$ is T or S and X$_2$ is Q or E.

In some embodiments, the antibody is humanized 1C5-VK1. In some embodiments, the antibody comprises a heavy chain variable region comprising an HVR-H1 sequence of YTFPDYNIH (SEQ ID NO: 1), an HVR-H2 sequence of CIYPYNGNTA (SEQ ID NO: 2), and an HVR-H3 sequence of SDLYYFGSRGFD (SEQ ID NO: 3). In some embodiments, the antibody comprises a light chain variable region comprising an HVR-L1 sequence of QASDDISTYLN (SEQ ID NO: 21), an HVR-L2 sequence of FTSNLET (SEQ ID NO: 22), and an HVR-L3 sequence of QQGNTLPW (SEQ ID NO: 9).

In some embodiments, the antibody comprises a heavy chain variable region comprising the amino acid sequence of QVQLVQSGAEVKKPGASVKVSCKASGYTFPDYNIH-WVRQAPGQGLEWMGCIYPYN GNTAYAQKFQG-RVTMTRDTSISTAYMELSRLRSDDTAVYYCARSD-LYYFGSRGFDY WGQGTLVTVSSA (SEQ ID NO: 10), and/or a light chain variable region comprising the amino acid sequence of DIQMTQSPSSLSASVGDRVT-ITCQASDDISTYLNWYQQKPGKAPKLLIYFTSNLE-TGV PSRFSGSGSGTDFTLTISSLQPEDI-ATYYCQQGNTLPWTFGGGTKLEIK (SEQ ID NO: 23).

In some embodiments, the antibody comprises a heavy chain comprising the amino acid sequence of QVQLVQS-GAEVKKPGASVKVSCKASGYTFPDYNIHWVRQ-APGQGLEWMGCIYPYN GNTAYAQKFQGRVT- MTRDTSISTAYMELSRLRSDDTAVYYCARSDLYYFGSRGFDY WGQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 11), and/or a light chain comprising the amino acid sequence of DIQMTQSPSSLSASVGDRVTITCQASQDISTYLNWYQQKPGKAPKLLIYFTSNLETGV PSRFSGSGSGTDFTLTISSLQPEDIATYYCQQGNTLPWTFGGGTKLEIKRTVAAPSVFIF PPSDEQLKSGTASVVCLLNNFYPREAKVQWKVDNALQSGNSQESVTEQDSKDSTYSL SSTLTLSKADYEKHKVYACEVTHQGLSSPVTKSFNRGEC (SEQ ID NO: 24).

In some embodiments, the antibody is humanized 1C5-VK2. In some embodiments, the antibody comprises a heavy chain variable region comprising an HVR-H1 sequence of YTFPDYNIH (SEQ ID NO: 1), an HVR-H2 sequence of CIYPYNGNTA (SEQ ID NO: 2), and an HVR-H3 sequence of SDLYYFGSRGFD (SEQ ID NO: 3). In some embodiments, the antibody comprises a light chain variable region comprising an HVR-L1 sequence of RASQDISTYLN (SEQ ID NO: 4), an HVR-L2 sequence of FTSSLQS (SEQ ID NO: 18), and an HVR-L3 sequence of QQGNTLPW (SEQ ID NO: 9).

In some embodiments, the antibody comprises a heavy chain variable region comprising the amino acid sequence of QVQLVQSGAEVKKPGASVKVSCKASGYTFPDYNIHWVRQAPGQGLEWMGCIYPYN GNTAYAQKFQGRVTMTRDTSISTAYMELSRLRSDDTAVYYCARSDLYYFGSRGFDY WGQGTLVTVSSA (SEQ ID NO: 10), and/or a light chain variable region comprising the amino acid sequence of DIQMTQSPSSLSASVGDRVTITCRASQDISTYLNWYQQKPGKAPKWYFTSSLQSGVP SRFSGSGSGTDFTLTISSLQPEDIATYYCQQGNTLPWTFGGGTKLEIK (SEQ ID NO: 19).

In some embodiments, the antibody comprises a heavy chain comprising the amino acid sequence of QVQLVQSGAEVKKPGASVKVSCKASGYTFPDYNIHWVRQAPGQGLEWMGCIYPYN GNTAYAQKFQGRVTMTRDTSISTAYMELSRLRSDDTAVYYCARSDLYYFGSRGFDY WGQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 11), and/or a light chain comprising the amino acid sequence of DIQMTQSPSSLSASVGDRVTITCRASQDISTYLNWYQQKPGKAPKWYFTSSLQSGVP SRFSGSGSGTDFTLTISSLQPEDIATYYCQQGNTLPWTFGGGTKLEIKRTVAAPSVFIFP PSDEQLKSGTASVVCLLNNFYPREAKVQWKVDNALQSGNSQESVTEQDSKDSTYSLS STLTLSKADYEKHKVYACEVTHQGLSSPVTKSFNRGEC (SEQ ID NO: 20).

In some embodiments, the antibody is humanized 1C5-VK3. In some embodiments, the antibody comprises a heavy chain variable region comprising an HVR-H1 sequence of YTFPDYNIH (SEQ ID NO: 1), an HVR-H2 sequence of CIYPYNGNTA (SEQ ID NO: 2), and an HVR-H3 sequence of SDLYYFGSRGFD (SEQ ID NO: 3). In some embodiments, the antibody comprises a light chain variable region comprising an HVR-L1 sequence of RASQDISTYLA (SEQ ID NO: 5), an HVR-L2 sequence of FTSTLQS (SEQ ID NO: 7), and an HVR-L3 sequence of QQGNTLPW (SEQ ID NO: 9).

In some embodiments, the antibody comprises a heavy chain variable region comprising the amino acid sequence of QVQLVQSGAEVKKPGASVKVSCKASGYTFPDYNIHWVRQAPGQGLEWMGCIYPYN GNTAYAQKFQGRVTMTRDTSISTAYMELSRLRSDDTAVYYCARSDLYYFGSRGFDY WGQGTLVTVSSA (SEQ ID NO: 10), and/or a light chain variable region comprising the amino acid sequence of DIQMTQSPSSLSASVGDRVTITCRASQDISTYLAWYQQKPGKAPKLLIYFTSTLQSGVP SRFSGSGSGTDFTLTISSLQPEDAATYYCQQGNTLPWTFGGGTKLEIK (SEQ ID NO: 13).

In some embodiments, the antibody comprises a heavy chain comprising the amino acid sequence of QVQLVQSGAEVKKPGASVKVSCKASGYTFPDYNIHWVRQAPGQGLEWMGCIYPYN GNTAYAQKFQGRVTMTRDTSISTAYMELSRLRSDDTAVYYCARSDLYYFGSRGFDY WGQGTLVTVSSASTKGPSVFPLAPSSKSTSGGTAALGCLVKDYFPEPVTVSWNSGAL TSGVHTFPAVLQSSGLYSLSSVVTVPSSSLGTQTYICNVNHKPSNTKVDKRVEPKSCD KTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESNGQPENNYKT TPPVLDSDGSFFLYSKLTVDKSRWQQGNVFSCSVMHEALHNHYTQKSLSLSPGK (SEQ ID NO: 11), and/or a light chain comprising the amino acid sequence of DIQMTQSPSSLSASVGDRVTITCRASQDISTYLAWYQQKPGKAPKLLIYFTSTLQSGVP SRFSGSGSGTDFTLTISSLQPEDAATYYCQQGNTLPWTFGGGTKLEIKRTVAAPSVFIF PPSDEQLKSGTASVVCLLNNFYPREAKVQWKVDNALQSGNSQESVTEQDSKDSTYSL SSTLTLSKADYEKHKVYACEVTHQGLSSPVTKSFNRGEC (SEQ ID NO: 16).

In some embodiments, the antibody is humanized 1C5-VK4. In some embodiments, the antibody comprises a heavy chain variable region comprising an HVR-H1 sequence of YTFPDYNIH (SEQ ID NO: 1), an HVR-H2 sequence of CIYPYNGNTA (SEQ ID NO: 2), and an HVR-H3 sequence of SDLYYFGSRGFD (SEQ ID NO: 3). In some embodiments, the antibody comprises a light chain variable region comprising an HVR-L1 sequence of RASQDISTYLA (SEQ ID NO: 5), an HVR-L2 sequence of FTSSLES (SEQ ID NO: 8), and an HVR-L3 sequence of QQGNTLPW (SEQ ID NO: 9).

In some embodiments, the antibody comprises a heavy chain variable region comprising the amino acid sequence of QVQLVQSGAEVKKPGASVKVSCKASGYTFPDYNIHWVRQAPGQGLEWMGCIYPYN GNTAYAQKFQGRVTMTRDTSISTAYMELSRLRSDDTAVYYCARSDLYYFGSRGFDY WGQGTLVTVSSA (SEQ ID NO: 10), and/or a light chain variable region comprising the amino acid sequence of AIQLTQSPSSLSASVGDRVTITCRASQDISTYLAWYQQKPGKAPKLLIYFTSSLESGVP SRFSGSGSGTDFTLTISSLQPEDVATYYCQQGNTLPWTFGGGTKLEIK (SEQ ID NO: 14).

In some embodiments, the antibody comprises a heavy chain comprising the amino acid sequence of QVQLVQS- GAEVKKPGASVKVSCKASGYTFPDYNIHWVRQ-APGQGLEWMGCIYPYN GNTAYAQKFQGRVTMTR-DTSISTAYMELSRLRSDDTAVYYCARSDLYYFGS-RGFDY WGQGTLVTVSSASTKGPSVFPLAPSSKST-SGGTAALGCLVKDYFPEPVTVSWNSGAL TSGVHT-FPAVLQSSGLYSLSSVVTVPSSSLGTQTYICNVNHK-PSNTKVDKRVEPKSCD KTHTCPPCPAPELLGGPS-VFLFPPKPKDTLMISRTPEVTCVVVDVSHEDPEVK-FNWYV DGVEVHNAKTKPREEQYNSTYRVVSVLTV-LHQDWLNGKEYKCKVSNKALPAPIEKT ISKAKG-QPREPQVYTLPPSRDELTKNQVSLTCLVKGFYPSDIA-VEWESNGQPENNYKT TPPVLDSDGSFFLYSK-LTVDKSRWQQGNVFSCSVMHEALHNHYTQKSLSL-SPGK (SEQ ID NO: 11), and/or a light chain comprising the amino acid sequence of AIQLTQSPSSLSASVGDRVTIT-CRASQDISTYLAWYQQKPGKAPKLLIYFTSSLESGVP SRFSGSGSGTDFTLTISSLQPEDVATYYCQQGNTLPW-TFGGGTKLEIKRTVAAPSVFIF PPSDEQLKSGTASVV-CLLNNFYPREAKVQWKVDNALQSGNSQESVTEQD-SKDSTYSL SSTLTLSKADYEKHKVYACEVTHQGL-SSPVTKSFNRGEC (SEQ ID NO: 17).

In some embodiments, the antibody comprises a heavy chain variable region comprising three HVRs of SEQ ID NO: 10 and/or a light chain variable region comprising three HVRs of SEQ ID NO: 12. In some embodiments, the antibody comprises a heavy chain variable region comprising three HVRs of SEQ ID NO: 10 and/or a light chain variable region comprising three HVRs of SEQ ID NO: 13. In some embodiments, the antibody comprises a heavy chain variable region comprising three HVRs of SEQ ID NO: 10 and/or a light chain variable region comprising three HVRs of SEQ ID NO: 14. In some embodiments, the antibody comprises a heavy chain variable region comprising three HVRs of SEQ ID NO: 10 and/or a light chain variable region comprising three HVRs of SEQ ID NO: 19. In some embodiments, the antibody comprises a heavy chain variable region comprising three HVRs of SEQ ID NO: 10 and/or a light chain variable region comprising three HVRs of SEQ ID NO: 23. In some embodiments, the antibody comprises a heavy chain variable region comprising the amino acid sequence of SEQ ID NO: 10 and/or a light chain variable region comprising the amino acid sequence of SEQ ID NO: 12. In some embodiments, the antibody comprises a heavy chain variable region comprising the amino acid sequence of SEQ ID NO: 10 and/or a light chain variable region comprising the amino acid sequence of SEQ ID NO: 13. In some embodiments, the antibody comprises a heavy chain variable region comprising the amino acid sequence of SEQ ID NO: 10 and/or a light chain variable region comprising the amino acid sequence of SEQ ID NO: 14. In some embodiments, the antibody comprises a heavy chain variable region comprising the amino acid sequence of SEQ ID NO: 10 and/or a light chain variable region comprising the amino acid sequence of SEQ ID NO: 19. In some embodiments, the antibody comprises a heavy chain variable region comprising the amino acid sequence of SEQ ID NO: 10 and/or a light chain variable region comprising the amino acid sequence of SEQ ID NO: 23

The antibodies useful in the present invention can encompass monoclonal antibodies, polyclonal antibodies, antibody fragments (e.g., Fab, Fab'-SH, Fv, scFv, and F(ab')$_2$), chimeric antibodies, bispecific antibodies, multivalent antibodies, heteroconjugate antibodies, fusion proteins comprising an antibody portion, humanized antibodies, and any other modified configuration of the immunoglobulin molecule that comprises an antigen recognition site of the required specificity (e.g., for epitope containing N-acetylglucosamine or N-acetyl-galactosamine), including glycosylation variants of antibodies, amino acid sequence variants of antibodies, and covalently modified antibodies. The antibodies may be murine, rat, human, or of any other origin (including chimeric or humanized antibodies).

In some embodiments, the antibody that specifically binds to an epitope containing N-acetylglucosamine or N-acetyl-galactosamine is a monoclonal antibody. For example, the monoclonal antibodies may be made using the hybridoma method first described by Kohler et al., *Nature,* 256:495 (1975), or may be made by recombinant DNA methods (U.S. Pat. No. 4,816,567).

Culture medium in which hybridoma cells are growing is assayed for production of monoclonal antibodies directed against the antigen (e.g., an epitope containing N-acetylglucosamine or N-acetyl-galactosamine). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

Monoclonal antibodies may also be made by recombinant DNA methods, such as those described above. DNA encoding the monoclonal antibodies is readily isolated and sequenced using conventional procedures, placed into expression vectors, and transfected into host cells such as *E. coli* cells or CHO cells to produce recombinant monoclonal antibodies.

In some embodiments, the antibody that specifically binds to an epitope containing N-acetylglucosamine or N-acetyl-galactosamine is a humanized antibody. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. See Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. Humanization can be essentially performed following the method of Jones et al., *Nature* 321: 522-525 (1986); or through substituting non-human CDR sequences for the corresponding sequences of a human antibody. To ensure humanized antibodies retain high affinity for the antigen, humanized antibodies may be prepared by a process of analyzing the parental sequences and various conceptual humanized products using three-dimensional models of the parental and humanized sequences. Three-dimensional immunoglobulin models are commonly available and are familiar to those skilled in the art. In general, the CDR residues are directly and most substantially involved in influencing antigen binding.

In some embodiments, the antibody that specifically binds to an epitope containing N-acetylglucosamine or N-acetyl-galactosamine is a human antibody. Methods known in the art for producing human antibodies include, without limitation, phage display technology and use of transgenic animals that produce human antibodies in response to antigen.

In some embodiments, the antibody that specifically binds to an epitope containing N-acetylglucosamine or N-acetyl-galactosamine is a chimeric antibody. Chimeric antibodies may refer to an antibody in which residues from a complementarity determining region (CDR) or variable region derived from one species are joined with sequences corresponding to the constant region from another species. Methods for generating chimeric antibodies are known in the art (see, e.g., U.S. Pat. No. 4,816,567).

In some embodiments, the antibody that specifically binds to an epitope containing N-acetylglucosamine or N-acetylgalactosamine is an antibody fragment. In some embodiments, the antibody that specifically binds to an epitope containing N-acetylglucosamine or N-acetyl-galactosamine is a Fab fragment, scFv, minibody, diabody, scFv multimer, or bispecific antibody fragment. Fab, Fv and scFv antibody fragments can all be expressed in and secreted from *E. coli*, thus allowing the straightforward production of large amounts of these fragments, or isolated from phage libraries. Such linear antibody fragments may be monospecific or bispecific.

In some embodiments, the antibody that specifically binds to an epitope containing N-acetylglucosamine or N-acetylgalactosamine is a bispecific antibody. Bispecific antibodies (BsAbs) are antibodies that have binding specificities for at least two different epitopes, including those on the same or another protein. Methods for making bispecific antibodies are known in the art. Traditional production of full length bispecific antibodies is based on the coexpression of two immunoglobulin heavy-chain/light chain pairs, where the two chains have different specificities.

In some embodiments, the antibody that specifically binds to an epitope containing N-acetylglucosamine or N-acetylgalactosamine is a multivalent antibody. Multivalent antibodies may refer to any antibody with more than 2 antigen-binding sites. In some embodiments, the antibody that specifically binds to an epitope containing N-acetylglucosamine or N-acetyl-galactosamine is a heteroconjugate antibody. Heteroconjugate antibodies may refer to any antibody created by linking two antibodies with different specificities, such as by a covalent linkage.

According to a different approach, antibody variable domains with the desired binding specificities (antibody-antigen combining sites) are fused to immunoglobulin constant domain sequences. DNAs encoding the immunoglobulin heavy chain fusions and, if desired, the immunoglobulin light chain, are inserted into separate expression vectors, and are co-transfected into a suitable host organism.

In some embodiments, compositions containing an antibody that specifically binds to an epitope containing N-acetylglucosamine or N-acetyl-galactosamine may include pharmaceutically acceptable carriers, excipients, or stabilizers that are nontoxic to the cell or mammal being exposed thereto at the dosages and concentrations employed as part of a pharmaceutical composition. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Polynucleotides, Vectors Encoding Antibodies, and Host Cells

Certain aspects of the present disclosure relate to the production of antibodies that specifically bind to an epitope containing N-acetylglucosamine or N-acetyl-galactosamine. In particular, certain aspects relate to isolated polynucleotides containing a nucleic acid sequence encoding an antibody that specifically binds to an epitope containing N-acetylglucosamine or N-acetyl-galactosamine. As described above, polynucleotides may refer to deoxyribonucleotides, ribonucleotides, modified nucleotides or bases, and/or their analogs. These polynucleotides may be produced in vivo in a host cell or through in vitro transcription. Polynucleotides encoding an antibody may refer to polynucleotides bearing the sequence encoding the antibody as it was identified in a cell producing the antibody (e.g., a B cell or hybridoma), or polynucleotides containing synonymous mutations in the sequence that distinguish them from their naturally occurring counterparts but, due to the inherent degeneracy of the genetic code, encode a similar protein. Polynucleotides may be isolated by any means known in the art, including PCR followed by precipitation-based purification of the PCR reaction, or a slice of agarose gel containing the PCR product, or by purification of a vector containing the polynucleotide from a host cell (e.g., plasmid preparation from *E. coli*).

Certain aspects of the present disclosure relate to vectors containing a nucleic acid sequence encoding an antibody that specifically binds to an epitope containing N-acetylglucosamine or N-acetyl-galactosamine. For recombinant production of antibodies or fragments thereof, nucleic acids encoding the desired antibodies or antibody fragments are isolated and inserted into a replicable vector for further cloning (amplification of the DNA) or for expression. DNA encoding the polyclonal or monoclonal antibodies is readily isolated (e.g., with oligonucleotide probes that specifically bind to genes encoding the heavy and light chains of the antibody) and sequenced using conventional procedures. Many cloning and/or expression vectors are commercially available.

Vector components generally include, but are not limited to, one or more of the following, a signal sequence, an origin of replication, one or more marker genes, a multiple cloning site containing recognition sequences for numerous restriction endonucleases, an enhancer element, a promoter, and a transcription termination sequence. Both expression and cloning vectors contain a nucleic acid sequence that enables the vector to replicate in one or more selected host-cells. Such sequences are well known for a variety of bacteria, yeast, and viruses. Expression and cloning vectors may also contain a selection gene, known as a selectable marker, whose expression confers resistance to antibiotics or other toxins, complements auxotrophic deficiencies, or supplies critical nutrients not available from complex media.

Expression and cloning vectors usually contain a promoter that is recognized by the host organism and is operably linked to the nucleic acid encoding the antibodies (e.g., antibodies that specifically bind to an epitope containing N-acetylglucosamine or N-acetyl-galactosamine) or fragments thereof. Promoters suitable for use with prokaryotic hosts include the phoA promoter, lactamase and lactose promoter systems, alkaline phosphatase promoter, a tryptophan promoter system, and hybrid promoters such as the tac promoter, although other known bacterial promoters are also suitable. Promoters for use in bacterial systems also will contain a Shine-Dalgarno (S.D.) sequence operably linked to the DNA encoding the antibodies and antibody fragments. Promoter sequences are known for eukaryotes, including the yeast promoters for 3-phosphoglycerate kinase or other glycolytic enzymes and mammalian promoters obtained from the genomes of viruses such as polyoma virus, cytomegalovirus, and most preferably Simian Virus 40 (SV40).

Various heterologous mammalian promoters, e.g., the actin promoter, immunoglobulin promoter, and heat-shock promoters, are also known. Expression vectors used in eukaryotic host cells will also contain sequences necessary for the termination of transcription and for stabilizing the mRNA.

Certain aspects of the present disclosure relate to isolated host cells with vectors containing a nucleic acid sequence encoding an antibody that specifically binds to an epitope containing N-acetylglucosamine or N-acetyl-galactosamine. Suitable host-cells for cloning or expressing the DNA encoding antibodies (e.g., antibodies that specifically bind to an epitope containing N-acetylglucosamine or N-acetyl-galactosamine) or fragments thereof in the vectors described herein prokaryotes such as Gram-negative or Gram-positive organisms, for example, Enterobacteriaceae such as *E. coli*. In addition to prokaryotes, eukaryotic microbes such as filamentous fungi or yeast are also suitable cloning or expression hosts, such as *Saccharomyces cerevisiae*. For a review discussing the use of yeasts and filamentous fungi for the production of therapeutic proteins, see, e.g., Gerngross, *Nat. Biotech.* 22: 1409-1414 (2004). Suitable host-cells for the expression of glycosylated antibodies or antibody fragments are derived from multicellular organisms. Examples of invertebrate cells include plant and insect-cells such as *Spodoptera frugiperda* (caterpillar), *Aedes aegypti* (mosquito), *Drosophila melanogaster* (fruitfly), or *Bombyx mori* (moth) cells. Examples of useful mammalian host-cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Nat'l Acad. Sci. USA* 77:4216 (1980)); African green monkey kidney cells (VERO-76, ATCC CRL-1587); human cervical carcinoma cells (HELA, ATCC CCL 2); and a human hepatoma line (Hep G2). For a review of certain mammalian host cell lines suitable for antibody production, see, e.g., Yazaki and Wu, Methods in Molecular Biology, Vol. 248 (B. K. C. Lo, ed., Humana Press, Totowa, N.J., 2003), pp. 255-268. These examples are illustrative rather than limiting.

Antibody Production and Purification

Certain aspects of the present disclosure relate to methods of producing an antibody by culturing host cells with vectors containing a nucleic acid sequence encoding an antibody and recovering the antibody from the cell culture. Host cells are transformed with the above-described expression or cloning vectors for antibody or antibody fragment production and cultured in conventional nutrient media modified as appropriate for inducing promoters, selecting transformants, or amplifying the genes encoding the desired sequences.

The host-cells used to produce the antibodies (e.g., antibodies that specifically bind to an epitope containing N-acetylglucosamine or N-acetyl-galactosamine) or antibody fragments described herein may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host-cells. Any of these media may be supplemented as necessary with hormones and/or other growth factors (such as insulin, transferrin, or epidermal growth factor), salts (such as sodium chloride, calcium, magnesium, and phosphate), buffers, nucleotides, antibiotics, trace elements, and glucose or an equivalent energy source. Any other necessary supplements may also be included at appropriate concentrations that would be known to those skilled in the art. The culture conditions, such as temperature, pH, and the like, are those previously used with the host-cell selected for expression, and will be apparent to the ordinarily skilled artisan.

When using recombinant techniques, the antibodies (e.g., antibodies that specifically bind to an epitope containing N-acetylglucosamine or N-acetyl-galactosamine) or antibody fragments can be produced intracellularly, in the periplasmic space, or secreted directly into the medium. Antibodies prepared from such cells can be purified using, for example, hydroxylapatite chromatography, gel electrophoresis, dialysis, and affinity chromatography, such as that using protein A or protein G attached to a matrix (e.g., agarose).

In general, various methodologies for purifying preparing antibodies for use in research, testing, and clinical applications are well-established in the art, consistent with the above-described methodologies and/or as deemed appropriate by one skilled in the art for a particular antibody of interest.

V. Cancer

Certain aspects of the present disclosure relate to methods for treating or preventing cancer in an individual by administering to the individual an effective amount of a composition containing an antibody that specifically binds to an epitope containing N-acetylglucosamine or N-acetyl-galactosamine, where the epitope is expressed by a cancer cell. In some embodiments, the epitope is expressed on a cell surface of a cancer cell. In some embodiments, binding of the antibody to the epitope expressed on the cell surface of the cancer cell inhibits growth of the cancer cell.

Certain glycoproteins, particularly N-acetylglucosamine and/or N-acetyl-galactosamine, have been found to be highly expressed on the cell surface of many types of human cancer cells, as compared to little or no expression on the cell surface of normal human cells (see, e.g., PCT/CN2015/087717). As a result, these sugar moieties may serve as biomarkers for the presence of cancer that may also be used to preferentially target therapeutic agents (e.g., antibodies) to cancer cells. Advantageously, antibodies specific to N-acetylglucosamine and/or N-acetyl-galactosamine may bind to the cell surface and are able to inhibit the growth of cancer cells expressing these sugar moieties.

Described herein are novel antibodies that specifically bind to an epitope containing N-acetylglucosamine and/or N-acetyl-galactosamine. As described below, these antibodies are effective in inhibiting the growth of different types of cancer cells in various tumor xenograft models. Tumor xenograft models are known in the art as a powerful tool for testing and predicting the drug response of human tumors (see, e.g., Richmond, A. and Su, Y. (2008) *Dis. Model Mech.* 1(2-3): 78-82). These antibodies are also reactive against a number of different human tumor cell lines. In addition, these antibodies were found to be better than existing antibodies in multiple models of inflammation, e.g., IBD and arthritis.

While the results described herein predict that antibodies that specifically bind to an epitope containing N-acetylglucosamine or N-acetyl-galactosamine are broadly effective against multiple forms of human cancer. In some embodiments, the cancer cell whose growth is inhibited by the antibody is selected from: a pancreatic adenocarcinoma cell, a colon adenocarcinoma cell, a rectal adenocarcinoma cell, an esophageal adenocarcinoma cell, a leukemia cell, an adenoid carcinoma cell, a fibrosarcoma cell, a duodenal adenocarcinoma cell, a glioma cell, a hepatocarcinoma cell, a lung cancer cell, a breast cancer cell, a glioblastoma cell, an ovarian carcinoma cell, a cervical adenocarcinoma cell, a colon carcinoma cell, a stomach or gastric carcinoma cell, an esophageal carcinoma cell, and a fibrosarcoma cell.

In some embodiments, the cancer cell is a pancreatic adenocarcinoma cell. Pancreatic adenocarcinoma cells may refer to any adenocarcinoma cells originating from the pancreas, including primary tumors or pancreatic adenocarcinoma cells that have metastasized to other sites. In some embodiments, the pancreatic adenocarcinoma cell is a pancreatic ductal adenocarcinoma cell.

In some embodiments, the cancer cell is a colon or rectal adenocarcinoma cell. Colon or rectal adenocarcinoma cells may refer to any adenocarcinoma cells originating from the colon or rectum, including primary tumors or adenocarcinoma cells that have metastasized to other sites. In some embodiments, the adenocarcinoma cell is a moderately differentiated colon adenocarcinoma cell.

In some embodiments, the cancer cell is a glioma or glioblastoma cell. Glioma cells may refer to any malignant cell originating from a glial cell, e.g., glial cells of the brain or spine, including primary tumors or glioma cells that have metastasized to other sites. Glioma cells may refer to a homogeneous population of glioma cells, or a mixed population of cells arising from different types of glia. In some embodiments, the glioma cell may be an oligodendroglioma cell, a brainstem glioma cell, an ependymoma cell, or an optic nerve glioma cell. Gliomas can include grade III astrocytomas, oligodendrogliomas, and oligoastrocytomas. Glioblastoma cells refer to malignant cells originating from an astrocyte (typically used to characterize grade IV gliomas or astrocytomas), e.g., astrocytes of the brain, including primary tumors or glioblastoma cells that have metastasized to other sites. Glioblastoma cells may include primary or de novo tumors and secondary tumors and may include other cell types and blood vessels.

In some embodiments, the cancer cell is a hepatocarcinoma cell. Hepatocarcinoma cells may refer to any carcinoma cell originating from the liver, including primary tumors or hepatocarcinoma cells that have metastasized to other sites.

In some embodiments, the cancer cell is a lung cancer cell. Lung cancer cells may refer to any cancer cell originating from the lung, including primary tumors or lung cancer cells that have metastasized to other sites. In some embodiments, the lung cancer cell may be a non-small-cell lung cancer cell. In some embodiments, the lung cancer cell may be a lung adenocarcinoma cell. In some embodiments, the lung cancer cell may be a lung squamous cell carcinoma. In some embodiments, the lung cancer cell may be a small-cell lung cancer cell.

In some embodiments, the cancer cell is a breast cancer cell. Breast cancer cells may refer to any cancer cell originating from the breast, including primary tumors or breast cancer cells that have metastasized to other sites. In some embodiments, the breast cancer cell may be a ductal carcinoma in situ cell. In some embodiments, the breast cancer cell may be an invasive ductal carcinoma cell. In some embodiments, the breast cancer cell may be an invasive lobular carcinoma cell.

In some embodiments, the cancer cell is an ovarian carcinoma cell. Ovarian carcinoma cells may refer to any carcinoma cell originating from the ovary, including primary tumors or ovarian carcinoma cells that have metastasized to other sites. In some embodiments, the ovarian carcinoma cell may be a surface epithelial-stromal tumor cell. In some embodiments, the ovarian carcinoma cell may be a sex cord-stromal tumor cell. In some embodiments, the ovarian carcinoma cell may be a germ cell tumor cell. Ovarian carcinoma cells may refer to a homogeneous population of ovarian carcinoma cells, or a mixed population of cells arising from different types of ovarian carcinomas.

In some embodiments, the cancer cell is a cervical adenocarcinoma cell. Cervical adenocarcinoma carcinoma cells may refer to any adenocarcinoma cell originating from the cervix, including primary tumors or cervical adenocarcinoma cells that have metastasized to other sites. In some embodiments, the cervical adenocarcinoma cell is an adenosquamous carcinoma cell.

In some embodiments, the cancer cell is a colon carcinoma cell. Colon carcinoma cells may refer to any carcinoma cell originating from the colon or rectum, including primary tumors or colon carcinoma cells that have metastasized to other sites. In some embodiments, the colon carcinoma cell is an adenocarcinoma cell. In some embodiments, the colon carcinoma cell is an adenosquamous carcinoma cell.

In some embodiments, the cancer cell is a stomach or gastric carcinoma cell. Stomach or gastric carcinoma cells may refer to any carcinoma cell originating from the stomach, including primary tumors or stomach carcinoma cells that have metastasized to other sites. In some embodiments, the stomach or gastric carcinoma cell is an adenocarcinoma cell. In some embodiments, the stomach or gastric carcinoma cell is a diffuse type adenocarcinoma (mucinous, colloid, linitis plastica, leather-bottle stomach) cell. In some embodiments, the stomach or gastric carcinoma cell is a lymphoma cell.

In some embodiments, the cancer cell is an esophageal carcinoma cell. Esophageal carcinoma cells may refer to any carcinoma cell originating from the esophagus, including primary tumors or esophageal carcinoma cells that have metastasized to other sites. In some embodiments, the esophageal carcinoma cell is an adenocarcinoma cell. In some embodiments, the esophageal carcinoma cell is a squamous carcinoma cell.

In some embodiments, the cancer cell is a fibrosarcoma cell. Fibrosarcoma cells may refer to any carcinoma cell originating from the fibrous connective tissue, including primary tumors or esophageal carcinoma cells that have metastasized to other sites.

In some embodiments, the cancer cell is a leukemia cell. Leukemia cells may refer to any malignant white blood cell, typically originating in the bone marrow, and includes chronic, acute, lymphocytic, and myelogenous leukemia cells. For example, in some embodiments, the leukemia cell may be an acute T leukemia cell.

In some embodiments, the cancer cell is an adenoid carcinoma cell, including primary tumors or esophageal carcinoma cells that have metastasized to other sites. In some embodiments, the adenoid carcinoma cell is an adenoid cystic carcinoma cell.

VI. Gastrointestinal Disease and Rheumatoid Arthritis

Certain aspects of the present disclosure relate to methods for treating or preventing gastrointestinal disease by administering to the individual an effective amount of a composition containing an antibody that specifically binds to an epitope containing N-acetylglucosamine or N-acetyl-galactosamine, where the epitope is expressed by an inflammatory cell. In some embodiments, the individual has, or has been diagnosed with, a gastrointestinal disease of the present disclosure.

In some embodiments, the epitope is expressed on a cell surface of an inflammatory cell. In some embodiments, the inflammatory cell is an intestinal inflammatory cell of colitis, inflammatory bowel disease, or gastroenteritis, and the epitope is expressed on a cell surface of the inflammatory cell. As described herein, antibodies that specifically recognize an epitope containing N-acetylglucosamine or N-acetyl-galactosamine may bind to inflammatory cells (e.g., leukocytes, such as neutrophils, macrophages, monocytes, eosinophils, and/or basophils) at sites of inflammation in the colon, such as those seen in diseases characterized by inflammation of the colon (e.g., colitis, IBD, or gastroenteritis).

Other aspects of the present disclosure relate to methods for treating or preventing rheumatoid arthritis by administering to the individual an effective amount of a composition containing an antibody that specifically binds to an epitope containing N-acetylglucosamine or N-acetyl-galactosamine. In some embodiments, the individual has, or has been diagnosed with, rheumatoid arthritis. In some embodiments, the epitope is expressed by an inflammatory cell. The results described herein suggest that antibodies against N-acetylglucosamine and/or N-acetyl-galactosamine (e.g., antibody 1C5C9, or variants thereof such as VK1, VK2, VK3, and/or VK4) may be effective in treating one or more symptoms of rheumatoid arthritis. In some embodiments, the inflammatory cell is a T- or B-cell.

In some embodiments, the inflammatory cell is an inflammatory cell of rheumatoid arthritis. As described herein, antibodies that specifically recognize an epitope containing N-acetylglucosamine or N-acetyl-galactosamine may be useful in treating or preventing one or more symptoms of rheumatoid arthritis. For example, these antibodies have demonstrated efficacy in a collagen-induced arthritis model, which is known in the art as a commonly studied autoimmune model of rheumatoid arthritis (see, e.g., Brand, D. D. et al. (2007) *Nat. Protoc.* 2:1269-1275).

VII. Methods of Treatment

Cancer

Certain aspects of the present disclosure relate to methods for treating or preventing cancer in an individual by administering to the individual an effective amount of a composition containing an antibody that specifically binds to an epitope containing N-acetylglucosamine or N-acetyl-galactosamine. It is a surprising finding described herein that antibodies that specifically bind to an epitope containing N-acetylglucosamine or N-acetyl-galactosamine, expressed on a cell surface of or in the cancer cell, may be used to inhibit the growth of a variety of cancer cells. In some embodiments, the binding of the antibody to the epitope expressed on the cell surface of the cancer cell inhibits growth of the cancer cell.

In some embodiments, the cancer may include pancreatic cancer, colon cancer, rectal cancer, esophageal cancer, leukemia, adenocarcinoma, fibrosarcoma, duodenal adenocarcinoma, brain cancer, liver cancer, lung cancer, breast cancer, ovarian cancer, cervical cancer, colon cancer, stomach cancer, esophageal cancer, and fibrosarcoma. In some embodiments, the individual has, or has been diagnosed with, a cancer of the present disclosure. Since the present disclosure demonstrates that many types of cancer tissues express high levels of N-acetylglucosamine or N-acetyl-galactosamine, the methods described herein may be broadly effective in treating many types of cancer. In some embodiments, the cancer to be treated or prevented refers to a primary tumor, e.g., a primary tumor representing pancreatic cancer, colon cancer, rectal cancer, esophageal cancer, leukemia, adenocarcinoma, fibrosarcoma, duodenal adenocarcinoma, brain cancer, liver cancer, lung cancer, breast cancer, ovarian cancer, cervical cancer, colon cancer, stomach cancer, esophageal cancer, or fibrosarcoma. In some embodiments, the cancer to be treated or prevented refers to a metastatic cancer originally representing pancreatic cancer, colon cancer, rectal cancer, esophageal cancer, leukemia, adenocarcinoma, fibrosarcoma, duodenal adenocarcinoma, brain cancer, liver cancer, lung cancer, breast cancer, ovarian cancer, cervical cancer colon cancer, stomach cancer, esophageal cancer, or fibrosarcoma.

In some embodiments, the cancer to be treated or prevented is a brain cancer. Brain cancer may refer to any cancer originating from the brain, including but not limited to a cancer made of the cells described above. Examples of brain cancers may include without limitation gliomas, meningiomas, nerve sheath tumors, and pituitary adenomas. Brain cancer may also refer to a cancer originating from the central nervous system, e.g., the spine.

In some embodiments, the cancer to be treated or prevented is a liver cancer. Liver cancer may refer to any cancer originating from the liver, including but not limited to a cancer made of the cells described above. Examples of liver cancers may include without limitation hepatocarcinomas, cholangiocarcinomas, and hepatoblastomas.

In some embodiments, the cancer to be treated or prevented is a lung cancer. Lung cancer may refer to any cancer originating from the lung, including but not limited to a cancer made of the cells described above. Examples of lung cancers may include without limitation non-small-cell lung cancers, including adenocarcinomas, squamous-cell carcinomas, and large-cell carcinomas, as well as small-cell lung carcinomas.

In some embodiments, the cancer to be treated or prevented is a breast cancer. Breast cancer may refer to any cancer originating from the breast, including but not limited to a cancer made of the cells described above. Examples of breast cancers may include without limitation ductal carcinomas in situ, invasive ductal carcinomas, triple negative breast cancer (e.g., cancer made of cells negative for progesterone, estrogen, and HER2/neu receptors), and inflammatory breast cancer.

In some embodiments, the cancer to be treated or prevented is an ovarian cancer. Ovarian cancer may refer to any cancer originating from the ovary, including but not limited to a cancer made of the cells described above. Examples of ovarian cancers may include without limitation surface epithelial-stromal tumors (including, e.g., endometrioid tumors, mucinous cystadenocarcinomas, and serous tumors), germ cell tumors, sex cord-stromal tumors, and mixed ovarian tumors.

In some embodiments, the cancer to be treated or prevented is a cervical cancer. Cervical cancer may refer to any cancer originating from the cervix, including but not limited to a cancer made of the cells described above. Examples of cervical cancers may include without limitation squamous cell carcinomas, adenocarcinomas, small cell carcinomas, adenosquamous carcinomas, neuroendocrine tumors, villoglandular adenocarcinomas, and glassy cell carcinomas.

In some embodiments, the cancer to be treated or prevented is a colon cancer. Colon cancer may refer to any cancer originating from the colon or rectum, including but not limited to a cancer made of the cells described above. Examples of colon cancers may include without limitation adenocarcinomas and adenosquamous carcinomas.

In some embodiments, the cancer to be treated or prevented is a stomach or gastric cancer. Stomach or gastric cancer may refer to any cancer originating from the stomach, including but not limited to a cancer made of the cells described above. Examples of stomach or gastric cancers may include without limitation adenocarcinomas, diffuse type adenocarcinomas (mucinous, colloid, linitis plastica, leather-bottle stomach) and lymphoma.

In some embodiments, the cancer to be treated or prevented is an esophageal cancer. Esophageal cancer may refer to any cancer originating from the esophagus, including but not limited to a cancer made of the cells described above. Examples of esophageal cancers may include without limitation adenocarcinomas and squamous carcinomas.

In some embodiments, the cancer to be treated or prevented is a fibrosarcoma. Fibrosarcomas may refer to any carcinomas originating from the fibrous connective tissue, including but not limited to a cancer made of the cells described above.

In some embodiments, the cancer to be treated or prevented is a pancreatic cancer. Pancreatic cancer may refer to any cancer originating from the pancreas, including but not limited to a cancer made of the cells described above, such as a pancreatic ductal carcinoma cell.

In some embodiments, the cancer to be treated or prevented is a leukemia. Leukemia may refer to any cancer characterized by malignant white blood cells, including but not limited to a cancer made of the cells described above, such as an acute T leukemia cell.

In some embodiments, the cancer to be treated or prevented is an adenocarcinoma. Adenocarcinoma may refer to any carcinoma originating from a glandular structure in an epithelium, including but not limited to a cancer made of the cells described above, such as an adenoid cystic carcinoma cell or a duodenal adenocarcinoma cell.

Administration and Combination Therapies

Any method known in the art may be used to administer an effective amount of a composition containing an antibody that specifically binds to an epitope containing N-acetylglucosamine or N-acetyl-galactosamine, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In some embodiments, the antibody is administered orally. In some embodiments, the composition contains an antibody that specifically binds to an epitope containing N-acetylglucosamine or N-acetyl-galactosamine and another protein, e.g., another antibody that does not specifically bind to an epitope containing N-acetylglucosamine or N-acetyl-galactosamine. An effective amount of a composition containing an antibody that specifically binds to an epitope containing N-acetylglucosamine or N-acetyl-galactosamine may be determined by any method known in the art and may depend upon a number of characteristics of the individual as described above.

Certain aspects of the present disclosure relate to methods for treating or preventing cancer in an individual by administering to the individual an effective amount of a composition containing an antibody that specifically binds to an epitope containing N-acetylglucosamine or N-acetyl-galactosamine and an amount of another anti-cancer agent, where the antibody and the anti-cancer agent in conjunction provide effective treatment or prevention of cancer in the individual. Any suitable anti-cancer agent known in the art may be used in combination with the antibodies described herein. Anti-cancer agents may include antibodies (including antibody-drug conjugates), small molecules, immunotherapeutics, differentiating agents, targeted therapies, and hormones.

In some embodiments, the anti-cancer agent is a chemotherapeutic agent. Many types of chemotherapeutic agents are known in the art. Examples of chemotherapeutic agents may include without limitation antimetabolites (e.g., 5-fluorouracil or capecitabine), anthracyclines, anti-tumor antibiotics (e.g., actinomycin-D, mitomycin-C, or bleomycin), mitotic inhibitors (e.g., taxanes such as Taxol® or epothilones), corticosteroids, topoisomerase inhibitors (e.g., etoposide), alkylating agents, and platinum drugs (e.g., cisplatin, oxalaplatin, or carboplatin). These drugs are provided as examples for one of skill in the art and are in no way intended to limit the choice of chemotherapeutic agents.

Gastrointestinal Disease and Rheumatoid Arthritis

Certain aspects of the present disclosure relate to methods for treating or preventing gastrointestinal disease in an individual by administering to the individual an effective amount of a composition containing an antibody that specifically binds to an epitope containing N-acetylglucosamine or N-acetyl-galactosamine. It is a surprising finding described herein that antibodies that specifically bind to an epitope containing N-acetylglucosamine or N-acetyl-galactosamine, expressed on a cell surface of an inflammatory cell, may be used to treat or prevent a wide range of gastrointestinal diseases, including autoimmune and infectious diseases.

As described herein, the methods of the present disclosure are effective against a wide range of gastrointestinal or autoimmune diseases in an individual. In some embodiments, the individual has inflammatory bowel disease. An inflammatory bowel disease of the present disclosure may be chronic or acute. As is known in the art, many gastrointestinal diseases such as inflammatory bowel disease may present symptoms in tissues including without limitation the small and large intestines, mouth, stomach, esophagus, and anus. In some embodiments, an inflammatory bowel disease may include colitis (such as diversion, lymphocytic, collagenous, or indeterminate colitis) or Behcet's disease.

In some embodiments, the individual has Crohn's disease. In some embodiments, the individual has ulcerative colitis. In some embodiments, the individual has acute infectious gastroenteritis. In some embodiments, the individual has a hemorrhoid. In some embodiments, the individual has rheumatoid arthritis.

In some embodiments, the individual has a gastrointestinal disease caused by a viral infection. Viruses known to cause gastrointestinal disease may include without limitation rotaviruses, noroviruses, adenoviruses, and astroviruses. In some embodiments, the viral infection is a rotaviral infection.

In some embodiments, the individual with a gastrointestinal or autoimmune disease is a human. In some embodiments, the individual with a gastrointestinal or autoimmune disease is a non-human animal.

Many suitable methods for administering a composition for treating or preventing a gastrointestinal or autoimmune disease are known in the art. In some embodiments, an antibody of the present disclosure may be administered intravenously, intramuscularly, subcutaneously, topically, orally, transdermally, intraperitoneally, intraorbitally, by implantation, by inhalation, intrathecally, intraventricularly, or intranasally.

Chimeric Antigen Receptor (CAR) T-Cell Therapy

Further exemplified herein (see, e.g., Example 5 below) is the use of any of the antibodies of the present disclosure in a CAR, e.g., for a CAR T-cell therapy. CAR T-cell therapy is known in the art as a therapeutic approach that utilizes the antigen-binding region of an antibody (e.g., a single chain variable fragment of scFv) fused to transmembrane and intracellular signal domains of a T-cell signaling molecule.

These CAR T-cells typically recognize antigen(s), e.g., unprocessed antigens, based on the specificity of the antibodies from which they are derived, thereby redirecting the T-cells for a therapeutic purpose, such as targeting tumor cells bearing a particular antigen, or redirecting Treg cells to block an inflammatory disease. For greater description, see, e.g., Dai, H. et al. (2016) *J. Natl. Cancer Inst.* 108(7): djv439.

Immunotherapy is a therapy that harnesses the power of a patient's immune system to combat their disease. One approach to immunotherapy involves engineering patients' own immune cells to recognize and attack their tumors. Although this approach, called adoptive cell transfer (ACT), has been restricted to small clinical trials so far, treatments using these engineered immune cells have generated some remarkable responses in patients with advanced cancer.

ACT's building blocks are T cells, a type of immune cell collected from the patient's own blood. After collection, the T cells are genetically engineered to produce special receptors on their surface called chimeric antigen receptors (CARs). CARs are proteins that allow the T cells to recognize a specific protein (antigen) on tumor cells. These engineered CAR-T cells are then grown in the laboratory, e.g., until they number in the billions. The expanded population of CAR-T cells is then infused into the patient. After the infusion, the T cells multiply in the patient's body and, with guidance from their engineered receptor, recognize and kill cancer cells that harbor the antigen on their surfaces.

N-acetylglucosamine and N-acetyl-galactosamine or glycoconjugates bearing distinct N-Acetyl glucosamine or N-acetyl-galactosamine moieties can be the harbor antigens on tumor cells and the antibodies recognize those antigens disclosed in the current and previous patents can be receptors for the tumor antigens. Thus one aspect of the current disclosure is to genetically engineering the genes encoding antibody K3, K4 and other antibodies recognizing N-acetylglucosamine and N-acetyl-galactosamine or glycoconjugates bearing distinct N-Acetyl glucosamine or N-acetyl-galactosamine moieties (e.g., an antibody fragment bearing antigen-binding fragments or heavy and/or light chain variable domains of such antibodies) into T cells from patients to produce CARs on the T cells. These engineered CAR-T cells can be used for the treatment of cancers and autoimmune diseases such as IBD and rheumatoid arthritis as described herein.

In some embodiments, a CAR comprises an antibody fragment comprising a light chain variable region comprising an HVR-L1 sequence of SEQ ID NO: 5, an HVR-L2 sequence of SEQ ID NO: 7, and an HVR-L3 sequence of SEQ ID NO: 9 and/or a heavy chain variable region comprising an HVR-H1 sequence of SEQ ID NO: 1, an HVR-H2 sequence of SEQ ID NO: 2, and an HVR-H3 sequence of SEQ ID NO: 3. In some embodiments, a CAR comprises an antibody fragment comprising a light chain variable region comprising an HVR-L1 sequence of SEQ ID NO: 5, an HVR-L2 sequence of SEQ ID NO: 8, and an HVR-L3 sequence of SEQ ID NO: 9 and/or a heavy chain variable region comprising an HVR-H1 sequence of SEQ ID NO: 1, an HVR-H2 sequence of SEQ ID NO: 2, and an HVR-H3 sequence of SEQ ID NO: 3.

Certain aspects of the present disclosure relate to chimeric antigen receptors (CARs). In some embodiments, the CAR specifically binds to an epitope comprising N-acetylglucosamine or N-acetyl-galactosamine. In some embodiments, the CAR comprises a light chain variable region comprising an HVR-L1 sequence of SEQ ID NO: 5, an HVR-L2 sequence of FTSX$_1$LX$_2$S (SEQ ID NO: 25), and an HVR-L3 sequence of SEQ ID NO: 9, wherein X$_1$ is T or S and X$_2$ is Q or E and/or a heavy chain variable region comprising an HVR-H1 sequence of SEQ ID NO: 1, an HVR-H2 sequence of SEQ ID NO: 2, and an HVR-H3 sequence of SEQ ID NO: 3. In some embodiments, the HVR-L2 sequence comprises the amino acid sequence of SEQ ID NO: 7 or SEQ ID NO: 8. In some embodiments, the CAR specifically binds to an epitope comprising N-acetylglucosamine and an epitope comprising N-acetyl-galactosamine.

In some embodiments, the CAR comprises a light chain variable region comprising the amino acid sequence of SEQ ID NO: 14 or SEQ ID NO:26. In some embodiments, the CAR comprises a light chain variable region comprising the amino acid sequence of SEQ ID NO: 13.

In some embodiments, the CAR comprises a heavy chain variable region comprising the amino acid sequence of SEQ ID NO: 10 or SEQ ID NO: 33.

In some embodiments, the light chain variable region and/or the heavy chain variable region are humanized or human.

As is known in the art, CARs typically include one or more polypeptide domains that potentiate T-cell receptor signaling, such as the CD3 zeta and/or CD28 endodomains (see, e.g., Maher, J. et al. (2002) *Nat. Biotechnol.* 20:70-75 and Savoldo, B. et al. (2011) *J. Clin. Invest.* 121:1822-1826). In some embodiments, the CAR comprises a human CD3 zeta (also known as CD247) endodomain sequence. In some embodiments, human CD3 zeta refers to a polypeptide encoded by the human CD247 gene, e.g., as described by NCBI RefSeq Gene ID No. 919 and/or UniProt Accession No. P20963. In some embodiments, the CAR further comprises a human CD28 endodomain sequence. In some embodiments, human CD28 refers to a polypeptide encoded by the human CD28 gene, e.g., as described by NCBI RefSeq Gene ID No. 940 and/or UniProt Accession No. P10747.

In some embodiments, the CAR comprises, from N-terminus to C-terminus, the heavy chain variable region, a linker, the light chain variable region, a CD8 hinge region, a human CD28 endodomain, and a human CD3 zeta endodomain. For example, in certain embodiments, the CAR comprises the amino acid sequence of SEQ ID NO: 34.

As demonstrated herein, a CAR of the present disclosure, when expressed by a T cell (e.g., on the cell surface) is able to induce tumor cell killing. For example, the CAR can bind an epitope (e.g., comprising N-acetylglucosamine and/or N-acetyl-galactosamine) expressed on a cell surface of a cancer cell (e.g., a cancer cell of the present disclosure). In some embodiments, binding of the CAR to the epitope expressed on the cell surface of the cancer cell leads to killing of the cancer cell by the T cell.

Further provided herein are isolated polynucleotides comprising a nucleic acid sequence encoding a CAR of the present disclosure. Also provided are vectors comprising a nucleic acid sequence encoding a CAR of the present disclosure. In some embodiments, the vector is a viral vector. Various types of viral vectors are known in the art and include without limitation lentiviral, adenoviral, adeno-associated viral (AAV), herpes simplex viral (HSV) vectors. Yet further provided are isolated T cells (e.g., human T cells) comprising a nucleic acid sequence encoding a CAR of the present disclosure and/or expressing a CAR of the present disclosure, e.g., on their cell surface.

The CARs of the present disclosure (as well as the isolated polynucleotides, vectors, and isolated T cells related thereto) may find use in a method of treatment of the present disclosure, such as the methods of treating or preventing cancer described herein. As such, provided herein are methods for treating or preventing cancer in an individual, comprising administering to the individual an effective amount of a composition comprising a T cell of the present disclosure, e.g., a T cell that expresses a CAR of the present disclosure. In some embodiments, the cancer is a type of cancer described herein, including without limitation a cancer selected from the group consisting of pancreatic cancer, colorectal cancer, esophageal cancer, leukemia, adenocarcinoma, fibrosarcoma, duodenal adenocarcinoma, brain cancer, liver cancer, lung cancer, breast cancer, ovarian cancer, and cervical cancer. In certain embodiments, the cancer is pancreatic cancer, colorectal cancer, lung cancer, or brain cancer, including the subtypes thereof described herein. In some embodiments, the individual is a human.

In some embodiments, the methods further include administering another anti-cancer agent, such as those described in reference to combination therapies herein. In some embodiments, the T cell and the anti-cancer agent in conjunction provide effective treatment or prevention of cancer in the individual. In some embodiments, the anti-cancer agent is a chemotherapeutic agent.

VIII. Methods of Detection

Certain aspects of the present disclosure relate to methods for detecting the presence of cancer cells in an individual by: obtaining a biological sample from an individual, contacting the biological sample with an antibody that specifically binds to an epitope containing N-acetylglucosamine or N-acetyl-galactosamine, and detecting the amount of antibody binding to the biological sample, where antibody binding indicates the presence of cancer cells in the individual. Advantageously, the present disclosure describes how an antibody that specifically binds to an epitope containing N-acetylglucosamine or N-acetyl-galactosamine may be used to detect the presence of a cancer in an individual, due to the correlation between elevated levels of N-acetylglucosamine or N-acetyl-galactosamine in a serum sample and the presence of a cancer. These methods may be used to detect many types of cancer, including without limitation lung cancer, liver cancer, breast cancer, colon or colorectal cancer, esophageal cancer, stomach cancer, endometrial cancer, cervical cancer, thyroid cancer, brain cancer, and lymphoma.

Specific binding between the antibody and an epitope containing N-acetylglucosamine or N-acetyl-galactosamine may be detected by any method known in the art. Methods for detecting binding between an antibody and an epitope are well known in the art and may include an ELISA (enzyme-linked immunosorbent assay) immunohistochemistry (IHC) assays, immunofluorescence assays. flow cytometry, CTC (Circulating tumor cells) assays, and immuno-colloidal gold assays. These exemplary assays are well known to one of skill in the art; for more detailed descriptions, see, e.g., Harlow and Lane, eds. (1988) *Antibodies, A Laboratory Manual*. Examples of ELISAs may include direct, indirect, competitive, and sandwich ELISAs. Any surface may be used, including without limitation a plate (e.g., a 96-well plate) or a column.

In some embodiments, the amount of antibody binding to an epitope containing N-acetylglucosamine or N-acetyl-galactosamine detected as described above may be compared with an amount of antibody binding detected using a control sample. An increased amount of antibody binding to the biological sample may indicate the presence of cancer cells in the individual, as compared to the amount of antibody binding to the control sample. A control sample may be processed as described above with the biological sample from the individual to be tested. Examples of control samples may include a sample from a cancer-free individual, or a sample with a known quantity of N-acetylglucosamine and/or N-acetyl-galactosamine. As a non-limiting example, serum from a test individual may be tested using the methods described herein and compared with serum from a healthy (i.e., cancer-free) individual. In this scenario, increased antibody binding in the serum from the test individual, compared to the healthy individual or the serum with a known quantity of N-acetylglucosamine and/or N-acetyl-galactosamine, may indicate the presence of cancer cells in the test individual.

Any body fluid or section may be used as a biological sample of the present disclosure. Examples of biological samples may include without limitation blood, serum, urine, feces, milk, semen, saliva, chest fluid, abdominal fluid, cerebrospinal fluid, sputum, and any other body fluid or secretion.

As shown herein, many types of cancer cells may be detected in an individual using the methods described herein. Examples of cancer cells that may be detected in an individual include without limitation lung cancer cells, liver cancer cells, breast cancer cells, colon or colorectal cancer cells, esophageal cancer cells, stomach cancer cells, endometrial cancer cells, cervical cancer cells, thyroid cancer cells, brain cancer cells, and lymphoma cells.

In addition, saccharide-related biomarkers themselves may be used in the detection of auto-antibodies in subjects with cancers or other diseases. These auto-antibodies may bind to the saccharides that are differentially expressed on or in those cancerous or otherwise diseased tissues or cells, or released to blood, urine, feces, milk, semen, saliva, and body fluid or secretions. Body fluid or secretions may include but not limited to chest fluid, abdomen fluid, cerebrospinal fluid, sputum, and organ smears. In some embodiments, saccharide-related biomarkers may include without limitation N-Acetyl-Glucosamine, N-Acetyl-Galactosamine or fucose, or glycoconjugates bearing distinct N-Acetyl glucosamine, N-Acetyl-Galactosamine or fucose.

IX. Kits

Certain aspects of the present disclosure relate to kits containing a pharmaceutical composition containing an antibody that specifically binds to an epitope containing N-acetylglucosamine or N-acetyl-galactosamine. In some embodiments, the kits may further include instructions for administering an effective amount of the pharmaceutical composition to an individual for treating cancer. These instructions may refer to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

Suitable containers for a kit of the present disclosure include, for example, bottles, vials (e.g., dual chamber vials), syringes (such as single or dual chamber syringes) and test tubes. The article of manufacture may further comprise a label or a package insert, which is on or associated with the container, may indicate directions for reconstitution and/or use of the formulation. The label or package insert may further indicate that the formulation is useful or intended for oral or other modes of administration for treating or preventing cancer in an individual. The article of manufacture may further include other materials desirable from a commercial, therapeutic, and user standpoint, including other buffers, diluents, filters, needles, syringes, and package inserts with instructions for use.

In some embodiments, the kits containing a pharmaceutical composition containing an antibody that specifically binds to an epitope containing N-acetylglucosamine or N-acetyl-galactosamine may further contain instructions for detecting the presence of cancer cells in an individual. These instructions may refer to instructions customarily included in commercial packages of ELISA assay kits, immunohistochemistry (IHC) assay kits, immunofluorescence assay kits, flow cytometry assay kits, CTC (Circulating tumor cells) assay kits, and immuno-colloidal gold assay kits. A kit of the present disclosure may also contain any other reagents useful for detecting the presence of cancer cells in an individual, such as 96-well microtiter plates, a non-specific protein such as bovine serum albumin, a secondary antibody that binds to an antibody of the present disclosure without affecting its antigen-binding, and reagents for detection, such as a fluorescent or luminescent label, or an enzyme and substrate that produce a detectable signal (e.g., horseradish peroxidase and TMB).

Certain aspects of the present disclosure relate to kits containing a pharmaceutical composition containing N-acetylglucosamine or N-acetyl-galactosamine and instructions or other reagents for using the pharmaceutical composition for detecting the presence of an auto-antibody in an individual with cancer or inflammation. These instructions may refer to instructions customarily included in commercial packages of ELISA assay kits, immunohistochemistry (IHC) assay kits, immunofluorescence assay kits, flow cytometry assay kits, CTC (Circulating tumor cells) assay kits, and immuno-colloidal gold assay kits. A kit of the present disclosure may also contain any other reagents useful for detecting the presence of cancer cells in an individual, such as 96-well microtiter plates, a non-specific protein such as bovine serum albumin, a secondary antibody that binds to an antibody of the present disclosure without affecting its antigen-binding, and reagents for detection, such as a fluorescent or luminescent label, or an enzyme and substrate that produce a detectable signal (e.g., horseradish peroxidase and TMB).

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Binding of Humanized Antibodies to N-Acetyl-Glucosamine and N-Acetyl-Galactosamine The identification of biomarkers that are preferentially expressed by cancer cells, rather than normal human cells, may allow for the design of new assays and therapeutic approaches to aid in the diagnosis, treatment, and/or prevention of cancer. To meet this demand, described herein are monoclonal antibodies that bind to N-acetylglucosamine and N-acetyl-galactosamine.

Mab-1C5C9 was previously demonstrated to be efficacious in inhibiting cancer cell growth, detecting circulating cancer cells, and treating IBD (see PCT/CN2015/087717). MAb-1C5C9 was subsequently humanized. Variants (1C5-VK1 and 1C5-VK2) of humanized 1C5C9 with a common heavy chain variable region (VH) and different light chain variable regions (VK) were characterized. Humanized 1C5C9 antibodies were tested for efficacy, binding, and toxicity in multiple in vivo animal models of IBD as described in PCT/CN2015/087717.

Provided herein are new variants of humanized 1C5C9, 1C5-VK3 ("VK3") and 1C5-VK4 ("VK4"). These antibodies were tested for binding and efficacy in multiple in vivo animal models of IBD, arthritis and cancers as described in following Examples.

Materials and Methods
Characterization of Binding

100 μL of N-acetyl-glucosamine (NAcGlu or NAG) and N-acetyl-galactosamine (NAcGal) were separately coated onto the wells of a 96-well plate at the concentration of 1 μg/mL overnight, then washed and blocked. Humanized antibody clones 1C5-VK3 (K3) and 1C5-VK4 (K4) were tested.

After adding the test antibodies to the plate, the plate was washed, and binding was detected by HRP-conjugated anti-human IgG as a secondary reagent. HRP was detected by standard chromogenic assay, and binding was assayed by $OD_{450\ nm}$. In another test, each of the antibodies was pre-mixed with 20 μL of each NAcGlu and NAcGal at 1 μg/mL for 15 minutes before being added to a plate coated with NAcGlu. The rest of the test was as same as described above.

Mouse IBD Model

Acute colitis was induced in BALB/c female mice, aged 6-8 weeks and weighing 17-19 grams, by anal administration of a 0.15 mL dose of 120 mg/mL trinitrobenzenesulphonic acid (TNBS; Sigma-Aldrich) in 50% ethanol. Mice were divided into 5 treatment groups as follows:

G1: untreated (n=5);
G2: treated with 200 μg antibody Adalimumab (Humira) (Vetter Pharma-Fertigung GmbH & Co. KG) per animal, intraperitoneally (IP) (n=5);
G3: treated with 5 μg antibody K3 per animal, intraperitoneally (IP) (n=5); and
G4: treated with 5 μg antibody K4 per animal, intraperitoneally (IP) (n=5).

The treatment of G2-G4 mice was dosed once per day for 4 days from 48 hours after induction of IBD by TNBS.

Figure 4:
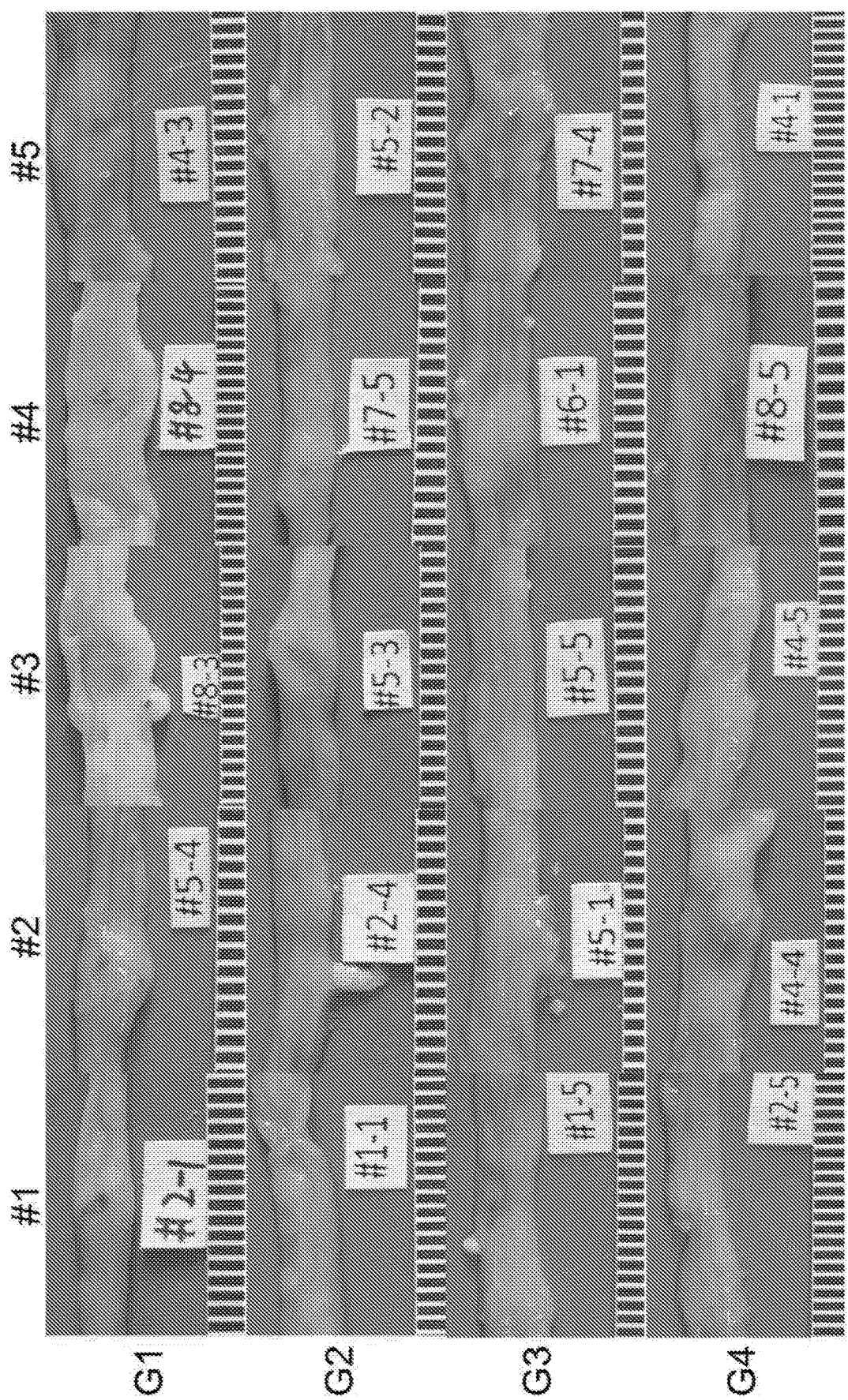
FIG. 4 shows representative gross images taken at day 7 of the IBD model induced by TNBS. Treatment with test antibodies was given at 48 hours after the induction of the IBD model. Treatment groups are as described above for FIG. 3.

Body weight and clinical signs of mice in each group were recorded each day of the IBD model. Two mice from the control group (G1) were sacrificed at 48 hours after the induction of the IBD model by TNBS, and whole colon tissues were collected. One day (24 hrs) after the last dosing, the procedure was ended for all animals (day 7 of the course). Whole colon tissue was collected for gross pathology (colon weight, ulceration) and histology evaluation (standard HE staining of colon tissue sections) according to the key shown in Table 1 below, and representative images were taken. Colon tissue pathology was evaluated using standard histological methods as shown in FIG. 4.

TABLE 1

Scoring legend for macroscopic colon tissue assessment.

| Score | Phenomenon |
| --- | --- |
| 0 | No damage |
| 1 | Hyperemia without ulcers |
| 2 | Hyperemia and thickening of bowel wall without ulcers |
| 3 | One site of ulceration with bowel wall thickness |
| 4 | Two or more sites of ulceration and inflammation |
| 5 | 0.5 cm inflammation and major damage |
| 6-10 | 1 cm major damage. The score is increased by one for every 0.5 cm damage observed, to a maximum of 10 |

Collagen-Induced Arthritis (CIA) Model

Lewis rats at about eight weeks old were immunized once per week for three weeks using bovine type II collagen as an immunogen. The rats with significant inflammatory swelling joints were randomly divided into three groups:

Group 1 (G1): control, not treated, n=5;
Group 2 (G2): treated with antibody 1C5-VK2 ("K2") at 250 µg/kg once every other day, intravenously, n=5; and
Group 3 (G3): treated with antibody K3 at 250 µg/each once every other day, intravenously, n=5.

The paw volume and body weight were measured twice a week; and representative images were taken once per week. One day (24 hrs) after the last dosing, the procedure was ended for all animals (day 28 post dosing). Ankle and knee tissues were collected for histology evaluation including the status of synovia, cartilage, and bone; thymus and spleen were collected, weighed and calculated for organ coefficient. Blood was also collected and serum was isolated.

Patient-Derived Xenograft (PDX) Model of Pancreatic Cancer

A Patient-Derived Xenograft (PDX) mouse model of pancreas cancer was used for evaluation of the anti-tumor efficacy of antibody-K4. The PDX model was developed using Nu/Nu mice (6 weeks) and the human tumor tissue from a 47 years old female patient suffering from primary poorly differentiated pancreas ductal adenocarcinoma without any treatment.

In Vitro Tests

A CellTiter-Glo (CTG) Luminescent Cell Viability Assay was performed. Briefly, K3 and K4 were cultured for 6 days with tumor cells from the PDX-P3 tumor tissue of the pancreas cancer model as described above; then CTG reagents was added, and the fluorescent signal was read according to manufacturer's instructions (Promega, Madison, USA). The tumor cells alone were used as control. The inhibition rate of cellular growth was calculated by comparison between control and each test group.

In Vivo Tests

The PDX-P pancreas tissue was inoculated into Nu/Nu mice at 6 weeks old for 16 days. The mice with the tumor volume at about 200 mm$^3$ were randomly divided into three groups: group 1 (G1): control, not treated; group 2 (G2): treated with antibody K4 at 50 µg/each once every other day; group 3 (G3): treated with a mouse antibody at 100 µg/each once every other day. The tumor size (volume) and mouse body weight were measured twice a week. The tumors were collected at day 37 post administration and measured. The TGI was calculated by the formula $$TGI\% = [1-(Ti-T0)/(Vi-V0)] \times 100$$

Wherein T represents tumor size of test group; V represents tumor size of control group; zero means tumor size before administration; "i" represents a time point.

Patient-Derived Xenograft (PDX) Model of Colorectal Cancer

In Vitro Tests

K3 was cultured for 6 days with tumor cells of a PDX-P3 rectal tumor tissue from a 67 years old male with moderately differentiated colon adenocarcinoma. Then the CTG reagents was added, and the fluorescent signal was read according to manufacturer's instructions. The tumor cells alone were used as control. The inhibition rate of cellular growth was calculated by comparison between control and each of test group.

In Vivo Tests

A mouse PDX model of rectal cancer was developed using NCG mice (6 weeks) and the human tumor tissue from a 47 years old male patient with primary poorly differentiated rectal adenocarcinoma without any treatment. The PDX-P2 rectal tissue was inoculated into NCG mice at 6 weeks old for 22 days. The mice with the tumor volume at about 80-100 mm$^3$ were randomly divided into three groups: group 1 (G1): control, not treated; group 2 (G2): treated with antibody K3 at 50 µg/each once every other day; group 3 (G3): treated with antibody K4 at 50 µg/each once every other day. The tumor size (volume) and mouse body weight were measured twice a week. The tumors were collected at day 17 post administration and measured. The TGI was calculated by the formula described above.

In Vitro Binding of Antibodies to Tumor Cells

An ELISA assay was developed for detection of the binding of monoclonal antibodies to human tumor cells. Briefly, a 96-well tissue-culture plate with human tumor cells was incubated until about 90% confluence. Then the medium was removed and replaced with 100 µL fresh culture medium without serum, the medium was discarded, and the plate was stored without cover at 4° C. until the plate dried. The plate was sealed until use in a binding test.

For the ELISA assay, 100 µl/well antibody K3 and K4 was added in duplicate to the 96-well plates coated with human tumor cells as mentioned above and incubated for one hour at room temperature. This was washed and horseradish peroxidase (HRP)-conjugated anti-human IgG was used as secondary reagent, and TMB (3,3',5,5'-tetramethylbenzidine) Peroxidase EIA Substrate Kit (Bio-Rad, Hercules, Calif., USA) was used for the detection of the HRP-labeled antibodies. The plates were read by an ELISA reader at OD$_{450}$. Phosphate buffered saline (PBS) was used as a negative control.

Results

FIGS. 1A & 1B show that both antibodies displayed dose-dependent binding to NAcGlu (FIG. 1A) and NAcGal (FIG. 1B). FIG. 2 shows that the binding of K3 and K4 was inhibited by pre-treatment with NAcGlu and NAcGal. These results demonstrate that K3 and K4 specifically recognize N-acetyl-glucosamine and N-acetyl-galactosamine. The two humanized antibodies K3 and K4 were further characterized as described infra.

Example 2: Testing Efficacy of Humanized Antibodies to N-Acetyl-Glucosamine and N-Acetyl-Galactosamine in Mouse IBD and Rat CIA Models Mouse and rat models of IBD are used to explore disease pathogenesis and validate therapeutic targets. Acute colitis was induced in mice as described above, and the effect of humanized K3 and K4 administration on body weight, clinical signs such as diarrhea, and colon condition was tested and compared to the effect of Adalimumab. The effect of antibody treatment was assayed by macroscopic assessment of colon conditions according to the key provided in Table 1 above. Colons from mice in treatment groups G1-G4 were assessed for the presence of colitis, as shown in FIG. 4.

FIG. 3 shows that treatment with K3 (G3) resulted in a significant decrease in score as compared to untreated controls, demonstrating that antibody K3 treatment resulted in significant mitigation of ulceration and inflammation. It should be noted that treatment with Adalimumab (G2) did not show significant mitigation of ulceration and inflammation.

Representative gross images taken from these colon samples are shown in FIG. 4. All the untreated mice of control group (G1) showed colitis with ulceration, inflammation, and tissue necrosis. In group G2, one case (#1) showed thickening of the bowel wall without ulceration and inflammation, while four cases (#2, 3, 4 and 5) showed colitis with ulceration or inflammation or both. In group G3, two cases (#1 and #2) showed thickening of the bowel wall, light inflammation without significant ulceration, while 3 samples (#3, 4, and 5) showed no ulceration and inflammation. In group G4, three cases (#1, 2, 4 and 5) showed thickening of the bowel wall without ulceration and light inflammation.

These results illustrate that K3 treatment resulted in significant mitigation of ulceration and inflammation. Although K4 treatment demonstrated improvement the microscopic assessment score did not show statistically significant. The results also indicated that both K3 and K4 demonstrated better efficacy than Adalimumab.

Mouse and rat models of collagen-induced arthritis (CIA) are used to explore disease pathogenesis of rheumatoid arthritis and validate therapeutic targets. The chief pathological features of CIA include a proliferative synovitis with infiltration of polymorphonuclear and mononuclear cells, pannus formation, cartilage degradation, erosion of bone and fibrosis. The development of the disease is accompanied by a robust T-cell and B-cell inflammation response to type II collagen. Disease activity is determined by measuring inflammation swelling in the affected joints (paw volume or thickness) over time.

Figures 5A, 5B:
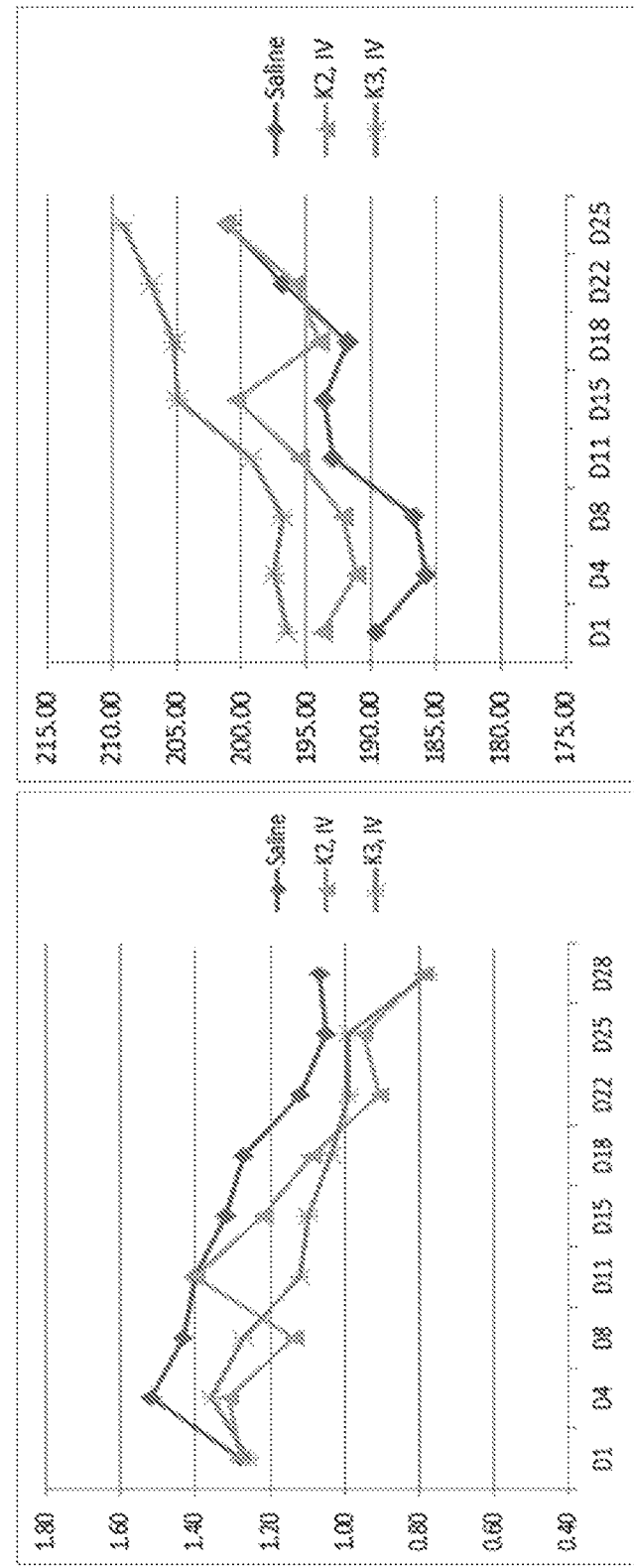
FIGS. 5A & 5B show the effects of humanized VK2 and VK3 antibody on paw swelling volume (FIG. 5A) and total body weight (FIG. 5B) in a rat collagen-induced arthritis model, as compared to saline treatment. Treatment groups include G1: untreated (n=5); G2: antibody VK2 ("K2") at 250 µg/kg once every other day, intravenously (n=5); G3: antibody VK3 ("K3") at 250 µg/each once every other day, intravenously (n=5).

A rat CIA model was used, as described above. As shown in FIGS. 5A & 5B and FIG. 6B, treatment with antibody VK3 significantly reduced the inflammatory severity of rat ankles and knees compared to those of controls. VK3 also reduced inflammation better than antibody VK2.

Figure 6A:
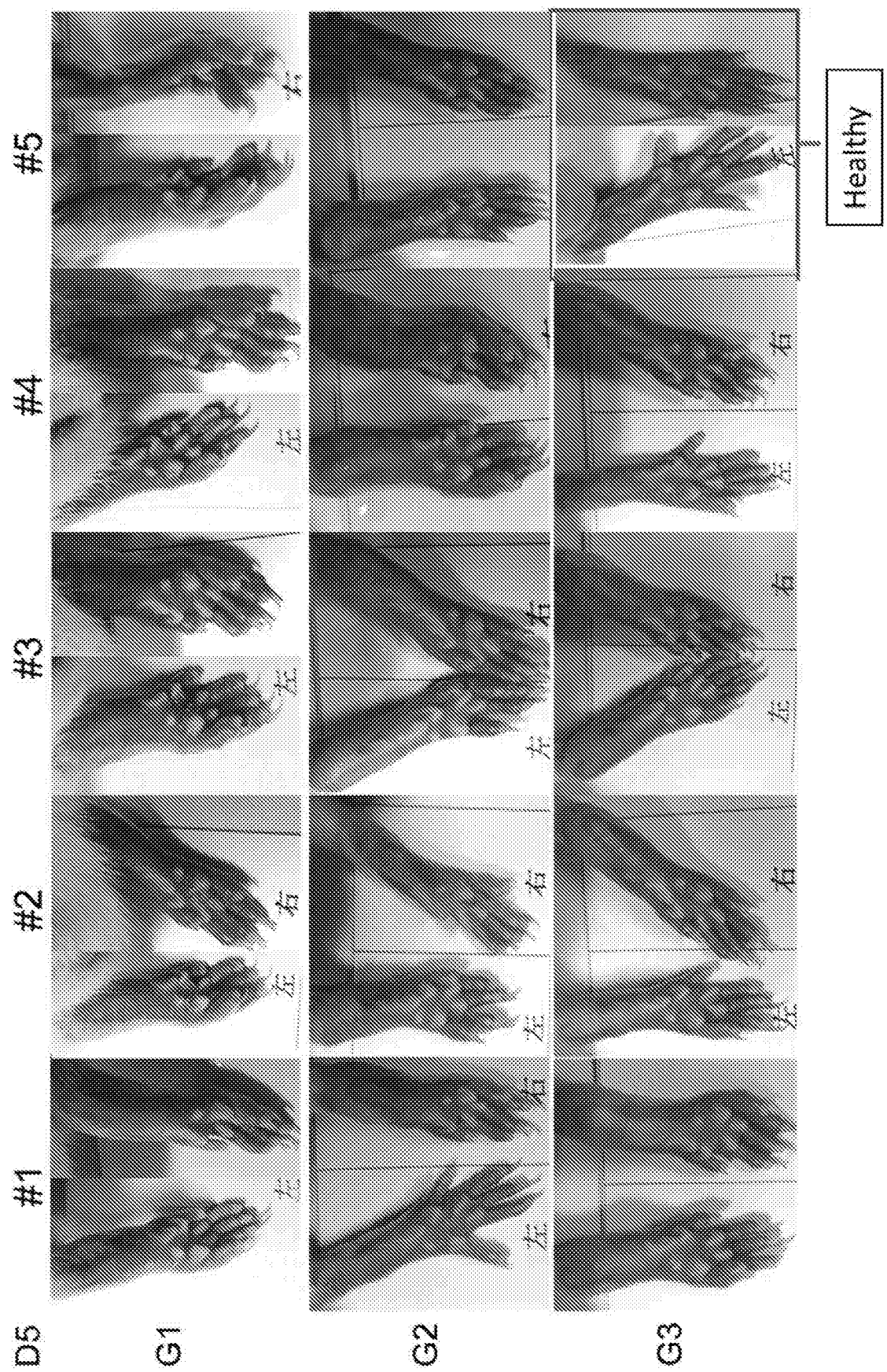
FIGS. 6A & 6B show representative gross images taken at day 5 post-dosing (i.e., after 2 doses.
Figure 6B:
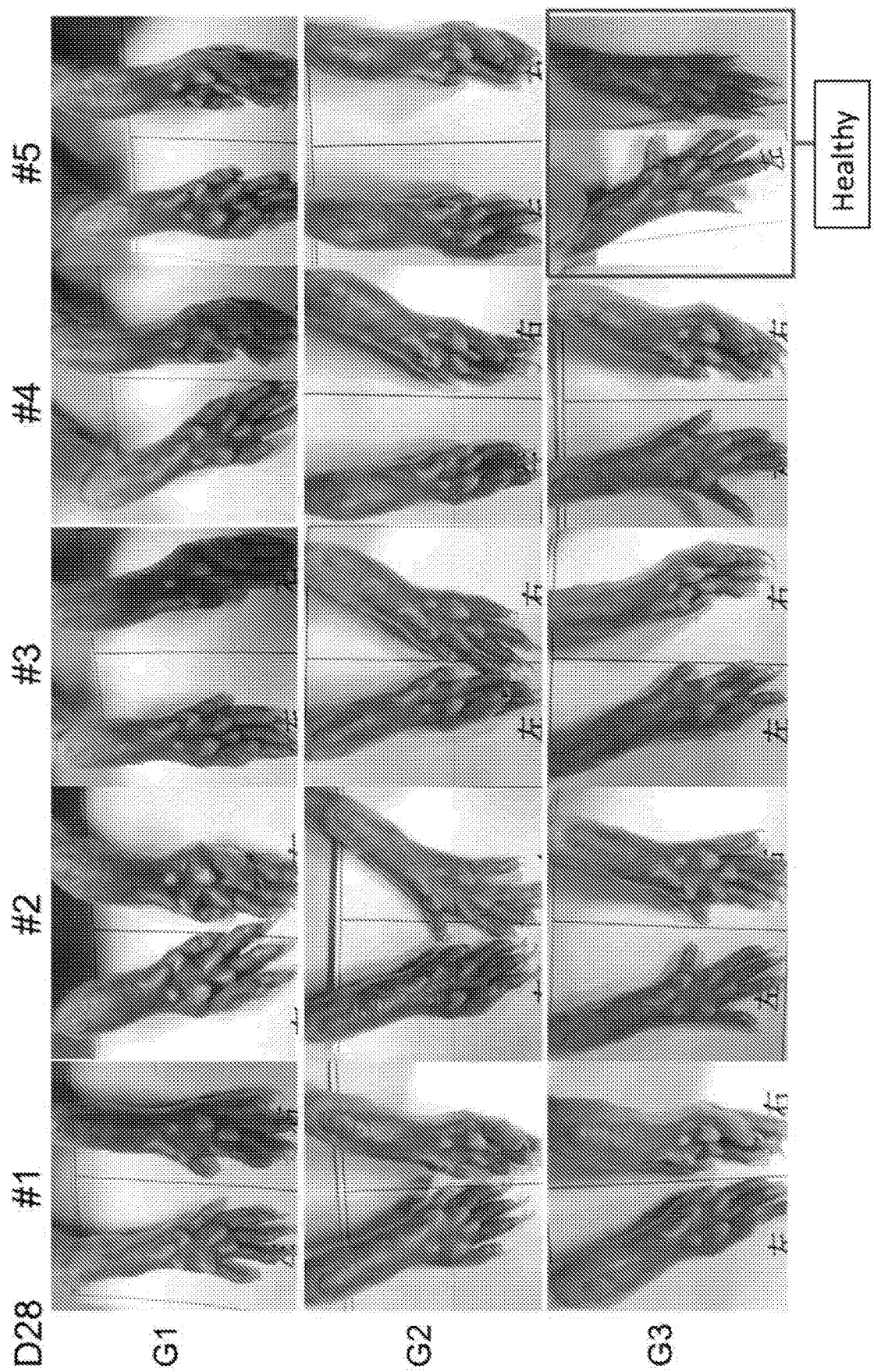

Representative gross images are shown in FIGS. 6A & 6B. FIG. 6A shows representative gross images taken at day 5 post dosing (after 2 dosing). All rat ankles and knees were swelling, red and hot. All rats walked with dragged legs. FIG. 6B shows representative gross images taken at day 28 post dosing (after 14 dosing).

These results demonstrate the efficacy of K3 in K4 in IBD and arthritis models of inflammatory disease.

Figure 7A:
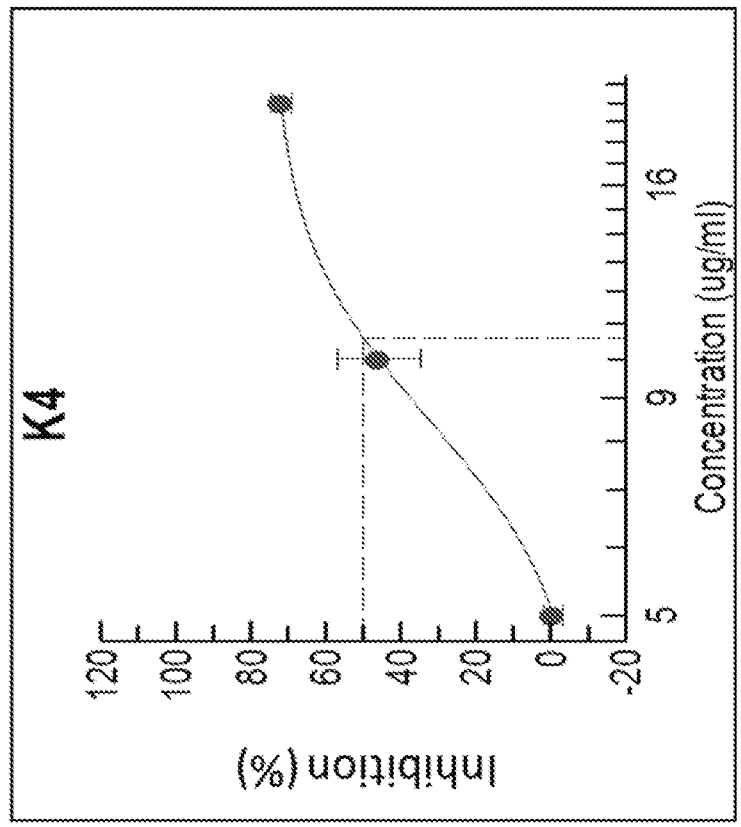
FIGS. 7A & 7B show the percentage of inhibition that the antibodies VK3 (FIG. 7A; "K3") and VK4 (FIG. 7B; "K4") demonstrated on cellular growth of a PDX-P3 pancreatic cancer model at various concentrations, as indicated.
Figure 7B:
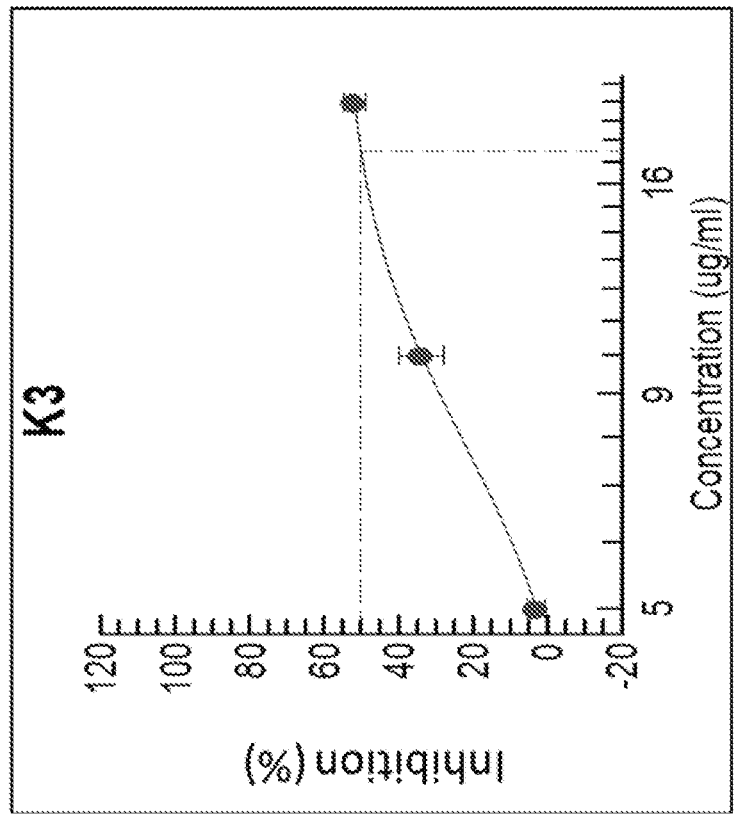

Example 3: Testing Efficacy of Humanized Antibodies to N-Acetyl-Glucosamine and N-Acetyl-Galactosamine in PDX Cancer Models A PDX model for pancreatic cancer was used for testing K3 and K4, as described above. The results of the in vitro tests are as follows. As shown in FIGS. 7A & 7B, antibodies K3 (FIG. 7A) and K4 (FIG. 7B) were able to inhibit cellular growth of PDX-P3 pancreatic cancer cells at various concentrations. Antibodies K3 and K4 (at the concentration of 20 µg/ml) inhibited the growth of the pancreas tumor cells at 51.7% and 71.8% respectively.

The results of the in vivo tests are as follows. As shown in FIGS. 8A-8C, antibody K4 inhibited tumor growth at about 62% at the end point of the test. K4's efficacy against tumor growth was demonstrated in assaying tumor volume over time (FIG. 8A), TGI (FIG. 8B), and macroscopic assessment of tumors (FIG. 8C).

Figure 9:
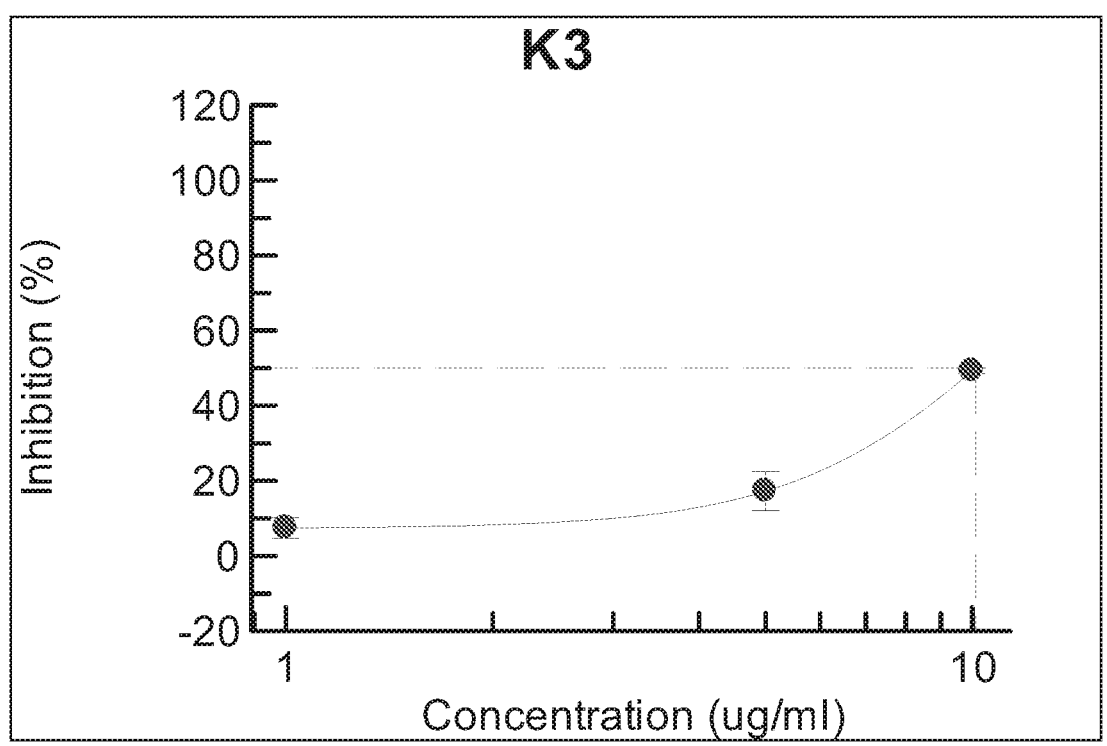
FIG. 9 shows the percentage of inhibition that the antibody VK3 ("K3") demonstrated on cellular growth of a PDX-P3 rectal cancer model at various concentrations, as indicated.

A PDX model for colorectal cancer was next used for testing K3 and K4, as described above. The results of the in vitro tests are as follows. As shown in FIG. 9, antibody K3 (at the concentration of 10 µg/ml) inhibited the growth of the rectal tumor cells at 49.6%.

Figure 10B:
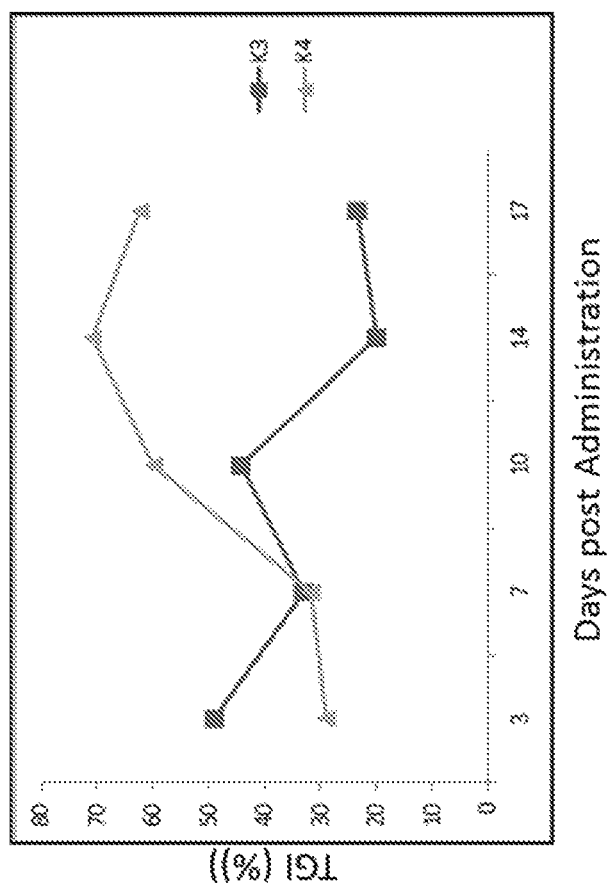
FIGS. 10A & 10B show the effects of treatment with antibody VK3 ("K3") or VK4 ("K4") on tumor volume (FIG. 10A) and tumor growth inhibition (TGI.
Figure 10A:
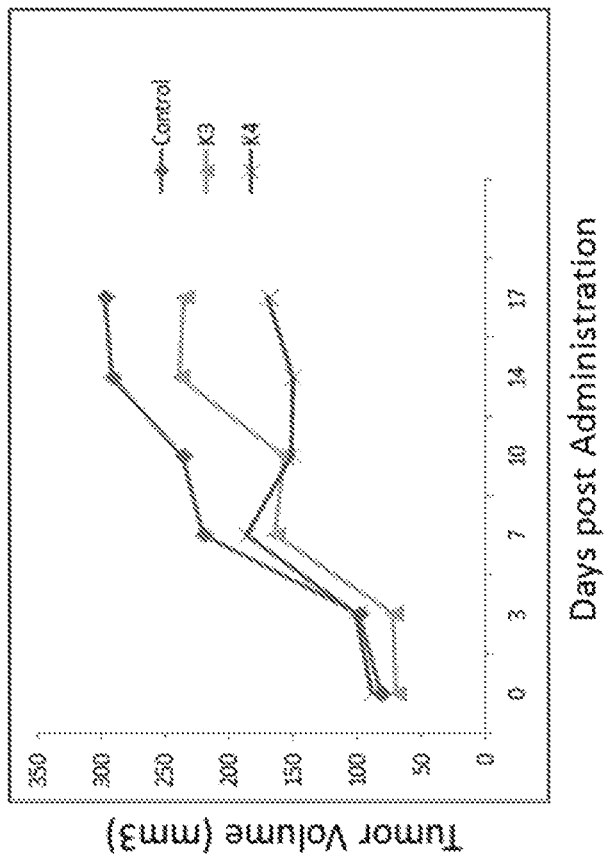

The results of the in vivo tests are as follows. As shown in FIGS. 10A & 10B, antibodies K3 and K4 inhibited the tumor growth at about 23% and 63% respectively at the end point of the test. These results demonstrate the efficacy of K3 and K4 in inhibiting tumor growth in vitro and in vivo, using multiple tumor models.

Example 4: In Vitro Binding of Humanized Antibodies to N-Acetyl-Glucosamine and N-Acetyl-Galactosamine to Tumor Cell Lines The ELISA-based assay described above was used to characterize the binding of humanized monoclonal antibodies K3 and K4 to human tumor cells. Antibodies K3 and K4 were tested for reactivity against various human tumor cell lines including NCI-H446 (small cell lung cancer), H1299 (non-small cell lung carcinoma), ECAP-1090 (esophageal adenocarcinoma), Jurkat (acute T cell leukemia), ACC-2 (adenoid cystic carcinoma cells), HT1080 (fibrosarcoma), HUTU80 (duodenum adenocarcinoma), MCF-7 (breast carcinoma) and Hela (cervical cancer).

Figure 11:
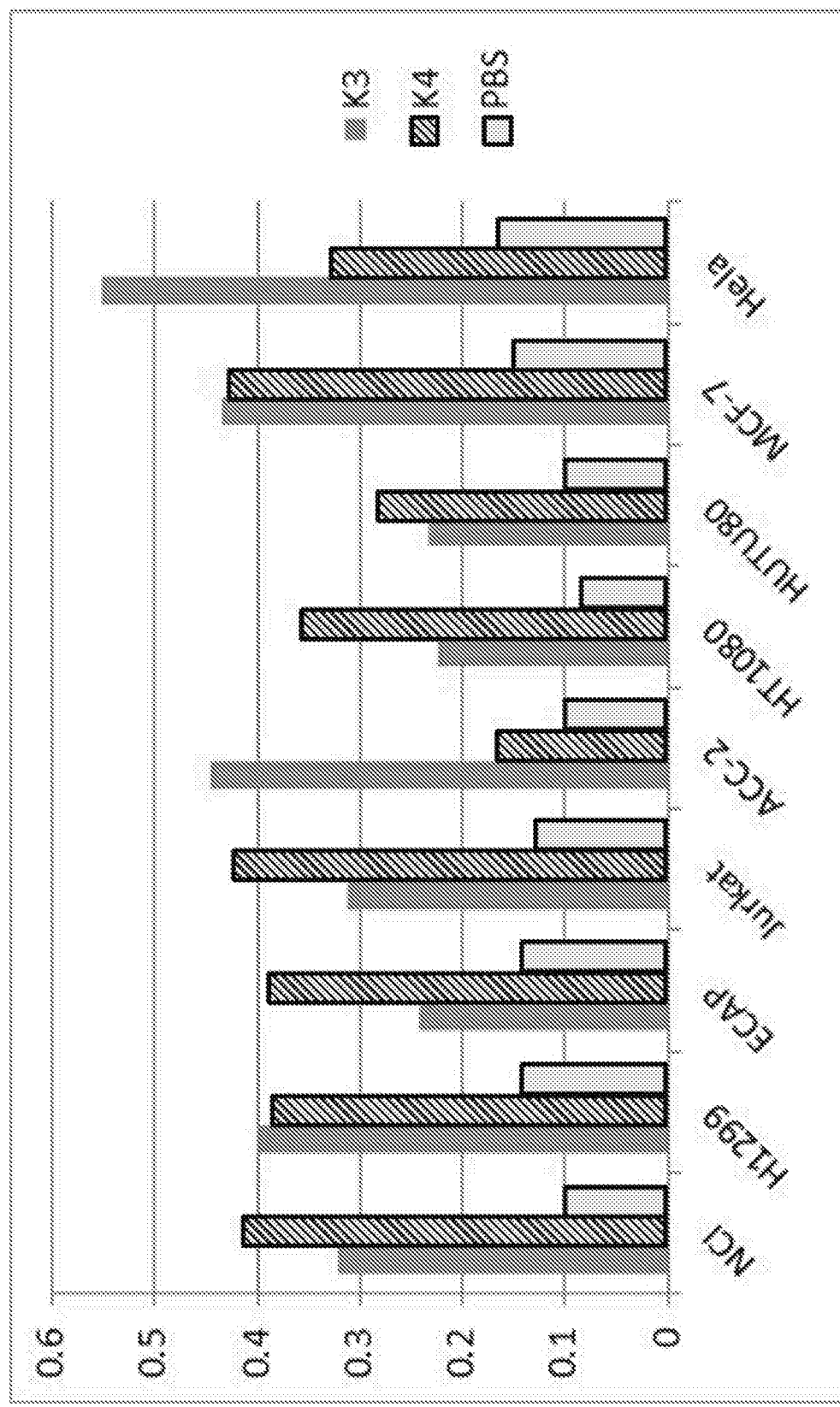
FIG. 11 shows the reactivity of antibodies VK3 ("K3") and VK4 ("K4"), compared to a negative control (phosphate buffered saline, PBS) against various human tumor cell lines, as indicated. Cell lines tested include: NCI-H446 (small cell lung cancer), H1299 (non-small cell lung carcinoma), ECAP-1090 (esophageal adenocarcinoma; Jurkat (acute T cell leukemia), ACC-2 (adenoid cystic carcinoma cells), HT1080 (fibrosarcoma), HUTU80 (duodenum adenocarcinoma), MCF-7 (breast carcinoma) and Hela (cervical cancer).

Both humanized monoclonal antibodies K3 and K4 were capable of binding human tumor cells, as shown in FIG. 11. Without wishing to be bound to theory, these results may suggest that the tumor antigens listed in FIG. 11 either include N-acetylglucosamine and/or N-acetyl-galactosamine, or include glycoconjugates bearing distinct N-Acetyl glucosamine or N-acetyl-galactosamine moieties. These results show that K3 and K4 are capable of binding a wide range of human tumor cell types.

Example 5: Tumor Cell Killing by T Cells Bearing Chimeric Antigen Receptor

The heavy chain and light chain variable domains from antibody K4 described above were reformatted for use in a chimeric antigen receptor (CAR) in order to test whether a CAR-T cell with this specificity would be able to effect T cell-mediated killing of cancer cells, e.g., tumor cell lines expressing N-acetylglucosamine and/or N-acetyl-galactosamine.

Construction and Generation of Lentiviral Vector

Figure 12A:
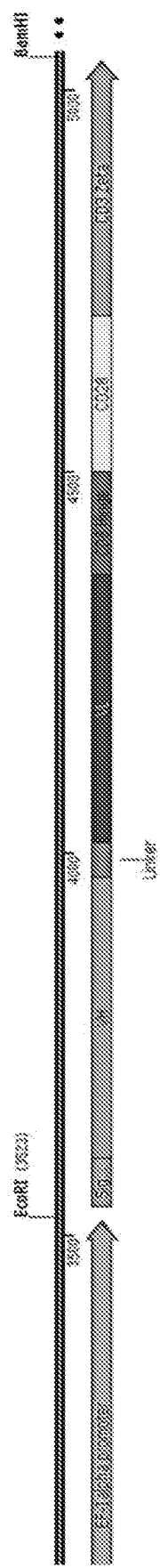
FIG. 12A shows a vector map of the lentiviral chimeric antigen receptor (CAR) vector used to generate CAR-T cells.

A full-length CAR bearing VH (SEQ ID NO:33) and VL (SEQ ID NO:26) domains based on those from antibody K4 was synthesized and subcloned into a Lenti-Puro vector. The construct had the following domain structure (from N-terminus to C-terminus): signal sequence-VH domain-linker-VL domain-CD8 hinge-CD28 endodomain-CD3 zeta endodomain and was under the control of the EF-1 alpha promoter (FIG. 12A). In particular, incorporation of the CD28 signaling endodomain in addition to CD3 zeta endodomain has been demonstrated to redirect and amplify CAR-T cell responses (see, e.g., Maher, J. et al. (2002) *Nat.*

Biotechnol. 20:70-75). The insert was confirmed by Sanger sequencing. The recombinant Lenti-CD274-CAR-puro was prepared by Qiagen plasmid maxi prep kit. The full CAR amino acid sequence is provided in SEQ ID NO:34.

To generate lentivirus, approximately 5×10$^6$ cells were seeded per 15 cm culture dish, and 25 mL DMEM culture medium containing 10% FBS was added. Cells were maintained in a 37° C., 5% $CO_2$ incubator overnight. Next, PEI stock (polyscience, CAT #23966-2) and lentivirus packaging system (Lenti-CAR, Lenti-Mix) were warmed to room temperature. After thorough mixing by pipetting up and down, 2 mL PBS, 10 μg Lenti-CAR, and 11 μg Lenti-Mix plasmid were added into one well of a 6-well plate. 26 μL 100 μM PEI was then added and mixed immediately. The plate was incubated at room temperature for 10 minutes.

The PEI/DNA complex was added into a 15 cm culture dish, and the dish was gently shaken. Dish was cultured for 6-8 hours in an incubator, the culture medium was refreshed. The dish was continuously cultured for 48 hours. After 48 hours, supernatant was harvested and filtered through a 0.45 μm membrane. The filtrate was centrifuged at 50,000×g for 2 hours at 4° C., then the pellet was resuspended in 1 mL PBS. Virus stock was aliquoted and stored at −80° C.

To titrate the lentivirus, HT1080 cells were recovered from liquid nitrogen and passaged until reaching exponential growth phase. 50,000 cells were inoculated into each well of a 24-well plate and supplemented with 500 μL culture medium. Cells were maintained in a 37° C., 5% $CO_2$ incubator overnight.

$10^{-2}$, $10^{-1}$, 1, or 10 μL lentivirus was added into each well along with polybrene at a final concentration of 6 μg/mL. Plate was incubated in a 37° C., 5% $CO_2$ incubator for 96 hours.

Cells were washed with PBS, and genomic DNA was extracted using a genomic DNA purification kit (Lifetech, CAT #K0512). NanoDrop 2000 spectrophotometer (Thermo Fisher Scientific) was used to determine DNA concentration.

PCR Detection

To detection successful transduction, PCR reaction were generated as shown in Table 2. Primers are listed in Table 3 below. WPRE (Woodchuck hepatitis virus post-transcriptional regulatory element) and ALB (albumin) represent known sequences in the lentiviral plasmid useful for viral titration; see, e.g., Barczak, W. et al. (2015) *Mol. Biotechnol.* 57:195-200.

TABLE 2

PCR reaction mix

| Reagent | Volume (20 μL) |
| --- | --- |
| 2 × PCR Mix | 10 |
| Probe Mix (WPRE probe, ALB probe) | 0.4 |
| Primer mix (WPRE F&R, ALB F&R) | 0.4 |
| PCR grade water | 4.2 |

TABLE 3

Primers used for diagnostic PCR.

| Primer | Sequence (5'-3') | SEQ ID NO | Fluorophore |
| --- | --- | --- | --- |
| WPRE F | GGCACTGACAATTCCGTGGT | 27 | |
| WPRE R | AGGGACGTAGCAGAAGGACG | 28 | |
| WPRE Probe | ACGTCCTTTCCATGGCTGCTCGC | 29 | 5'-FAM-BHQ1-3' |
| ALB F | GCTGTCATCTCTTGTGGGCTGT | 30 | |
| ALB R | ACTCATGGGAGCTGCTGGTTC | 31 | |
| ALB Probe | CCTGTCATGCCCACACAAATCTCTCC | 32 | 5'-FAM-BHQ1-3' |

A new 96-well plate was prepared, and 5 μL genomic DNA samples or standard curve was added per well along with 15 μL PCR reaction mix. Plate was sealed with membrane and briefly centrifuged for 1 min. PCR reaction thermocycles were as shown in Table 4.

TABLE 4

PCR thermocycles

| | Temp (° C.) | Time (sec) |
| --- | --- | --- |
| Initial Hot Start/denaturation | 95 | 30 |
| Steps 1-2 are repeated through 40 cycles | | |
| Step 1 | 95 | 5 |
| Step 2 | 60 | 30 |

Establishment of CAR-T Cells

To isolate CAR-T cells, Lymphoprep™ density gradient medium (STEMCELL Technologies) was mixed by tube inversion, and 15 mL Lymphoprep™ was added into a 50 mL tube in a biosafety cabinet. Peripheral blood samples were diluted with 1 volume of PBS. Diluted blood sample was slowly added onto the top of Lymphoprep™, then centrifuged at room temperature for 30 min at 800×g.

After centrifugation, PBMCs were collected from the interface between top yellow serum and the colorless Lymphoprep™ reagent and washed with PBS once. Cell density was adjusted to 1×10$^6$ cell/mL with PBS. Magnetic Dynabeads were added into the cell suspension at a bead:cell ratio of 3:1 and incubated for 30 minutes at room temperature. Magnet was used to isolate CD3+ T cells, and the cells were washed once with PBS.

Cells/Dynabeads were resuspended with X-vivo 15 medium containing 300 U/mL IL-2, 5 ng/mL IL-15 and 10 ng/mL IL-7. Cells were continuously cultured for 48 hours.

Transduction of Primary T Cells with Lentivirus

Cell density was adjusted to 1×10⁶ cells/mL in complete culture medium. Lentivirus amount was calculated as follows: Virus volume (mL)=(MOI*cell number)/virus titer.

Lentivirus and 6 μg/mL polybrene were added into the culture plate and centrifuged at 800×g for 1 hour. After centrifugation, the cells were cultured in a 37° C. 5% $CO_2$ incubator for 24 hours and passaged until ready for use.

Lysis of Target Cells by CAR-T Cells

Target cells were recovered from liquid nitrogen and routinely passaged twice prior to assay. Cell density was adjusted to 5×10⁵ cells/mL and 100 μL/well were inoculated into a 96-well plate. Plate was placed in a 5% $CO_2$ 37° C. incubator overnight.

CAR-T cells were resuspended with serum-free RPMI1640 medium and added into the 96-well plate according the E/T ratio as indicated. Plate was placed back in incubator and maintained for 6 hours.

After cultivation, lysis buffer was added into the "Maxi lysis" control well and centrifuged at 1200×g for 5 min. 50 μL supernatant was transferred to a new 96-well plate, and LDH substrate was added. The plate was incubated for 15 min, and $OD_{490\ nm}$ value was read using a microplate reader. Remaining supernatant was aliquoted for ELISA assay to determine the secretion of cytokines.

Percent lysis was calculated as follows:

$$\text{Lysis \%} = \frac{(OD\text{each well} - OD\text{mini lysis})}{OD\text{maxi lysis} - OD\text{mini lysis}} \times 100\%$$

Results

Figure 12B:
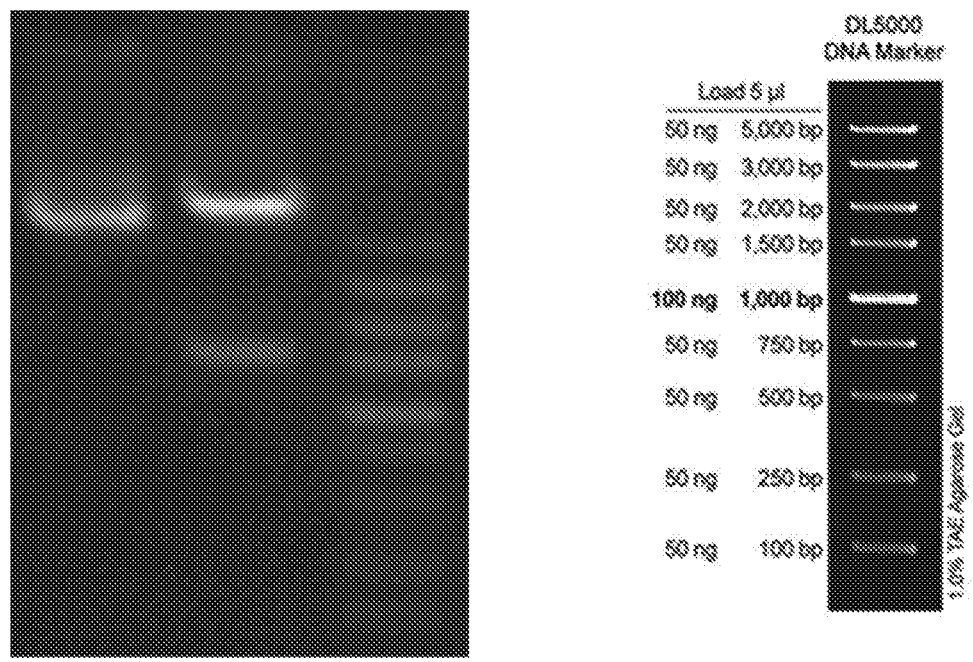
FIG. 12B shows expected DNA bands after EcoRI-BamHI digest of the lentiviral vector shown in FIG. 12A.

Recombinant lentiviral vector was digested with EcoRI and BamHI, and expected fragments were demonstrated using agarose gel electrophoresis (FIG. 12B). The recombinant vector was further sequenced to verify the correct construct. These results demonstrated that the vector shown in FIG. 12A was successfully produced.

Figure 13:
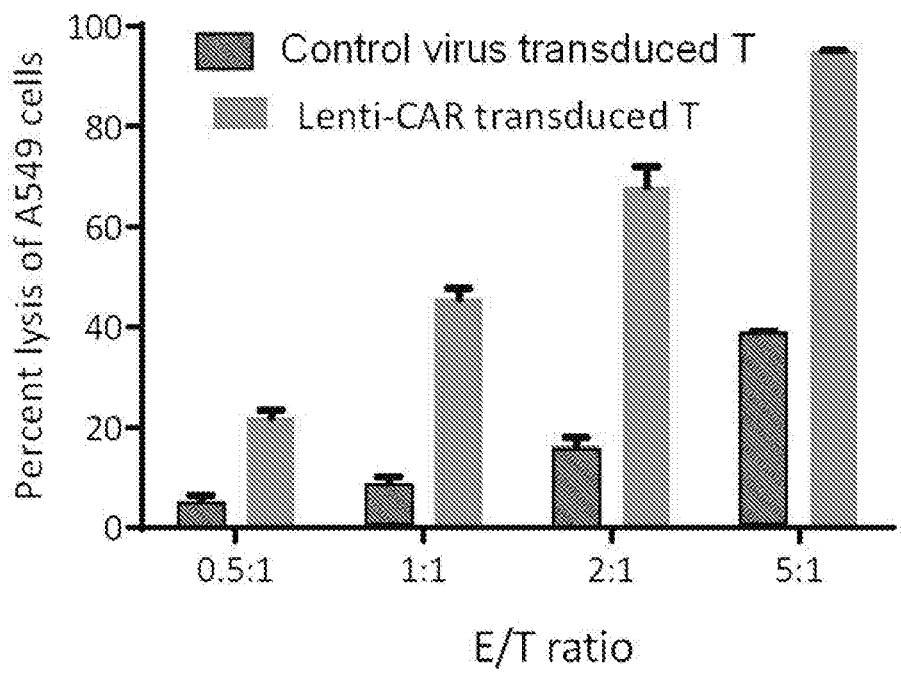
FIGS. 13-16 show CAR-T cell-mediated cell killing of tumor cell lines. Graphs depict percent lysis of target cells vs. indicated E/T ratios. Shown are assays for CAR-T-mediated killing of A549 lung adenocarcinoma (FIG. 13), BxPc-3 pancreatic adenocarcinoma (FIG. 14), HCT116 colorectal carcinoma (FIG. 15), and U87 glioblastoma (FIG. 16) cell lines.

To demonstrate that CAR-T cells transduced with this lentiviral vector were able to effect cell killing of target cells, A549 lung adenocarcinoma cells were used as target cells and the CAR-T cells as effector cells in a cell lysis assay. After co-culturing the two cell types for 8 hours, cell supernatant was harvested for determine the amount of LDH, indicating cell killing. As shown in FIG. 13, CAR-T cells were able to eliminate target cells efficiently, even at an E/T ratio as low as 0.5:1. These results demonstrate that the variable domains of the K4 antibody, which as shown in the previous Examples bind to N-acetylglucosamine and/or N-acetyl-galactosamine (or to glycoconjugates bearing distinct N-Acetyl glucosamine or N-acetyl-galactosamine moieties), are able to effect killing of target tumor cells when used in the context of a chimeric antigen receptor transduced into primary human T cells.

Figure 14:
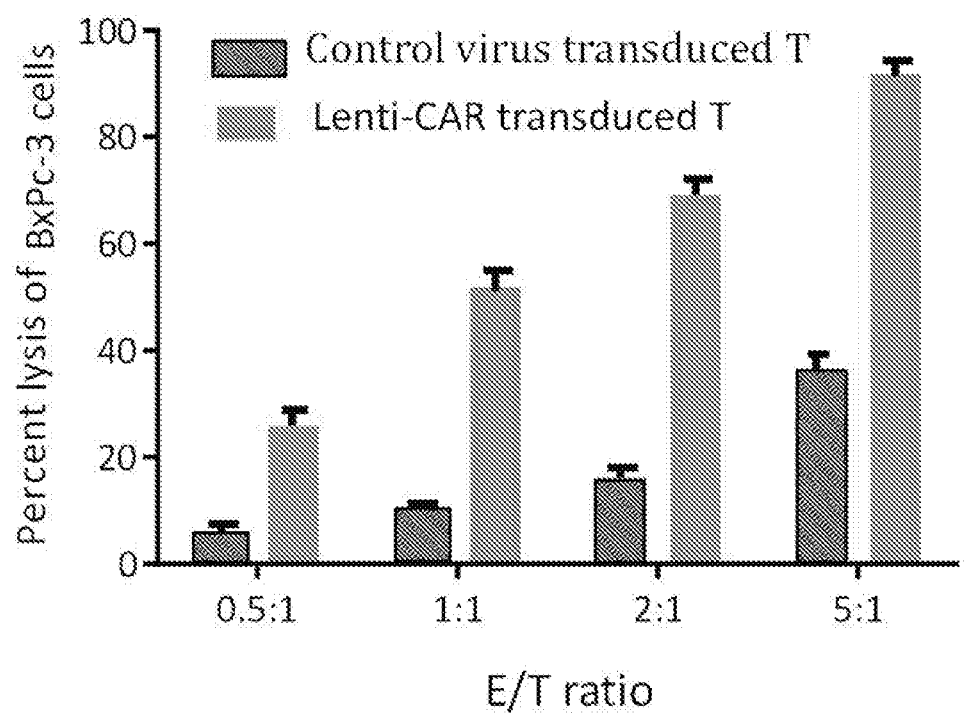

To demonstrate that the CAR-T cell strategy is able to effect killing of a range of tumor cells, CAR-T cells were tested in killing assays against pancreatic (BxPc-3), colorectal (HCT116), and glioblastoma (U87) tumor cell lines. First, BxPc-3 pancreatic cancer cells were used as target cells and the CAR-T cells as effector cells in a cell lysis assay. After co-culturing the two cell types for 8 hours, cell supernatant was harvested for determine the amount of LDH, indicating cell killing. As shown in FIG. 14, CAR-T cells were able to eliminate BxPc-3 cells efficiently, even at an E/T ratio as low as 0.5:1.

Figure 15:
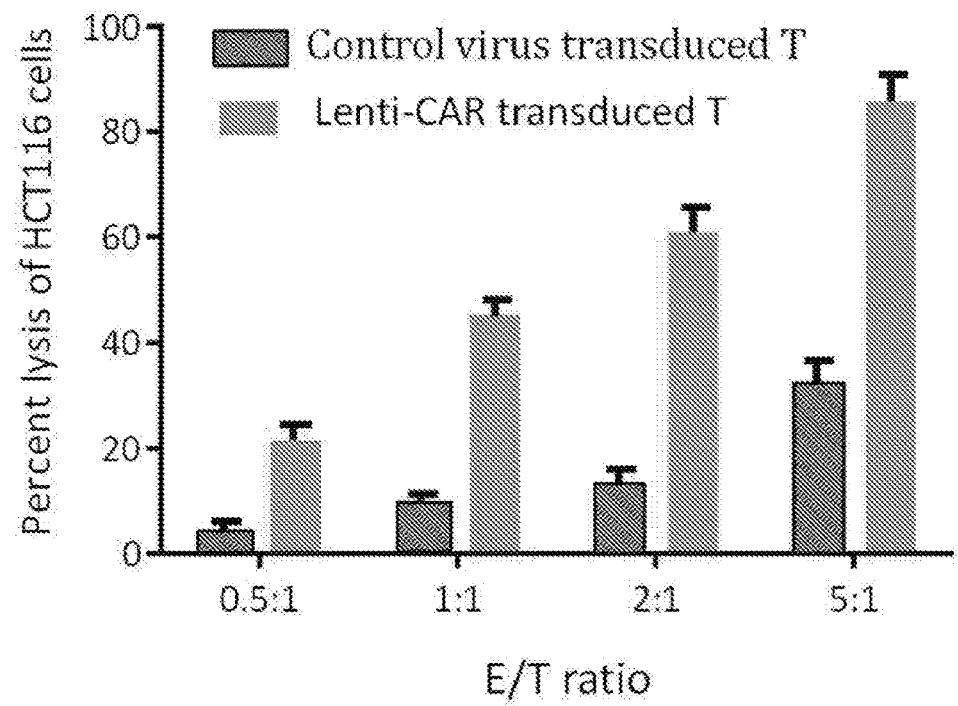

Next, HCT116 colorectal cancer cells were used as target cells and the CAR-T cells as effector cells in a cell lysis assay. After co-culturing the two cell types for 8 hours, cell supernatant was harvested for determine the amount of LDH, indicating cell killing. As shown in FIG. 15, CAR-T cells were able to eliminate HCT116 cells efficiently, even at an E/T ratio as low as 0.5:1.

Figure 16:
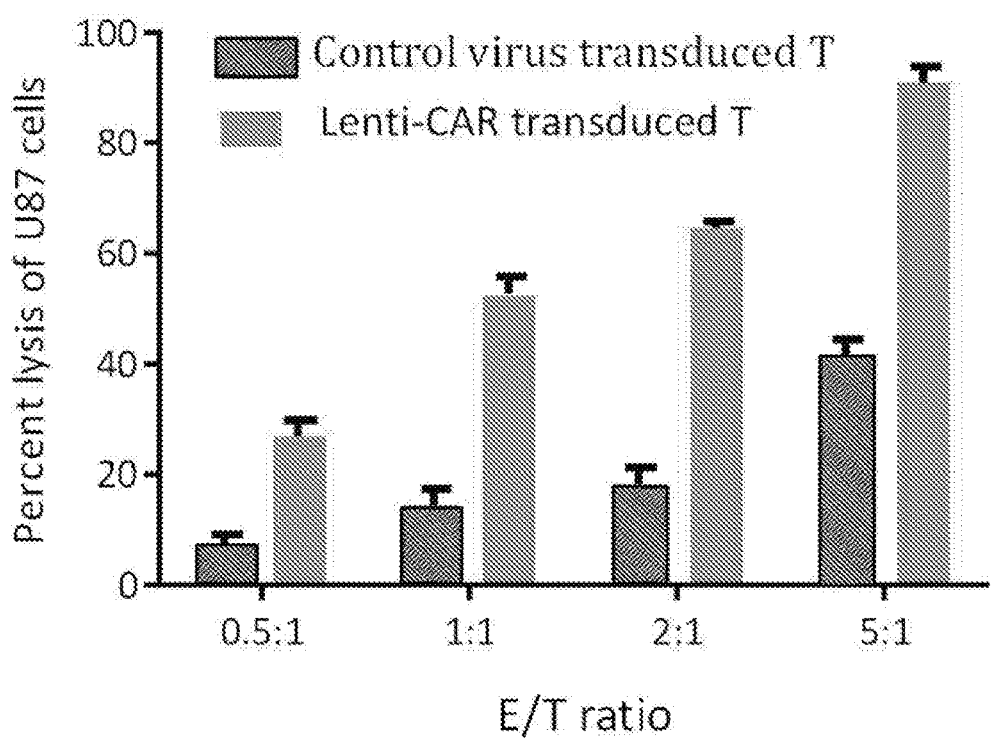

Next, U87 glioblastoma cancer cells were used as target cells and the CAR-T cells as effector cells in a cell lysis assay. After co-culturing the two cell types for 8 hours, cell supernatant was harvested for determine the amount of LDH, indicating cell killing. As shown in FIG. 16, CAR-T cells were able to eliminate U87 cells efficiently, even at an E/T ratio as low as 0.5:1.

Taken together, these results indicate that human T cells bearing a CAR with the K4 antibody specificity were able to efficiently effect cell killing of lung, pancreatic, colorectal, and brain cancer cell lines, demonstrating the wide applicability of this CAR-T cell approach for mediating tumor cell killing.

SEQUENCES

All polypeptide sequences are presented N-terminal to C-terminal unless otherwise noted. All nucleic acid sequences are presented 5' to 3' unless otherwise noted.

Humanized parental 1C5C9 and 1C5C9-VK1/VK2/VK3/VK4 HVR-H1:
(SEQ ID NO: 1)
YTFPDYNIH Humanized parental 1C5C9 and 1C5C9-VK1/VK2/VK3/VK4 HVR-H2:
(SEQ ID NO: 2)
CIYPYNGNTA Humanized parental 1C5C9 and 1C5C9-VK1/VK2/VK3/VK4 HVR-H3:
(SEQ ID NO: 3)
SDLYYFGSRGFD Humanized parental 1C5C9/1C5C9-VK2 HVR-L1:
(SEQ ID NO: 4)
RASQDISTYLN Humanized 1C5C9-VK3/VK4 HVR-L1:
(SEQ ID NO: 5)
RASQDISTYLA Humanized parental 1C5C9 HVR-L2:
(SEQ ID NO: 6)
FTSRLHS -continued Humanized 1C5C9-VK3 HVR-L2:
(SEQ ID NO: 7)
FTSTLQS Humanized 1C5C9-VK4 HVR-L2:
(SEQ ID NO: 8)
FTSSLES Humanized parental 1C5C9 and 1C5C9-VK1/VK2/VK3/VK4 HVR-L3:
(SEQ ID NO: 9)
QQGNTLPW Humanized parental and 1C5C9-VK1/VK2/VK3/VK4 Heavy Chain Variable Region:
(SEQ ID NO: 10)
QVQLVQSGAEVKKPGASVKVSCKASGYTFPDYNIHWVRQAPGQGLEWMGCIYPYN

GNTAYAQKFQGRVTMTRDTSISTAYMELSRLRSDDTAVYYCARSDLYYFGSRGFDY

WGQGTLVTVSSA

Humanized parental and 1C5C9-VK1/VK2/VK3/VK4 Heavy Chain:
(SEQ ID NO: 11)
QVQLVQSGAEVKKPGASVKVSCKASGYTFPDYNIHWVRQAPGQGLEWMGCIYPYN

GNTAYAQKFQGRVTMTRDTSISTAYMELSRLRSDDTAVYYCARSDLYYFGSRGFDY

WGQGTLVTVSSASTKGPSVFPLAPSSKSTSGGTAALGCLVKDYFPEPVTVSWNSGAL

TSGVHTFPAVLQSSGLYSLSSVVTVPSSSLGTQTYICNVNHKPSNTKVDKRVEPKSCD

KTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK

Humanized parental 1C5C9 Light Chain Variable Region:
(SEQ ID NO: 12)
DIQMTQSPSSLSASVGDRVTITCRASQDISTYLNWYQQKPGKAPKLLIYFTSRLHSGVP

SRFSGSGSGTDFTLTISSLQPEDIATYYCQQGNTLPWTFGGGTKLEIK

Humanized 1C5C9-VK3 Light Chain Variable Region:
(SEQ ID NO: 13)
DIQMTQSPSSLSASVGDRVTITCRASQDISTYLAWYQQKPGKAPKLLIYFTSTLQSGVP

SRFSGSGSGTDFTLTISSLQPEDAATYYCQQGNTLPWTFGGGTKLEIK

Humanized 1C5C9-VK4 Light Chain Variable Region:
(SEQ ID NO: 14)
AIQLTQSPSSLSASVGDRVTITCRASQDISTYLAWYQQKPGKAPKLLIYFTSSLESGVP

SRFSGSGSGTDFTLTISSLQPEDVATYYCQQGNTLPWTFGGGTKLEIK

Humanized parental 1C5C9 Light Chain:
(SEQ ID NO: 15)
DIQMTQSPSSLSASVGDRVTITCRASQDISTYLNWYQQKPGKAPKLLIYFTSRLHSGVP

SRFSGSGSGTDFTLTISSLQPEDIATYYCQQGNTLPWTFGGGTKLEIKRTVAAPSVFIFP

PSDEQLKSGTASVVCLLNNFYPREAKVQWKVDNALQSGNSQESVTEQDSKDSTYSLS

STLTLSKADYEKHKVYACEVTHQGLSSPVTKSFNRGEC

Humanized 1C5C9-VK3 Light Chain:
(SEQ ID NO: 16)
DIQMTQSPSSLSASVGDRVTITCRASQDISTYLAWYQQKPGKAPKLLIYFTSTLQSGVP

SRFSGSGSGTDFTLTISSLQPEDAATYYCQQGNTLPWTFGGGTKLEIKRTVAAPSVFIF

PPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

-continued

Humanized 1C5C9-VK4 Light Chain:
(SEQ ID NO: 17)
AIQLTQSPSSLSASVGDRVTITCRASQDISTYLAWYQQKPGKAPKLLIYFTSSLESGVP
SRFSGSGSGTDFTLTISSLQPEDVATYYCQQGNTLPWTFGGGTKLEIKRTVAAPSVFIF
PPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC Humanized 1C5C9-VK2 HVR-L2:
(SEQ ID NO: 18)
FTSSLQS Humanized 1C5-VK2 Light Chain Variable Region:
(SEQ ID NO: 19)
DIQMTQSPSSLSASVGDRVTITCRASQDISTYLNWYQQKPGKAPKLLIYFTSSLQSGVP
SRFSGSGSGTDFTLTISSLQPEDIATYYCQQGNTLPWTFGGGTKLEIK Humanized 1C5-VK2 Light Chain:
(SEQ ID NO: 20)
DIQMTQSPSSLSASVGDRVTITCRASQDISTYLNWYQQKPGKAPKLLIYFTSSLQSGVP
SRFSGSGSGTDFTLTISSLQPEDIATYYCQQGNTLPWTFGGGTKLEIKRTVAAPSVFIFP
PSDEQLKSGTASVVCLLNNFYPREAKVQWKVDNALQSGNSQESVTEQDSKDSTYSLS
STLTLSKADYEKHKVYACEVTHQGLSSPVTKSFNRGEC Humanized 1C5C9-VK1 HVR-L1:
(SEQ ID NO: 21)
QASQDISTYLN Humanized 1C5C9-VK1 HVR-L2:
(SEQ ID NO: 22)
FTSNLET Humanized 1C5-VK1 Light Chain Variable Region:
(SEQ ID NO: 23)
DIQMTQSPSSLSASVGDRVTITCQASQDISTYLNWYQQKPGKAPKLLIYFTSNLETGV
PSRFSGSGSGTDFTLTISSLQPEDIATYYCQQGNTLPWTFGGGTKLEIK Humanized 1C5-VK1 Light Chain:
(SEQ ID NO: 24)
DIQMTQSPSSLSASVGDRVTITCQASQDISTYLNWYQQKPGKAPKLLIYFTSNLETGV
PSRFSGSGSGTDFTLTISSLQPEDIATYYCQQGNTLPWTFGGGTKLEIKRTVAAPSVFIF
PPSDEQLKSGTASVVCLLNNFYPREAKVQWKVDNALQSGNSQESVTEQDSKDSTYSL
SSTLTLSKADYEKHKVYACEVTHQGLSSPVTKSFNRGEC Consensus humanized 1C5C9-VK3/-VK4 HVR-L2:
(SEQ ID NO: 25)
FTSX$_1$LX$_2$S VK4 light chain variable region used for CAR
(SEQ ID NO: 26)
AIQLTQSPSSLSASVGDRVTITCRASQDISTYLAWYQQKPGKAPKLLIYFTSSLESGVP
SRFSGSGSGTDFTLTISSLQPEDFATYYCQQGNTLPWTFGGGTKLEIKRTVAAPSVFI WPRE forward primer
(SEQ ID NO: 27)
GGCACTGACAATTCCGTGGT WPRE reverse primer
(SEQ ID NO: 28)
AGGGACGTAGCAGAAGGACG WPRE probe
(SEQ ID NO: 29)
ACGTCCTTTCCATGGCTGCTCGC ALB forward primer
(SEQ ID NO: 30)
GCTGTCATCTCTTGTGGGCTGT -continued ALB reverse primer
(SEQ ID NO: 31)
ACTCATGGGAGCTGCTGGTTC ALB probe
(SEQ ID NO: 32)
CCTGTCATGCCCACACAAATCTCTCC VK4 heavy chain variable region used for CAR
(SEQ ID NO: 33)
QVQLVSGAEVKKPGASVKVSCKASGYTFPDYNIHWVRQAPGQGLEWMGCIYPYN

GNTAYAQKFQGRVTMTRDTSISTAYMELSRLRSDDTAVYYCARSDLYYFGSRGFDY

WGQGTLVTVSSG

CAR amino acid sequence
(SEQ ID NO: 34)
MALPVTALLLPLALLLHAARPQVQLVQSGAEVKKPGASVKVSCKASGYTFPDYNIH

WVRQAPGQGLEWMGCIYPYNGNTAYAQKFQGRVTMTRDTSISTAYMELSRLRSDD

TAVYYCARSDLYYFGSRGFDYWGQGTLVTVSSAGGGGSGGGGSGGGGSAIQLTQSP

SSLSASVGDRVTITCRASQDISTYLAWYQQKPGKAPKLLIYFTSSLESGVPSRFSGSGS

GTDFTLTISSLQPEDFATYYCQQGNTLPWTFGGGTKLEIKRTVAAPSVFITTTPAPRPP

TPAPTIASQPLSLRPEACRPAAGGAVHTRGLDFACDFWVLVVVGGVLACYSLLVTVA

FIIFWVRSKRSRLLHSDYMNMTPRRPGPTRKHYQPYAPPRDFAAYRSRVKFSRSADA

PAYKQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

---

What is claimed is:

1. An isolated monoclonal antibody that specifically binds to an epitope comprising N-acetylglucosamine or N-acetylgalactosamine, wherein the antibody comprises a light chain variable region comprising an HVR-L1 sequence of SEQ ID NO: 5, an HVR-L2 sequence of FTSX1LX2S (SEQ ID NO: 25), and an HVR-L3 sequence of SEQ ID NO: 9, wherein X1 is T or S and X2 is Q or E, and wherein the antibody comprises a heavy chain variable region comprising an HVR-H1 sequence of SEQ ID NO: 1, an HVR-H2 sequence of SEQ ID NO: 2, and an HVR-H3 sequence of SEQ ID NO: 3.

2. The antibody of claim 1, wherein the HVR-L2 sequence comprises the amino acid sequence of SEQ ID NO: 7 or SEQ ID NO: 8.

3. The antibody of claim 2, wherein the antibody comprises a light chain variable region comprising the amino acid sequence of SEQ ID NO: 13 or SEQ ID NO: 14.

4. The antibody of claim 3, wherein the antibody comprises a light chain comprising the amino acid sequence of SEQ ID NO: 16 or SEQ ID NO: 17.

5. The antibody of claim 1, wherein the antibody comprises a heavy chain variable region comprising the amino acid sequence of SEQ ID NO: 10.

6. The antibody of claim 5, wherein the antibody comprises a heavy chain comprising the amino acid sequence of SEQ ID NO: 11.

7. An isolated polynucleotide comprising a nucleic acid sequence encoding the antibody of claim 1.

8. An isolated host cell comprising the polynucleotide of claim 7.

9. A method of producing an antibody, comprising culturing the host cell of claim 8 that produces the antibody, and recovering the antibody from the cell culture.

10. A composition comprising the antibody of claim 1 and a pharmaceutically acceptable carrier.

11. A method for treating cancer in an individual, comprising administering to the individual an effective amount of a composition comprising the antibody of claim 1.

12. The method of claim 11, wherein the individual is a human.

13. A method for detecting cancer cells in an individual, comprising:

(a) contacting a biological sample from the individual with the antibody of claim 1; and (b) detecting binding of the antibody to the biological sample, wherein binding of the antibody to the sample may indicate the presence of cancer cells in the individual.

14. A method for treating gastrointestinal disease in an individual comprising administering to the individual an effective amount of the antibody of claim 1.

15. A kit comprising a pharmaceutical composition comprising the antibody of claim 1.

16. A chimeric antigen receptor (CAR) that specifically binds to an epitope comprising N-acetylglucosamine or N-acetyl-galactosamine, wherein the CAR comprises a light chain variable region comprising an HVR-L 1 sequence of SEQ ID NO: 5, an HVR-L2 sequence of FTSX1LX2S (SEQ ID NO: 25), and an HVR-L3 sequence of SEQ ID NO: 9, wherein X1 is T or S and X2 is Q or E and a heavy chain variable region comprising an HVR-H1 sequence of SEQ ID NO: 1, an HVR-H2 sequence of SEQ ID NO: 2, and an HVR-H3 sequence of SEQ ID NO: 3.

17. An isolated polynucleotide comprising a nucleic acid sequence encoding the CAR of claim 16.

18. An isolated T cell comprising the CAR of claim 16, wherein the CAR is expressed on a cell surface of the T cell.

* * * * *

SEQUENCE LISTING

<160> NUMBER OF SEQ ID NOS: 34

<210> SEQ ID NO 1
<211> LENGTH: 9
<212> TYPE: PRT
<213> ORGANISM: Artificial Sequence
<220> FEATURE:
<223> OTHER INFORMATION: Humanized parental1C5C9and 1C5C9-VK1/VK2/VK3/
      VK4HVR-H1

<400> SEQUENCE: 1

Tyr Thr Phe Pro Asp Tyr Asn Ile His
1               5

<210> SEQ ID NO 2
<211> LENGTH: 10
<212> TYPE: PRT
<213> ORGANISM: Artificial Sequence
<220> FEATURE:
<223> OTHER INFORMATION: Humanized parental 1C5C9and 1C5C9-VK1/VK2/VK3/
      VK4HVR-H2

<400> SEQUENCE: 2

Cys Ile Tyr Pro Tyr Asn Gly Asn Thr Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Humanized parental 1C5C9and 1C5C9-VK1/VK2/VK3/
      VK4HVR-H3

<400> SEQUENCE: 3

```
Ser Asp Leu Tyr Tyr Phe Gly Ser Arg Gly Phe Asp
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Humanized parental1C5C9/1C5C9-VK2HVR-L1

<400> SEQUENCE: 4

Arg Ala Ser Gln Asp Ile Ser Thr Tyr Leu Asn
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Humanized 1C5C9-VK3/VK4 HVR-L1

<400> SEQUENCE: 5

Arg Ala Ser Gln Asp Ile Ser Thr Tyr Leu Ala
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Humanized parental1C5C9 HVR-L2

<400> SEQUENCE: 6

Phe Thr Ser Arg Leu His Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Humanized 1C5C9-VK3 HVR-L2

<400> SEQUENCE: 7

Phe Thr Ser Thr Leu Gln Ser
1               5

<210> SEQ ID NO 8
<211> LENGTH: 7
<212> TYPE: PRT
<213> ORGANISM: Artificial Sequence
<220> FEATURE:
<223> OTHER INFORMATION: Humanized 1C5C9-VK4 HVR-L2

<400> SEQUENCE: 8

Phe Thr Ser Ser Leu Glu Ser
1               5

<210> SEQ ID NO 9
<211> LENGTH: 8
<212> TYPE: PRT
<213> ORGANISM: Artificial Sequence
<220> FEATURE:
<223> OTHER INFORMATION: Humanized parental 1C5C9 and 1C5C9-VK1/VK2/VK3/
      VK4HVR-L3

<400> SEQUENCE: 9
```

Gln Gln Gly Asn Thr Leu Pro Trp
1               5

<210> SEQ ID NO 10
<211> LENGTH: 123
<212> TYPE: PRT
<213> ORGANISM: Artificial Sequence
<220> FEATURE:
<223> OTHER INFORMATION: Humanized parental and 1C5C9-VK1/VK2/VK3/VK4
      Heavy Chain Variable Region

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Asn Ile His Trp Val Arg Gln Ala Pro Gly Gln Gly Leu Glu Trp Met
        35                  40                  45

Gly Cys Ile Tyr Pro Tyr Asn Gly Asn Thr Ala Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Leu Tyr Tyr Phe Gly Ser Arg Gly Phe Asp Tyr Trp
            100                 105                 110

Gly Gln Gly Thr Leu Val Thr Val Ser Ser Ala
        115                 120

<210> SEQ ID NO 11
<211> LENGTH: 452
<212> TYPE: PRT
<213> ORGANISM: Artificial Sequence
<220> FEATURE:
<223> OTHER INFORMATION: Humanized parental and 1C5C9-VK1/VK2/VK3/VK4
      Heavy Chain

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Asn Ile His Trp Val Arg Gln Ala Pro Gly Gln Gly Leu Glu Trp Met
        35                  40                  45

Gly Cys Ile Tyr Pro Tyr Asn Gly Asn Thr Ala Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Leu Tyr Tyr Phe Gly Ser Arg Gly Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 12
<211> LENGTH: 107
<212> TYPE: PRT
<213> ORGANISM: Artificial Sequence
<220> FEATURE:
<223> OTHER INFORMATION: Humanized parental1C5C9 Light Chain Variable
      Region

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
            35                  40                  45

Tyr Phe Thr Ser Arg Leu His Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Gly Asn Thr Leu Pro Trp
                 85                  90                  95

Thr Phe Gly Gly Gly Thr Lys Leu Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Humanized 1C5C9-VK3 Light Chain Variable Region

<400> SEQUENCE: 13

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Thr Tyr
                20                  25                  30

Leu Ala Trp Tyr Gln Gln Lys Pro Gly Lys Ala Pro Lys Leu Leu Ile
            35                  40                  45

Tyr Phe Thr Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Asn Thr Leu Pro Trp
                 85                  90                  95

Thr Phe Gly Gly Gly Thr Lys Leu Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: Humanized 1C5C9-VK4 Light Chain Variable Region

<400> SEQUENCE: 14

Ala Ile Gln Leu Thr Gln Ser Pro Ser Ser Leu Ser Ala Ser Val Gly
 1               5                  10                  15

Asp Arg Val Thr Ile Thr Cys Arg Ala Ser Gln Asp Ile Ser Thr Tyr
                20                  25                  30

Leu Ala Trp Tyr Gln Gln Lys Pro Gly Lys Ala Pro Lys Leu Leu Ile
            35                  40                  45

Tyr Phe Thr Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Gly Asn Thr Leu Pro Trp
                 85                  90                  95

Thr Phe Gly Gly Gly Thr Lys Leu Glu Ile Lys
            100                 105

<210> SEQ ID NO 15
<211> LENGTH: 214
<212> TYPE: PRT
<213> ORGANISM: Artificial Sequence
<220> FEATURE:
```

<223> OTHER INFORMATION: Humanized parental1C5C9 Light Chain

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 214
<212> TYPE: PRT
<213> ORGANISM: Artificial Sequence
<220> FEATURE:
<223> OTHER INFORMATION: Humanized 1C5C9-VK3 Light Chain

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Ala Trp Tyr Gln Gln Lys Pro Gly Lys Ala Pro Lys Leu Leu Ile
        35                  40                  45

Tyr Phe Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 214
<212> TYPE: PRT
<213> ORGANISM: Artificial Sequence
<220> FEATURE:
<223> OTHER INFORMATION: Humanized 1C5C9-VK4 Light Chain

<400> SEQUENCE: 17

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Ala Trp Tyr Gln Gln Lys Pro Gly Lys Ala Pro Lys Leu Leu Ile
        35                  40                  45

Tyr Phe Thr Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 7
<212> TYPE: PRT
<213> ORGANISM: Artificial Sequence
<220> FEATURE:
<223> OTHER INFORMATION: Humanized 1C5C9-VK2 HVR-L
```

<400> SEQUENCE: 18

Phe Thr Ser Ser Leu Gln Ser
1               5

<210> SEQ ID NO 19
<211> LENGTH: 107
<212> TYPE: PRT
<213> ORGANISM: Artificial Sequence
<220> FEATURE:
<223> OTHER INFORMATION: Humanized 1C5-VK2 Light Chain Variable Region

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys
            100                 105

<210> SEQ ID NO 20
<211> LENGTH: 214
<212> TYPE: PRT
<213> ORGANISM: Artificial Sequence
<220> FEATURE:
<223> OTHER INFORMATION: Humanized 1C5-VK2 Light Chain

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 11
<212> TYPE: PRT
<213> ORGANISM: Artificial Sequence
<220> FEATURE:
<223> OTHER INFORMATION: Humanized 1C5C9-VK1 HVR-L1

<400> SEQUENCE: 21

Gln Ala Ser Gln Asp Ile Ser Thr Tyr Leu Asn
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Humanized 1C5C9-VK1 HVR-L2

<400> SEQUENCE: 22

Phe Thr Ser Asn Leu Glu Thr
1               5

<210> SEQ ID NO 23
<211> LENGTH: 107
<212> TYPE: PRT
<213> ORGANISM: Artificial Sequence
<220> FEATURE:
<223> OTHER INFORMATION: Humanized 1C5-VK1 Light Chain Variable Region

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys
            100                 105

<210> SEQ ID NO 24
<211> LENGTH: 214
<212> TYPE: PRT
<213> ORGANISM: Artificial Sequence
<220> FEATURE:
<223> OTHER INFORMATION: Humanized 1C5-VK1 Light Chain

<400> SEQUENCE: 24

Asp Ile Gln Met Thr Gln Ser Pro Ser Ser Leu Ser Ala Ser Val Gly
1               5                   10                  15

-continued

```
Asp Arg Val Thr Ile Thr Cys Gln Ala Ser Gln Asp Ile Ser Thr Tyr
            20                  25                  30

Leu Asn Trp Tyr Gln Gln Lys Pro Gly Lys Ala Pro Lys Leu Leu Ile
        35                  40                  45

Tyr Phe Thr Ser Asn Leu Glu Thr Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 7
<212> TYPE: PRT
<213> ORGANISM: Artificial Sequence
<220> FEATURE:
<223> OTHER INFORMATION: Consensus humanized 1C5C9-VK3/-VK4 HVR-L2
<220> FEATURE:
<221> NAME/KEY: VARIANT
<222> LOCATION: (4)..(4)
<223> OTHER INFORMATION: Xaa is Thr or Ser
<220> FEATURE:
<221> NAME/KEY: VARIANT
<222> LOCATION: (6)..(6)
<223> OTHER INFORMATION: Xaa is Gln or Glu

<400> SEQUENCE: 25

Phe Thr Ser Xaa Leu Xaa Ser
1               5

<210> SEQ ID NO 26
<211> LENGTH: 117
<212> TYPE: PRT
<213> ORGANISM: Artificial Sequence
<220> FEATURE:
<223> OTHER INFORMATION: VK4 light chain variable region used for CAR

<400> SEQUENCE: 26

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Thr Tyr
            20                  25                  30

Leu Ala Trp Tyr Gln Gln Lys Pro Gly Lys Ala Pro Lys Leu Leu Ile
        35                  40                  45
```

-continued

```
Tyr Phe Thr Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Asn Thr Leu Pro Trp
                 85                  90                  95
Thr Phe Gly Gly Gly Thr Lys Leu Glu Ile Lys Arg Thr Val Ala Ala
            100                 105                 110
Pro Ser Val Phe Ile
        115
```

<210> SEQ ID NO 27
<211> LENGTH: 20
<212> TYPE: DNA
<213> ORGANISM: Artificial Sequence
<220> FEATURE:
<223> OTHER INFORMATION: WPRE forward primer

<400> SEQUENCE: 27
ggcactgaca attccgtggt                                          20

<210> SEQ ID NO 28
<211> LENGTH: 20
<212> TYPE: DNA
<213> ORGANISM: Artificial Sequence
<220> FEATURE:
<223> OTHER INFORMATION: WPRE reverse primer

<400> SEQUENCE: 28
agggacgtag cagaaggacg                                          20

<210> SEQ ID NO 29
<211> LENGTH: 23
<212> TYPE: DNA
<213> ORGANISM: Artificial Sequence
<220> FEATURE:
<223> OTHER INFORMATION: WPRE probe

<400> SEQUENCE: 29
acgtcctttc catggctgct cgc                                      23

<210> SEQ ID NO 30
<211> LENGTH: 22
<212> TYPE: DNA
<213> ORGANISM: Artificial Sequence
<220> FEATURE:
<223> OTHER INFORMATION: ALB forward primer

<400> SEQUENCE: 30
gctgtcatct cttgtgggct gt                                       22

<210> SEQ ID NO 31
<211> LENGTH: 21
<212> TYPE: DNA
<213> ORGANISM: Artificial Sequence
<220> FEATURE:
<223> OTHER INFORMATION: ALB reverse primer

<400> SEQUENCE: 31
actcatggga gctgctggtt c                                        21

<210> SEQ ID NO 32
<211> LENGTH: 26
<212> TYPE: DNA

```
<213> ORGANISM: Artificial Sequence
<220> FEATURE:
<223> OTHER INFORMATION: ALB probe

<400> SEQUENCE: 32
cctgtcatgc ccacacaaat ctctcc                                           26

<210> SEQ ID NO 33
<211> LENGTH: 123
<212> TYPE: PRT
<213> ORGANISM: Artificial Sequence
<220> FEATURE:
<223> OTHER INFORMATION: VK4 heavy chain variable region used for CAR

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Asp Tyr
            20                  25                  30

Asn Ile His Trp Val Arg Gln Ala Pro Gly Gln Gly Leu Glu Trp Met
        35                  40                  45

Gly Cys Ile Tyr Pro Tyr Asn Gly Asn Thr Ala Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Asp Leu Tyr Tyr Phe Gly Ser Arg Gly Phe Asp Tyr Trp
            100                 105                 110

Gly Gln Gly Thr Leu Val Thr Val Ser Ser Gly
        115                 120

<210> SEQ ID NO 34
<211> LENGTH: 501
<212> TYPE: PRT
<213> ORGANISM: Artificial Sequence
<220> FEATURE:
<223> OTHER INFORMATION: CAR amino acid sequence

<400> SEQUENCE: 34

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Thr Phe Pro Asp Tyr Asn Ile His Trp Val Arg Gln Ala Pro Gly Gln
    50                  55                  60

Gly Leu Glu Trp Met Gly Cys Ile Tyr Pro Tyr Asn Gly Asn Thr Ala
65                  70                  75                  80

Tyr Ala Gln Lys Phe Gln Gly Arg Val Thr Met Thr Arg Asp Thr Ser
                85                  90                  95

Ile Ser Thr Ala Tyr Met Glu Leu Ser Arg Leu Arg Ser Asp Asp Thr
            100                 105                 110

Ala Val Tyr Tyr Cys Ala Arg Ser Asp Leu Tyr Tyr Phe Gly Ser Arg
        115                 120                 125

Gly Phe Asp Tyr Trp Gly Gln Gly Thr Leu Val Thr Val Ser Ser Ala
    130                 135                 140
```

Gly Gly Gly Ser Gly Gly Gly Ser Gly Gly Gly Ser Ala
145             150             155             160

Ile Gln Leu Thr Gln Ser Pro Ser Leu Ser Ala Ser Val Gly Asp
                165             170             175

Arg Val Thr Ile Thr Cys Arg Ala Ser Gln Asp Ile Ser Thr Tyr Leu
            180             185             190

Ala Trp Tyr Gln Gln Lys Pro Gly Lys Ala Pro Lys Leu Leu Ile Tyr
        195             200             205

Phe Thr Ser Ser Leu Glu Ser Gly Val Pro Ser Arg Phe Ser Gly Ser
        210             215             220

Gly Ser Gly Thr Asp Phe Thr Leu Thr Ile Ser Ser Leu Gln Pro Glu
225             230             235             240

Asp Phe Ala Thr Tyr Tyr Cys Gln Gln Gly Asn Thr Leu Pro Trp Thr
            245             250             255

Phe Gly Gly Gly Thr Lys Leu Glu Ile Lys Arg Thr Val Ala Ala Pro
            260             265             270

Ser Val Phe Ile Thr Thr Thr Pro Ala Pro Arg Pro Pro Thr Pro Ala
        275             280             285

Pro Thr Ile Ala Ser Gln Pro Leu Ser Leu Arg Pro Glu Ala Cys Arg
    290             295             300

Pro Ala Ala Gly Gly Ala Val His Thr Arg Gly Leu Asp Phe Ala Cys
305             310             315             320

Asp Phe Trp Val Leu Val Val Val Gly Gly Val Leu Ala Cys Tyr Ser
            325             330             335

Leu Leu Val Thr Val Ala Phe Ile Ile Phe Trp Val Arg Ser Lys Arg
            340             345             350

Ser Arg Leu Leu His Ser Asp Tyr Met Asn Met Thr Pro Arg Arg Pro
        355             360             365

Gly Pro Thr Arg Lys His Tyr Gln Pro Tyr Ala Pro Pro Arg Asp Phe
    370             375             380

Ala Ala Tyr Arg Ser Arg Val Lys Phe Ser Arg Ser Ala Asp Ala Pro
385             390             395             400

Ala Tyr Lys Gln Gly Gln Asn Gln Leu Tyr Asn Glu Leu Asn Leu Gly
            405             410             415

Arg Arg Glu Glu Tyr Asp Val Leu Asp Lys Arg Arg Gly Arg Asp Pro
            420             425             430

Glu Met Gly Gly Lys Pro Arg Arg Lys Asn Pro Gln Glu Gly Leu Tyr
        435             440             445

Asn Glu Leu Gln Lys Asp Lys Met Ala Glu Ala Tyr Ser Glu Ile Gly
    450             455             460

Met Lys Gly Glu Arg Arg Arg Gly Lys Gly His Asp Gly Leu Tyr Gln
465             470             475             480

Gly Leu Ser Thr Ala Thr Lys Asp Thr Tyr Asp Ala Leu His Met Gln
            485             490             495

Ala Leu Pro Pro Arg
            500